(12) United States Patent
Kobayashi et al.

(10) Patent No.: US 8,791,263 B2
(45) Date of Patent: Jul. 29, 2014

(54) CORTISTATIN A ANALOG AND USE THEREOF

(75) Inventors: Motomasa Kobayashi, Osaka (JP); Naoyuki Kotoku, Osaka (JP); Masayoshi Arai, Osaka (JP); Satoru Tamura, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 13/823,265

(22) PCT Filed: Sep. 16, 2011

(86) PCT No.: PCT/JP2011/071264
§ 371 (c)(1),
(2), (4) Date: May 2, 2013

(87) PCT Pub. No.: WO2012/036287
PCT Pub. Date: Mar. 22, 2012

(65) Prior Publication Data
US 2013/0210859 A1     Aug. 15, 2013

(30) Foreign Application Priority Data
Sep. 17, 2010  (JP) .................. 2010-209131

(51) Int. Cl.
| | | |
|---|---|---|
| *C07D 405/04* | (2006.01) | |
| *C07D 217/02* | (2006.01) | |
| *A61K 45/00* | (2006.01) | |
| *A61K 31/4725* | (2006.01) | |
| *A61P 43/00* | (2006.01) | |
| *A61P 35/00* | (2006.01) | |
| *C07D 407/10* | (2006.01) | |
| *C07F 7/18* | (2006.01) | |
| *A61K 45/06* | (2006.01) | |

(52) U.S. Cl.
CPC .......... *C07D 407/10* (2013.01); *A61K 31/4725* (2013.01); *C07D 405/04* (2013.01); *C07F 7/1856* (2013.01); *A61K 45/06* (2013.01)
USPC ........ 546/144; 546/167; 546/283.1; 514/307; 514/311; 514/337

(58) Field of Classification Search
USPC ........................................... 546/144; 514/307
See application file for complete search history.

(56) References Cited

U.S. PATENT DOCUMENTS

| | | |
|---|---|---|
| 2011/0060140 A1 | 3/2011 | Shenvi et al. |
| 2011/0190323 A1 | 8/2011 | Flyer et al. |

FOREIGN PATENT DOCUMENTS

| | | |
|---|---|---|
| WO | 2009/137335 | 11/2009 |
| WO | 2009/137337 | 11/2009 |
| WO | 2010/024930 | 3/2010 |

OTHER PUBLICATIONS

Dörwald, "Side Reactions in Organic Synthesis: A Guide to Successful Synthesis Design" 2005 Wiley-VCH Verlag GmbH & Co. KGaA, Wienheim, Chapter 1.*
Folkman; Ann. Surg., 1972, 175, 409-416.*
International Preliminary Report on Patentability and Written Opinion, in the English language, issued Apr. 16, 2013 in International Application No. PCT/JP2011/071264.
Aoki et al., "Cortistatins A, B, C, and D, Anti-angiogenic Steroidal Alkaloids, from the Marine Sponge *Corticium simplex*", J. Am. Chem. Soc., vol. 128, 2006, pp. 3148-3149.
Aoki et al., "Cortistatins J, K, L, novel abeo-9(10-19)-androstane-type steroidal alkaloids with isoquinoline unit, from marine sponge *Corticium simplex*", Tetrahedron Letters, vol. 48, 2007, pp. 4485-4488.

Aoki et al., "Structure-activity relationship and biological property of cortistatins, anti-angiogenic spongean steroidal alkaloids", Bioorganic & Medicinal Chemistry, vol. 15, 2007, pp. 6758-6762.

Kotoku et al., "Studies on Structure-Activity Relationship and Action Mechanism of Cortistatins, Anti-angiogenic Compounds derived from Marine Sponge", Abstracts of the 49th Symposium on the chemistry of natural products, 2007, p. 341, with English translation.

Morimoto et al., "Design and Synthesis of Analog Compounds of Anti-angiogenic Compound Cortistatin A", Abstracts of the 130th Annual Meeting of the Pharmaceutical Society of Japan, 29P-pm279, 2010, p. 249, with English translation.

Czako et al., "Discovery of Potent and Practical Antiangiogenic Agents Inspired by Cortistatin A", J. Am. Chem. Soc., vol. 131, 2009, pp. 9014-9019.

Nicolaou et al., "Total Synthesis and Biological Evaluation of Cortistatins A and J and Analogues Thereof", J. Am. Chem. Soc., vol. 131, 2009, pp. 10587-10597.

Sato et al., "Synthesis and Anti-Angiogenic Activity of Cortistatin Analogs", Biosci. Biotechnol. Biochem., vol. 72, 2008, pp. 2992-2997.

International Search Report issued Nov. 22, 2011 in International Application No. PCT/JP2011/071264.

Extended European Search Report issued Jan. 22, 2014 in corresponding Application No. 11 82 5285.7.

Yamashita et al., "A Concise Synthesis of the Pentacyclic Framework of Cortistatins", Journal of Organic Letters, Jul. 2008, vol. 10, No. 16, pp. 3413-3415.

Kotoku et al., "Creation of Readily Accessible and Orally Active Analogue of Cortistatin A", ACS Medicinal Chemistry Letters, Jul. 2012, vol. 3, No. 8, pp. 673-377.

\* cited by examiner

*Primary Examiner* — John Mabry
*Assistant Examiner* — Daniel Carcanague
(74) *Attorney, Agent, or Firm* — Wenderoth, Lind & Ponack, L.L.P.

(57) ABSTRACT

A compound represented by the general formula (M):

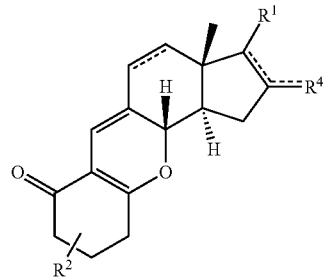

(M)

(wherein $R^1$ represents a substituted or unsubstituted aromatic heterocyclic group, $R^2$ represents a hydrogen atom, a substituted or unsubstituted alkyl group having 1 to 3 carbon atoms, $OR^3$, $N(R^3)_2$, $C(=O)OR^3$ or $C(=O)N(R^3)_2$, $R^3$ represents a hydrogen atom, an alkyl group having 1 to 4 carbon atoms, or an acyl group having 1 to 4 carbon atoms, $R^4$ represents a hydrogen atom, an oxygen atom or $OR^5$, and $R^5$ represents a hydrogen atom, an alkyl group having 1 to 3 carbon atoms, or an acyl group having 1 to 3 carbon atoms); or a pharmaceutically acceptable salt thereof is a cortistatin A analog which is useful as an active ingredient of medicaments for cancer prevention or treatment in that the analog can be mass-produced by chemical synthesis due to its simple chemical structure and retains the same biological activities as those of cortistatin A.

7 Claims, 12 Drawing Sheets

Negative control (bFGF-)

Positive control (bFGF+)

CA-1 (10 mg/kg) (bFGF+)

CA-1 (25 mg/kg) (bFGF+)

Negative control
bFGF (−)

Positive control
bFGF (+)

bFGF (+)
+ CA-1 (10 mg/kg)

bFGF (+)
+ CA-1 (50 mg/kg)

CORTISTATIN A ANALOG AND USE THEREOF

TECHNICAL FIELD

The present invention relates to a novel cortistatin A analog and use thereof. More particularly, the present invention relates to a novel cortistatin A analog which is useful for cancer prevention or treatment in that the analog anti-proliferative activity against vascular endothelial cells and anti-angiogenic activity.

BACKGROUND ART

Cancer combat is a great challenge for human beings this end, cancer chemotherapeutic drugs have been vigorously developed, but no drugs that have cancer cell-specific effects have been created yet. Angiogenesis in cancer is essential for growth and metastasis of solid cancer. The development of angiogenesis inhibitors for cancer therapy is different in direction from the conventional anticancer drug development based on direct actions on cancer cells. Angiogenesis inhibitors for cancer affect the unique microenvironment surrounding tumor cells, and therefore are expected to reduce the development of drug-resistant cancer cells and to enhance the specificity of effects on cancer cells. Based on such a concept, the following drugs have been created: bevacizumab (trade name: Avastin), a monoclonal antibody inhibiting the binding of a proangiogenic factor VEGF (vascular endothelial growth factor) to its receptor; and sorafenib (trade name: Nexavar) and sunitinib (trade name: Sutent), which inhibit tyrosine kinase receptors including VEGF receptor. These three drugs are clinically used, but have problems in terms of limited indication, side effects, etc. Further, considering that all these drugs have the same action mechanism relevant to inhibition of VEGF signal transduction, it is a quite crucial issue to create novel pharmaceuticals which are different in chemical structure and action mechanism from these drugs.

Under such circumstances, the present inventors focused on vascular endothelial cells, a key player in cancer angiogenesis, and screened for natural substances having selective anti-proliferative activity against vascular endothelial cells. As a result, the present inventors found that the methanol extract from *Corticium simplex*, an Indonesian marine sponge, has specific anti-proliferative activity against human umbilical vein endothelial cells (HUVEC). Then, with the guidance of bioassay, the present inventors purified active substances from the methanol extract, analyzed their chemical structures, identified four kinds of novel modified steroidal alkaloids having an oxabicyclo[3.2.1]octene moiety and an isoquinoline side-chain, and named these steroidal alkaloids as cortistatins. The present inventors confirmed that, in particular, cortistatin A, which is represented by the formula below, shows more than 3000 times stronger anti-proliferative activity against HUVEC ($IC_{50}$=1.8 nM) than against other cancer cells, and inhibits the migration and tubulogenesis of HUVEC, which are regarded as essential indicators of angiogenesis; and in addition, demonstrated that the mechanism of such actions is not relevant to inhibition of VEGF signal transduction (see Non Patent Literature 1 to 3).

[Formula 1]

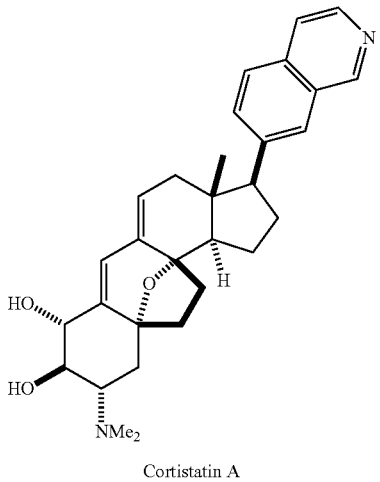

Cortistatin A

However, cortistatins can be obtained in only very small amounts from natural sources, and the industrial production of cortistatins by chemical synthesis is difficult cue to their complicated chemical structures. Therefore, novel cortistatin analogs which can be mass-produced are desired.

Known analogs of cortistatin A include, for example, those described in Patent Literature 1 to 3. However, these analogs have a chemical structure as complicated as that of cortistatin A and require multiple steps for synthesis, and thus are not suitable for industrial mass-production.

CITATION LIST

Patent Literature

Patent Literature 1: WO 2010/024930
Patent Literature 2: WO 2009/137337
Patent Literature 3: WO 2009/137335

Non Patent Literature

Non Patent Literature 1:
Aoki, S., et. al. J. Am. Chem. Soc. 2006, 128, 3148-3149.
Non Patent Literature 2:
Aoki, S., et. al. Tetrahedron Lett. 2007, 48, 485-4488.
Non Patent Literature 3:
Aoki, S., et al. Bioorg. Med. Chem. 2007, 15, 6758-6762.

SUMMARY OF INVENTION

Technical Problem

An object of the present invention is to provide a cortistatin A analog which can be mass-produced by chemical synthesis due to its simple chemical structure and retains the same biological activities as those of cortistatin A; and to provide a medicament for cancer prevention or treatment comprising the cortistatin A analog as an active ingredient.

Solution to Problem

The present invention includes the following as a solution to the above-mentioned problems.

(1) A compound represented by the general formula (M):

[Formula 2]

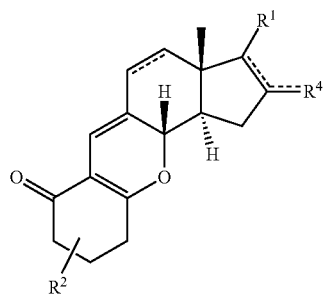

(M)

(wherein $R^1$ represents a substituted or unsubstituted aromatic heterocyclic group, $R^2$ represents a hydrogen atom, a substituted or unsubstituted alkyl group having 1 to 3 carbon atoms, $OR^2$, $N(R^3)_2$, $C(=O)OR^3$ or $C(=O)N(R^3)_2$, $R^3$ represents a hydrogen atom, an alkyl group having 1 to 4 carbon atoms, or an acyl group having 1 to 4 carbon atoms, $R^4$ represents a hydrogen atom, an oxygen atom or $OR^5$, and $R^5$ represents a hydrogen atom, an alkyl group having 1 to 3 carbon atoms, or an acyl group having 1 to 3 carbon atoms); or a pharmaceutically acceptable salt thereof.

(2) A compound represented by the general formula (I)

[Formula 3]

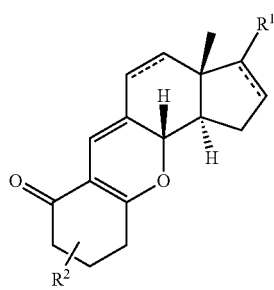

(I)

(wherein $R^1$ represents a substituted or unsubstituted aromatic heterocyclic group, $R^2$ represents a hydrogen atom, a substituted or unsubstituted alkyl group having 1 to 3 carbon atoms, $OR^3$, $N(R^3)_2$, $C(=O)OR^3$ or $C(=O)N(R^3)_2$, and $R^3$ represents a hydrogen atom, an alkyl group having 1 to 4 carbon atoms, or an acyl group having 1 to 4 carbon atoms); or a pharmaceutically acceptable salt thereof.

(3) The compound according to the above (1) or (2), wherein $R^1$ is a pyridyl group, a quinolyl group or an isoquinolyl group; or a pharmaceutically acceptable salt thereof.

(4) The compound according to the above (3), which is represented by

Formula (II):

[Formula 4]

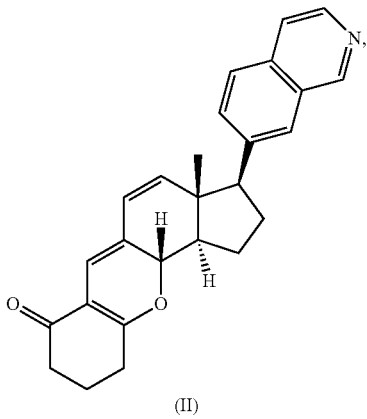

(II)

Formula (XVIII):

[Formula 5]

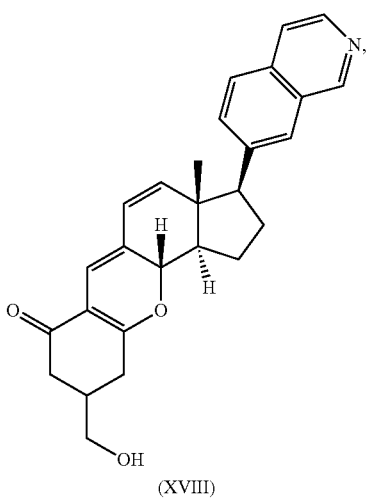

(XVIII)

Formula (XIX):

[Formula 6]

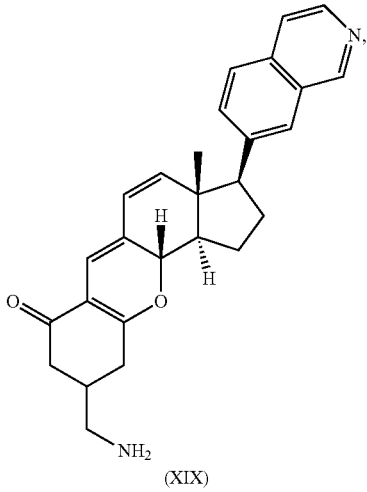

(XIX)

Formula (XXIII):

[Formula 7]

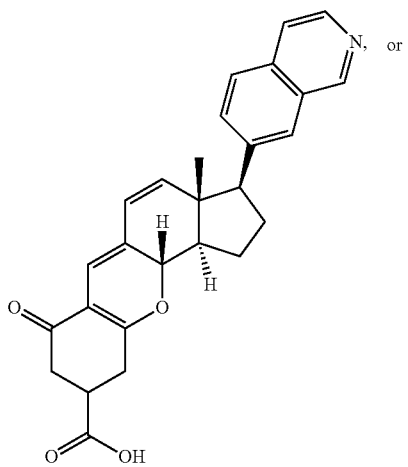

(XXIII)

Formula (LIV):

[Formula 8]

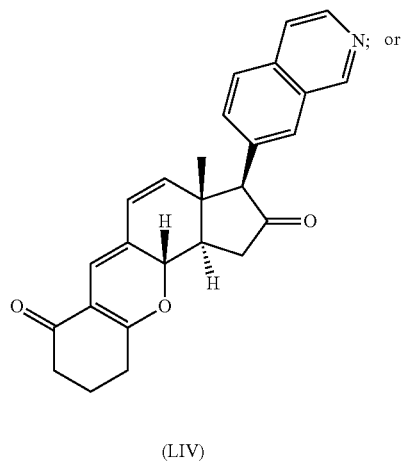

(LIV)

a pharmaceutically acceptable salt thereof.

(5) A pharmaceutical composition, comprising the compound according to any one of the above (1) to (4) or a pharmaceutically acceptable salt thereof, and a pharmaceutically acceptable carrier.

(6) A vascular endothelial cell growth inhibitor, comprising the compound according to any one of the above (1) to (4) or a pharmaceutically acceptable salt thereof as an active ingredient.

(7) An angiogenesis inhibitor, comprising the compound according to any one of the above (1) to (4) or a pharmaceutically acceptable salt thereof as an active ingredient.

(8) A medicament for cancer prevention or treatment, comprising the compound according to any one of the above (1) to (4) or a pharmaceutically acceptable salt thereof as an active ingredient.

(9) The medicament according to the above (8), which is usable in combination with a chemotherapeutic drug, an immunotherapeutic drug or a hormone therapy drug.

(10) The medicament according to the above (8), which is usable in combination with radiotherapy.

(11) A method for cancer prevention or treatment, the method comprising administering, to a mammal, an effective amount of the compound according to any one of the above (1) to (4) or a pharmaceutically acceptable salt thereof.

(12) Use of the compound according to any one of the above (1) to (4) or a pharmaceutically acceptable salt thereof for production of medicaments for cancer prevention or treatment.

(13) The compound according to any one of the above (1) to (4) or a pharmaceutically acceptable salt thereof for use in cancer treatment or prevention.

Advantageous Effects of Invention

The compound represented by the general formula (M) or (I) of the present invention or a pharmaceutically acceptable salt thereof has a simpler chemical structure than that of cortistatin A, and therefore can be mass-produced by chemical synthesis. The compound represented by the general formula (M) or (I) of the present invention or a pharmaceutically acceptable salt thereof retains the same biological activities as those of cortistatin A, namely, selective anti-proliferative activity against vascular endothelial cells and anti-angiogenic activity, and therefore is useful as an active ingredient of medicaments for cancer prevention or treatment.

DESCRIPTION OF EMBODIMENTS

Figure 1:
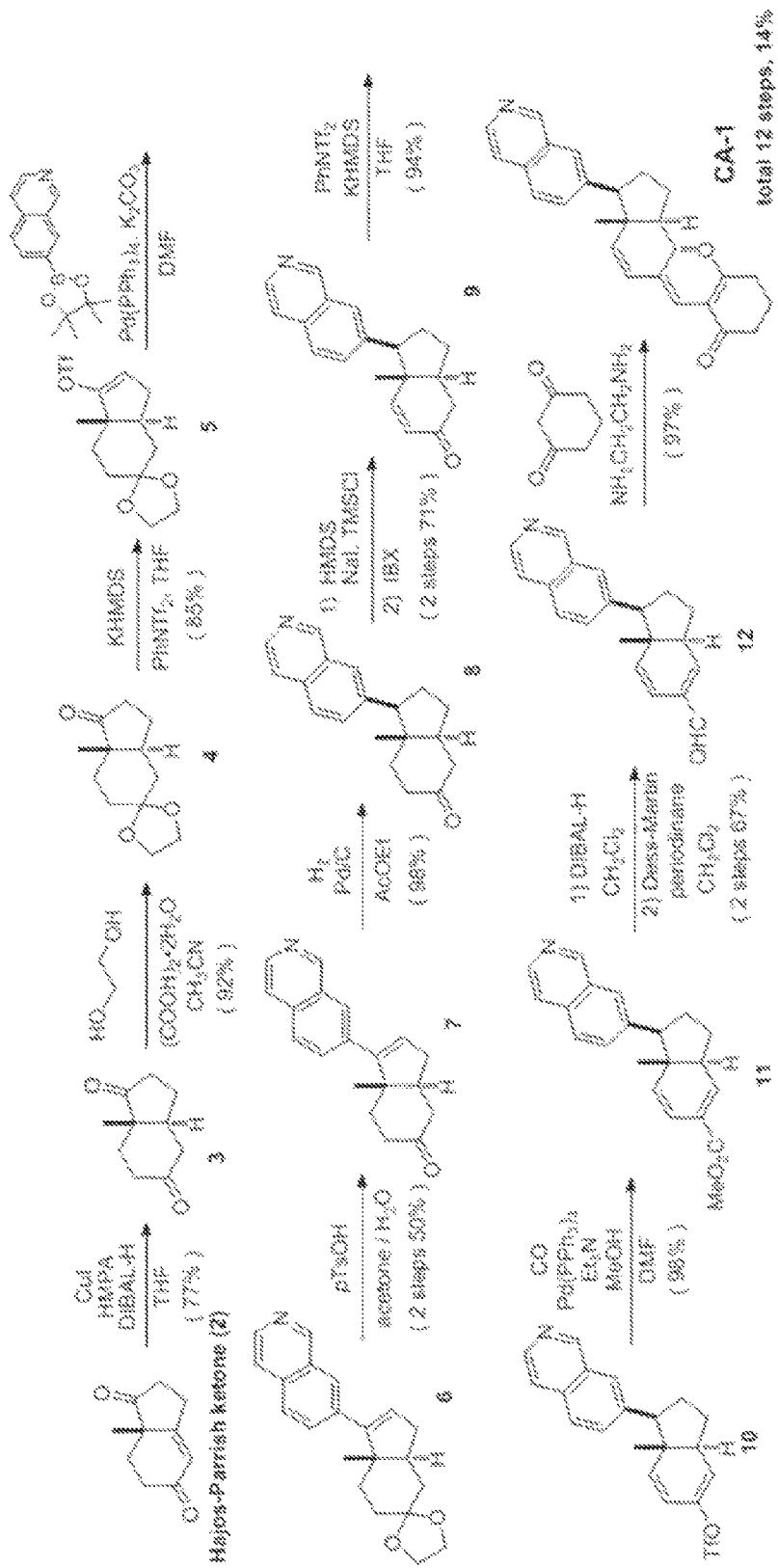
FIG. 1 shows the synthesis scheme of the compound represented by formula (II) (CA-1).

The present invention provides a compound represented by the general formula (M):

[Formula 9]

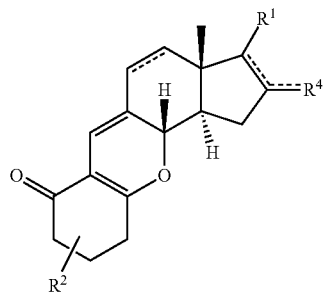

(wherein $R^1$ represents a substituted or unsubstituted aromatic heterocyclic group, $R^2$ represents a hydrogen atom, a substituted or unsubstituted alkyl group having 1 to 3 carbon atoms, $OR^3$, $N(R^3)_2$, $C(=O)OR^3$ or $C(=O)N(R^3)_2$, $R^3$ represents a hydrogen atom, an alkyl group having 1 to 4 carbon atoms, or an acyl group having 1 to 4 carbon atoms, $R^4$ represents a hydrogen atom, an oxygen atom or $OR^5$, and $R^5$ represents a hydrogen atom, an alkyl group having 1 to 3 carbon atoms, or an acyl group having 1 to 3 carbon atoms); or a pharmaceutically acceptable salt thereof.

The present invention also provides a compound represented by the general formula (I)

[Formula 10]

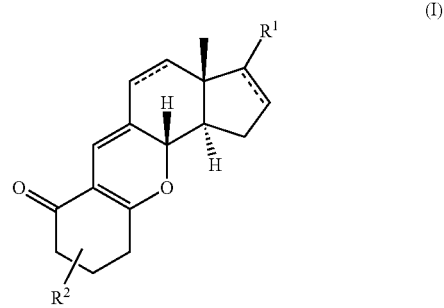

(wherein $R^1$ represents a substituted or unsubstituted aromatic heterocyclic group, $R^2$ represents a hydrogen atom, a substituted or unsubstituted alkyl group having 1 to 3 carbon atoms, $OR^3$, $N(R^3)_2$, $C(=O)OR^3$ or $C(=O)N(R^3)_2$, and $R^3$ represents a hydrogen atom, an alkyl group having 1 to 4 carbon atoms, or an acyl group having 1 to 4 carbon atoms); or a pharmaceutically acceptable salt thereof.

As for $R^1$, the "substituted or unsubstituted aromatic heterocyclic group" refers to a 5- or 6-membered ring group which contains, as a ring atom, at least one heteroatom such as a nitrogen atom, a sulfur atom and an oxygen atom, is optionally condensed with a benzene ring and optionally has one or more substituents selected from various kinds of groups on a ring atom. Examples of the substituted or unsubstituted aromatic heterocyclic group include pyridyl, furyl, thienyl, indolyl, quinolyl, isoquinolyl, benzofuranyl, benzothienyl, imidazolyl, benzimidazolyl, thiazolyl, oxazolyl, pyrazolyl, pyrimidyl, pyrazinyl, isoxazolyl, isoindolyl and pyrrolyl groups. Preferred is a pyridyl group, a quinolyl group or an isoquinolyl group, and more preferred is a 7-isoquinolyl group.

Examples of the substituent include a fluorine atom, a chlorine atom, a cyano group, a hydroxyl group, a nitro group, an alkyl group, a cycloalkyl group, an alkoxy group, an amino group, a phenyl group, a naphthyl group, an anthryl group, a styryl group, a pyridyl group, a pyridoindolyl group, a quinolyl group and a benzothiazolyl group. These substituents may also be substituted.

As for $R^2$, the "substituted or unsubstituted alkyl group having 1 to 3 carbon atoms" is, for example, a methyl, ethyl, n-propyl or isopropyl group optionally having one or more substituents. Examples of the substituent include those listed above.

As for $R^3$, examples of the "alkyl group having 1 to 4 carbon atoms" include a methyl group, an ethyl group, a n-propyl group, an isopropyl group, a n-butyl group, an isobutyl group, a sec-butyl group and a tert-butyl group; and examples of the "acyl group having 1 to 4 carbon atoms" include a formyl group, an acetyl group, a propionyl group and a butyryl group.

As for $R^5$, examples of the "alkyl group haying 1 to 3 carbon atoms" include a methyl group, an ethyl group, a n-propyl group and an isopropyl group; and examples of the "acyl group having 1 to 3 carbon atoms" include a formyl group, an acetyl group, a propionyl group and a malonyl group.

Examples of the compound represented by the general formula (M) or (I) of the present invention include the following compounds (II) to (CCXLV).
[Formula 11]
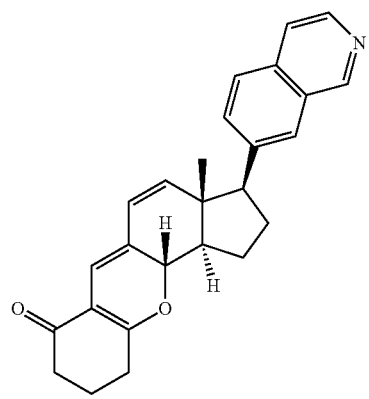
(II)
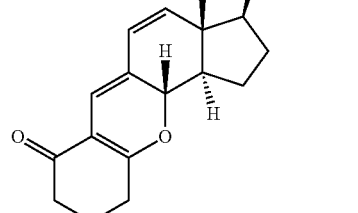
(III)
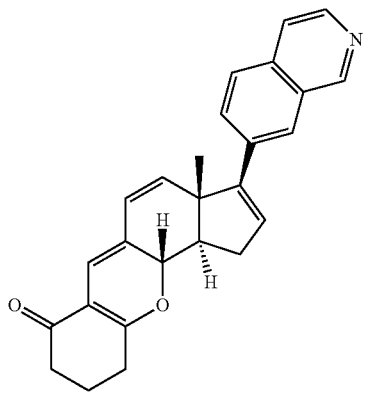
(IV)
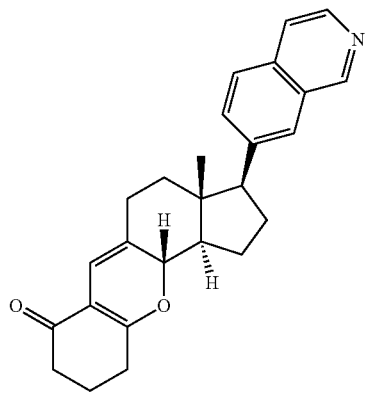
(V)
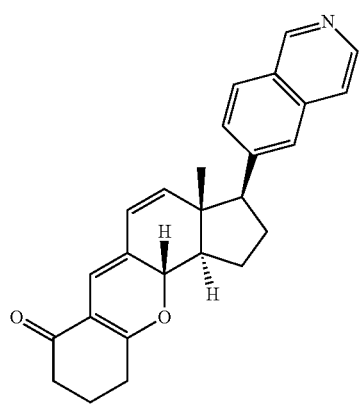
(VI)
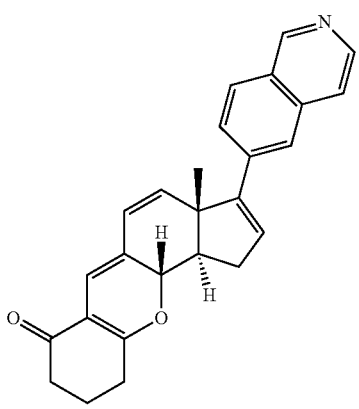
(VII)
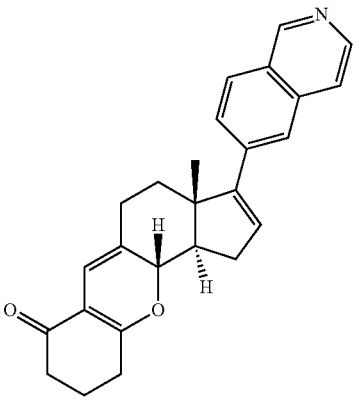
(VIII)

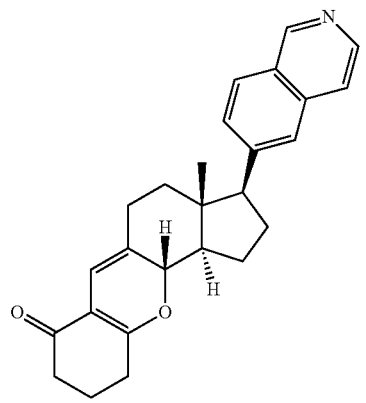 (IX)
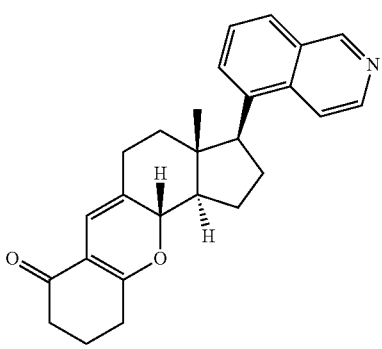 (XIII)
[Formula 12]
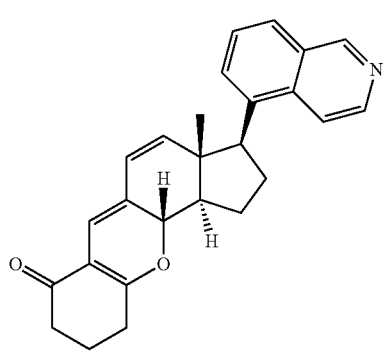 (X)
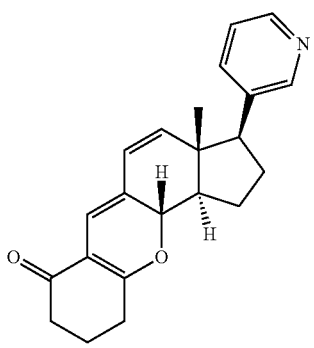 (XIV)
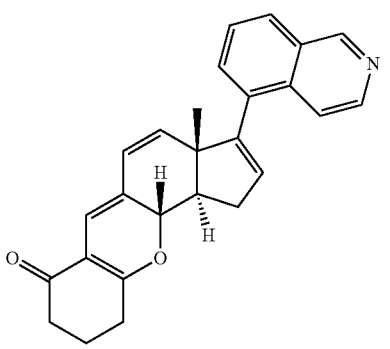 (XI)
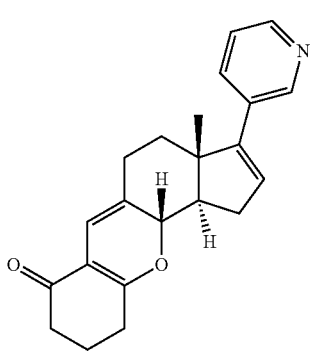 (XV)
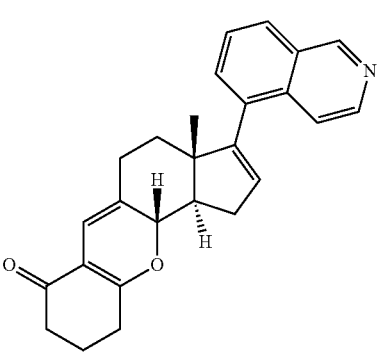 (XII)
(XVI)

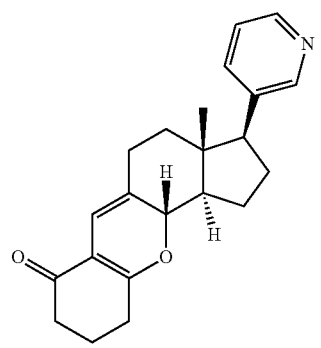
(XVII)
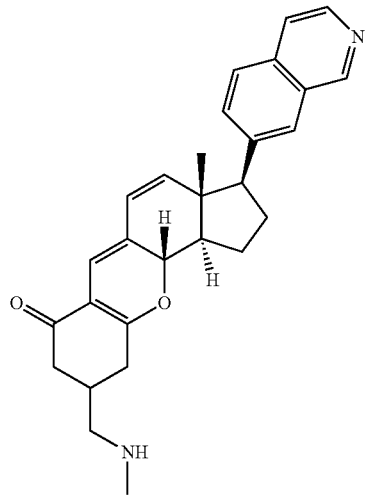
(XX)
(XVIII)
(XXI)
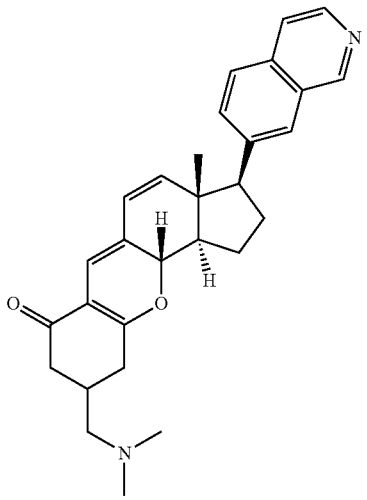
(XIX)
(XXII)
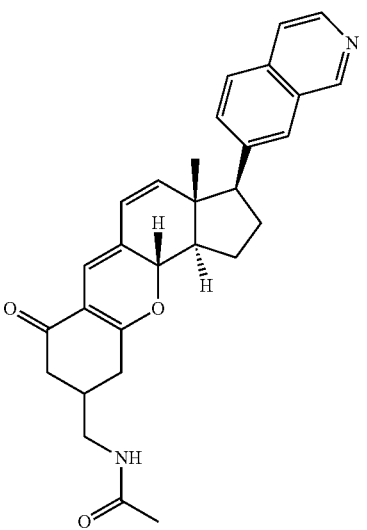

(XXIII)
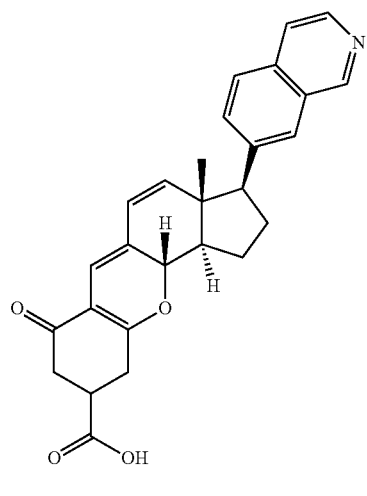
(XXIV)
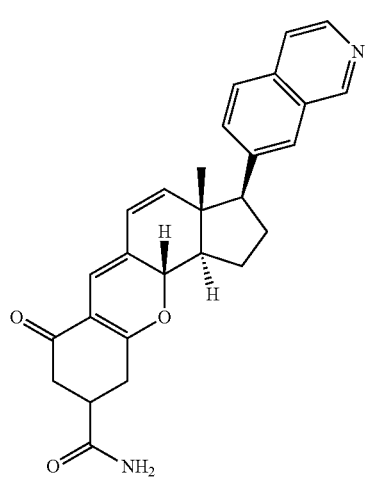
(XXV)
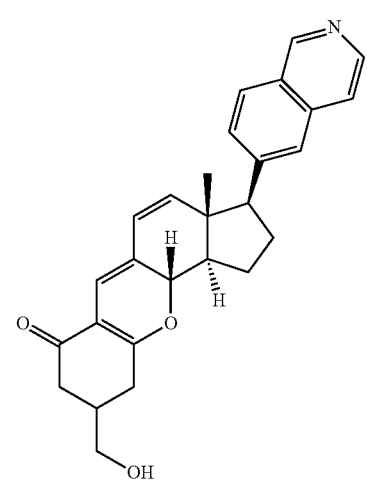
(XXVI)
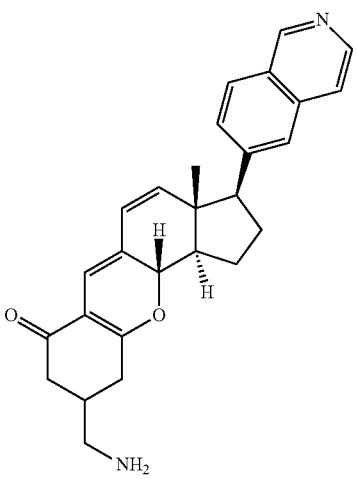
(XXVII)
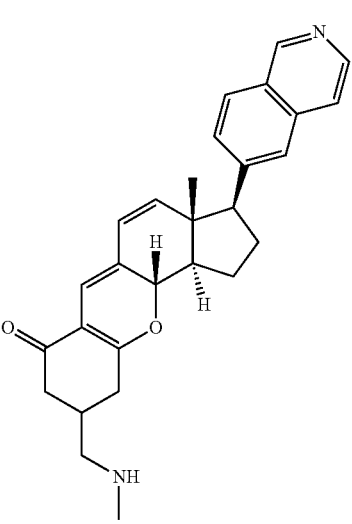
(XXVIII)
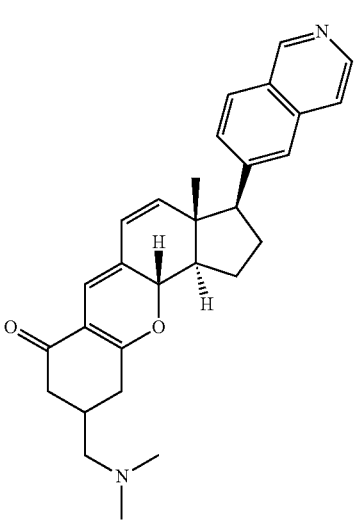

17
-continued
(XXIX)
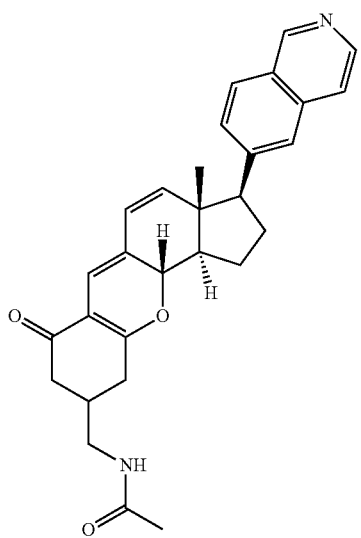
(XXX)
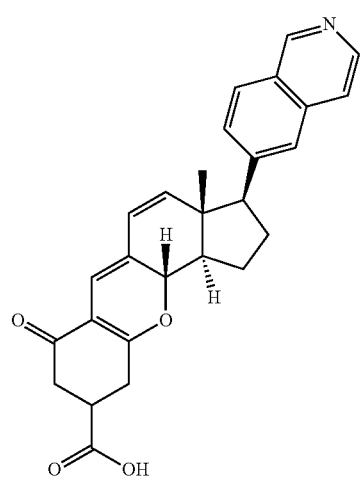
(XXXI)
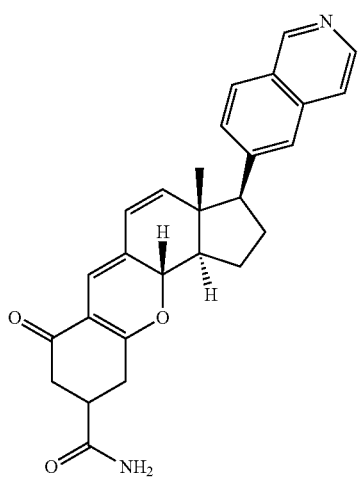
18
-continued
(XXXII)
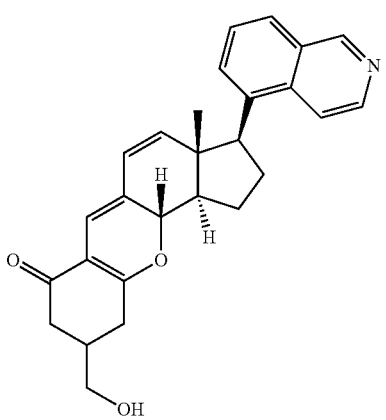
(XXXIII)
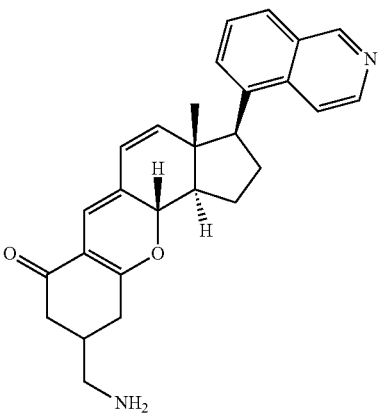
(XXXIV)
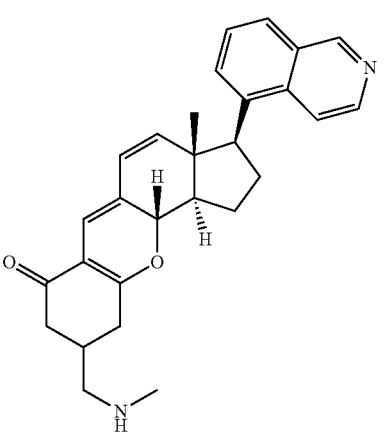

(XXXV)
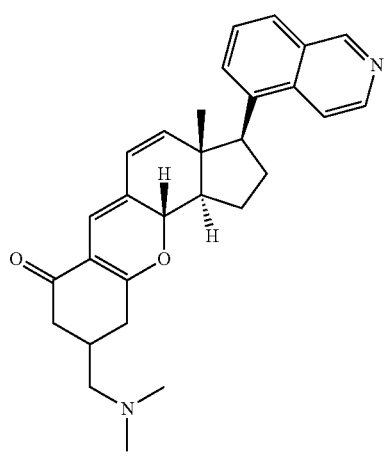
(XXXVIII)
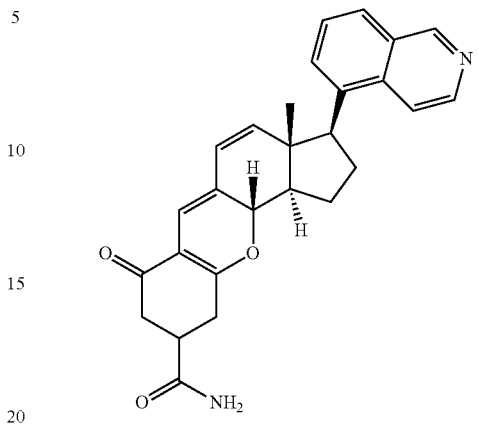
(XXXVI)
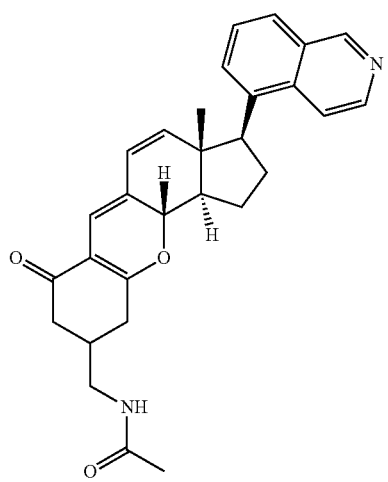
(XXXIX)
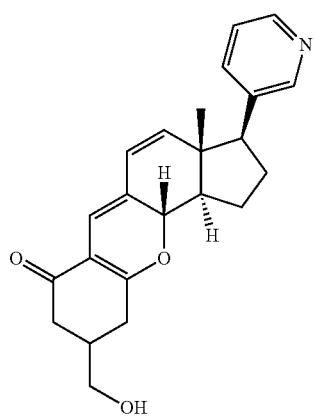
(XXXVII)
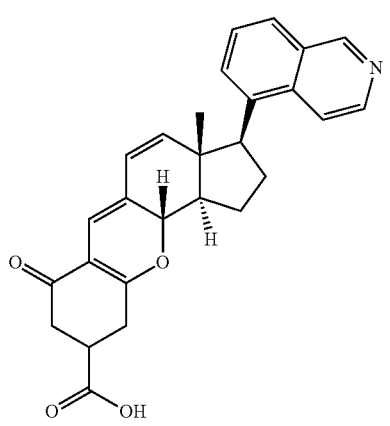
(XL)
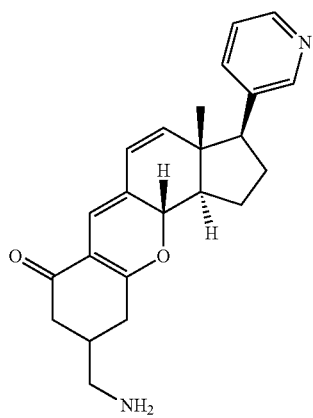

(XLI)
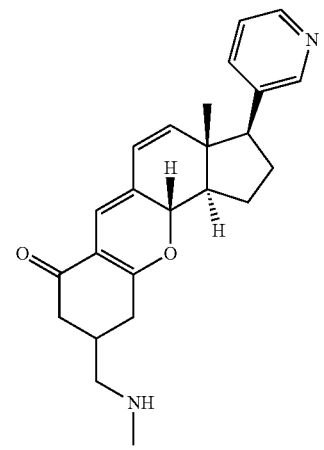
(XLII)
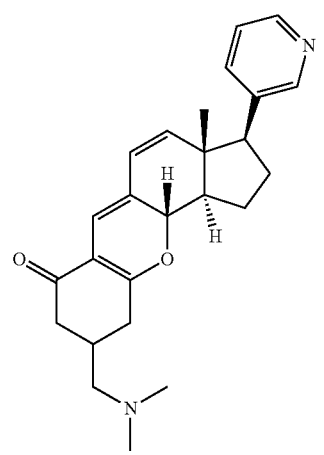
(XLIII)
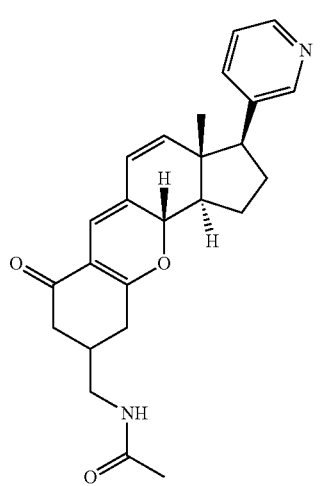
(XLIV)
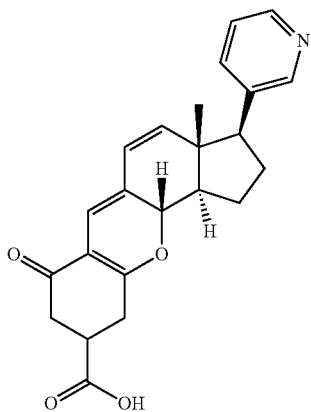
(XLV)
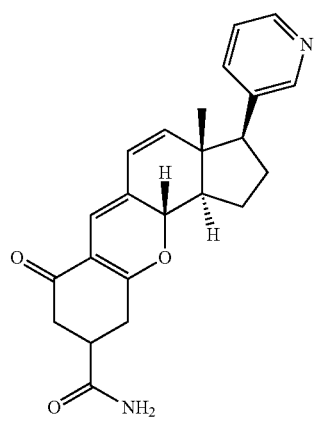
(XLVI)
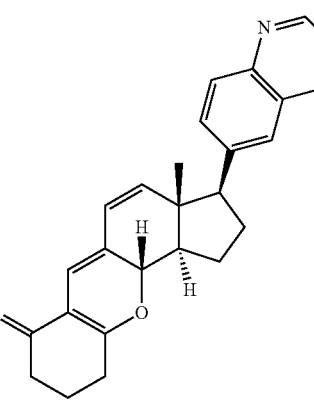
(XLVII)
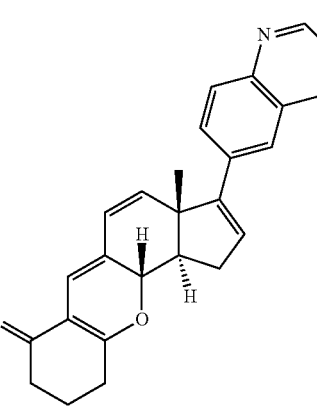

(XLVIII)
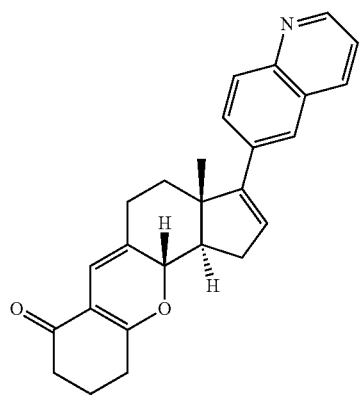
(XLIX)
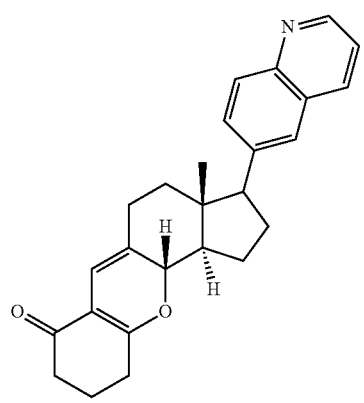
[Formula 15]
(L)
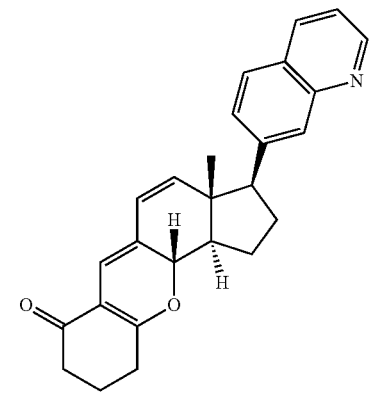
(LI)
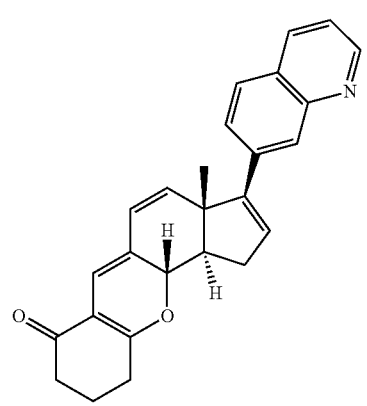
(LII)
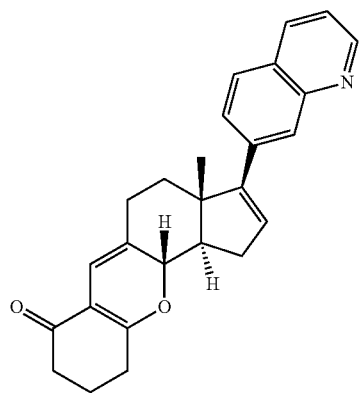
(LIII)
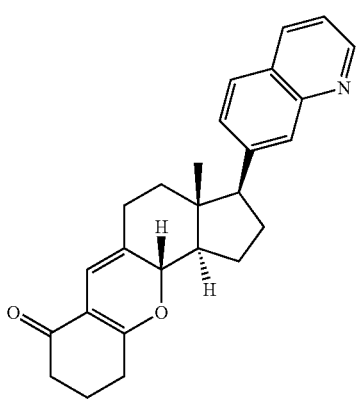
[Formula 16]
(LIV)
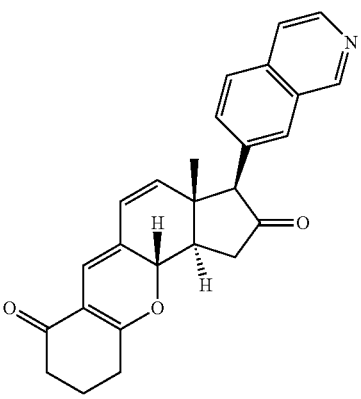
(LV)
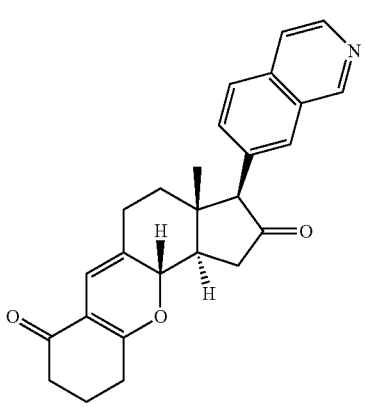

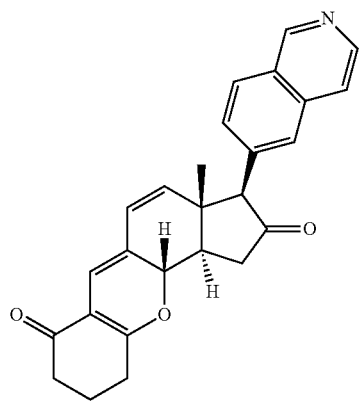
(LVI)
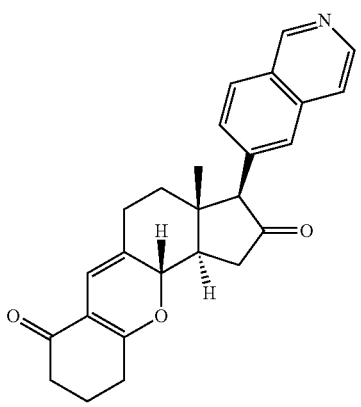
(LVII)
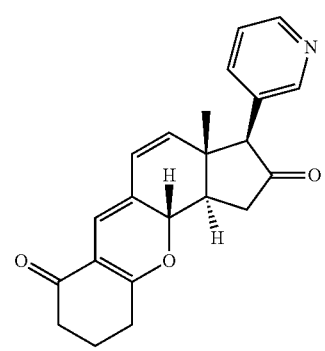
(LVIII)
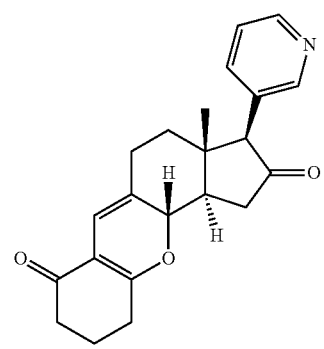
(LIX)
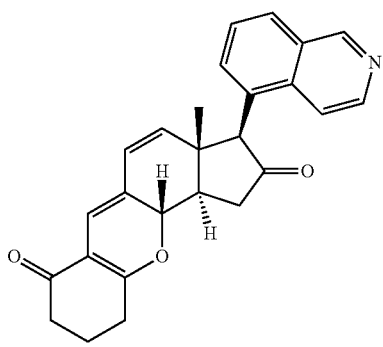
(LX)
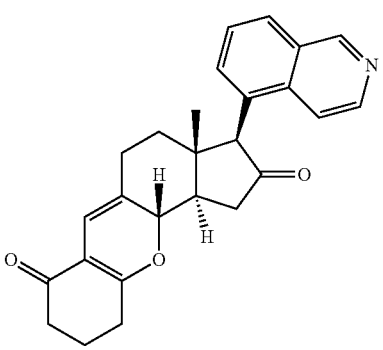
(LXI)
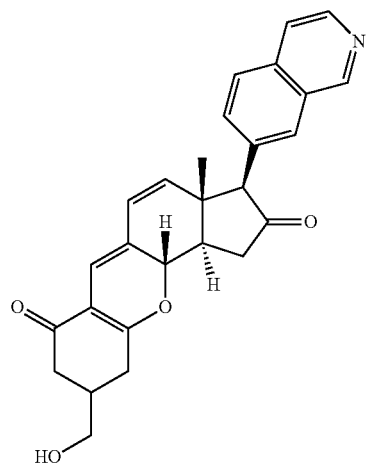
(LXII)
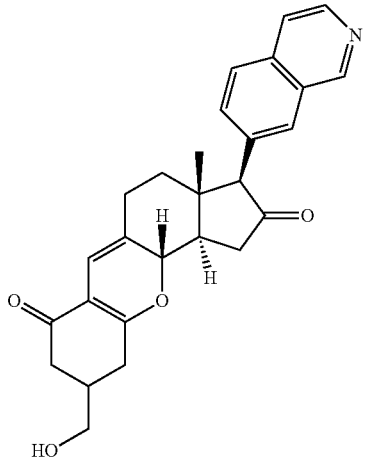
(LXIII)

(LXIV)
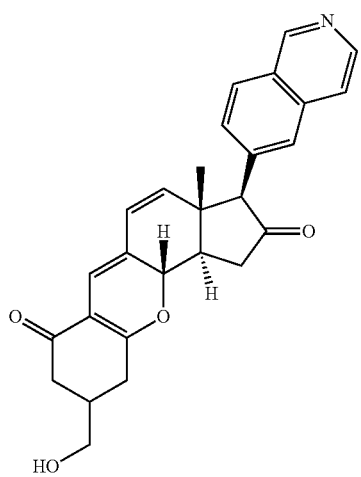
(LXV)
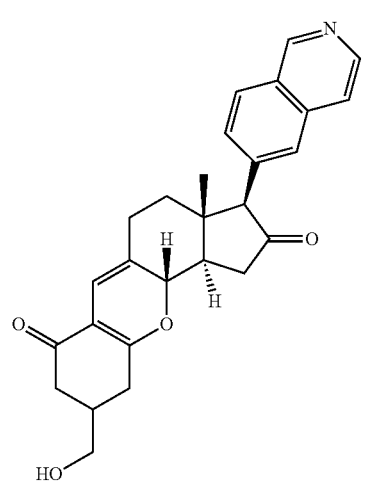
[Formula 17]
(LXVI)
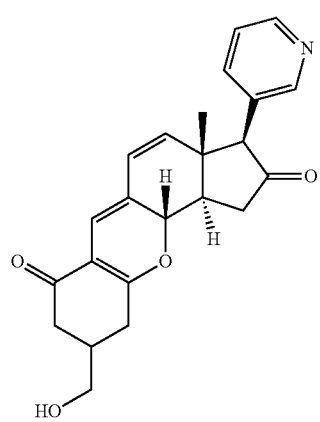
(LXVII)
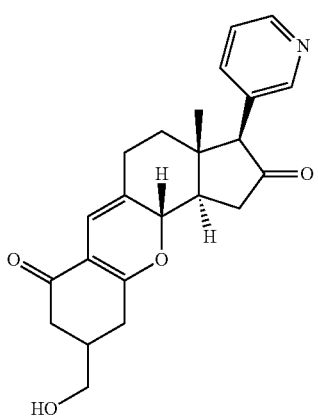
(LXVIII)
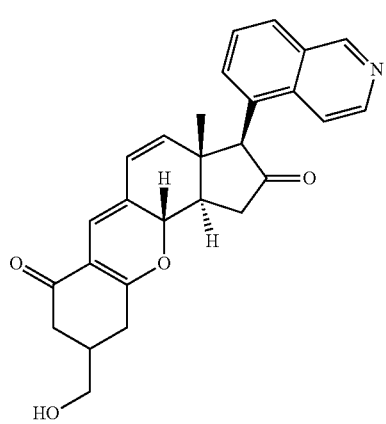
(LXIX)
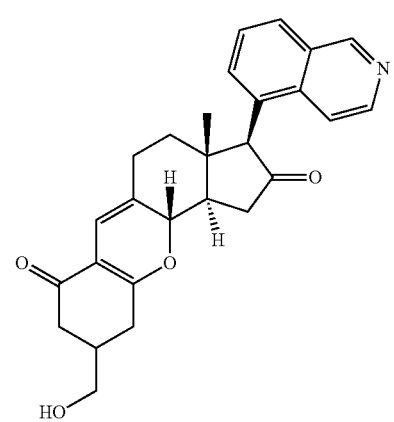

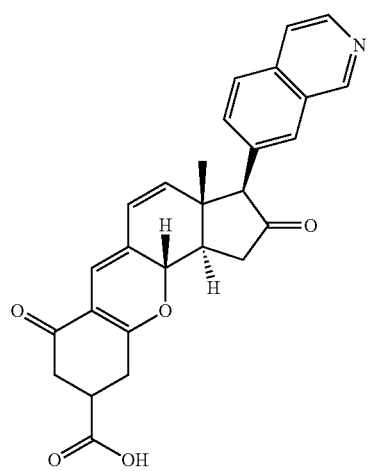
(LXX)
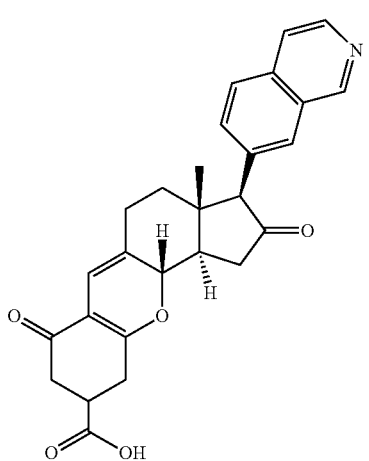
(LXXI)
(LXXII)
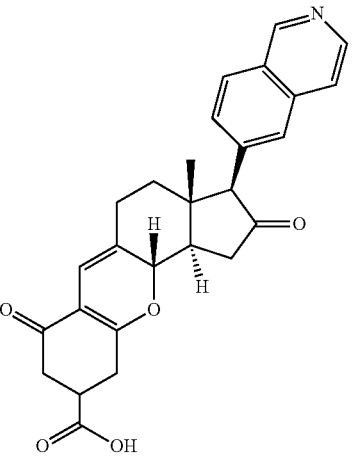
(LXXIII)
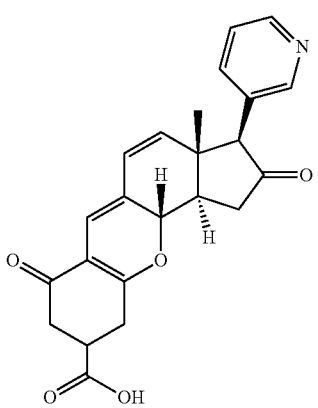
(LXXIV)
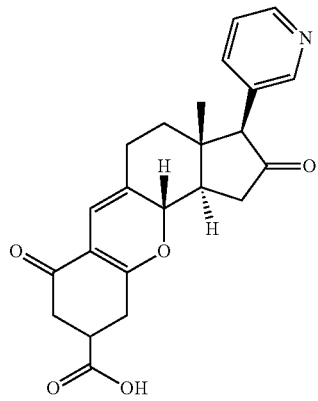
(LXXV)
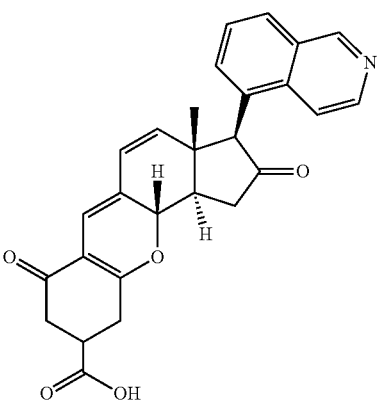
(LXXVI)

-continued
(LXXVII)
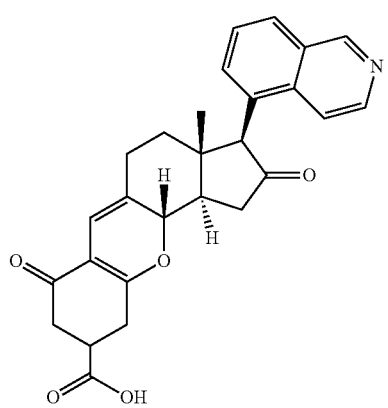
[Formula 18]
(LXXVIII)
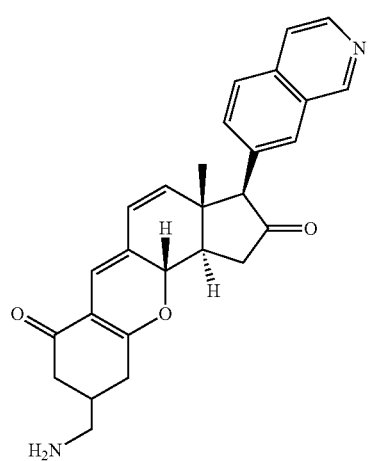
(LXXIX)
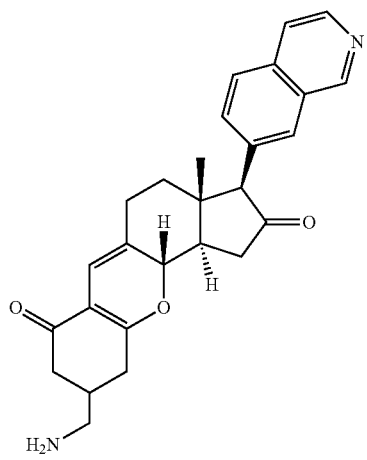
-continued
(LXXX)
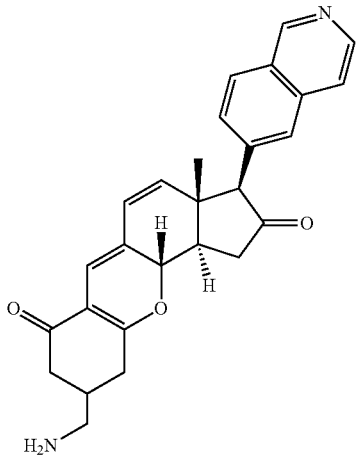
(LXXXI)
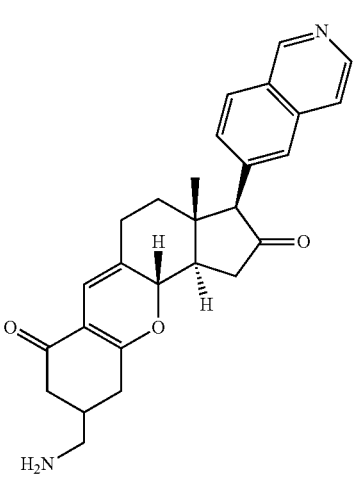
(LXXXII)
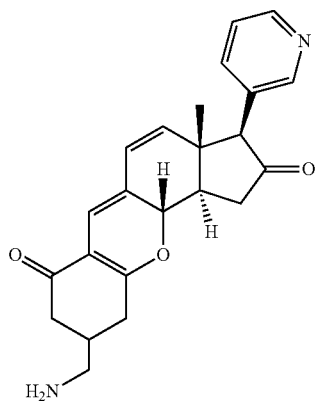

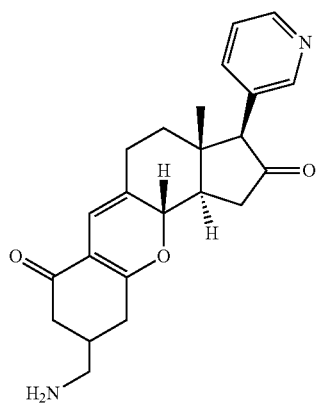
(LXXXIII)
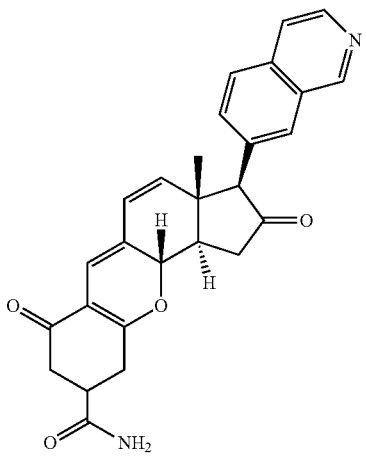
(LXXXVI)
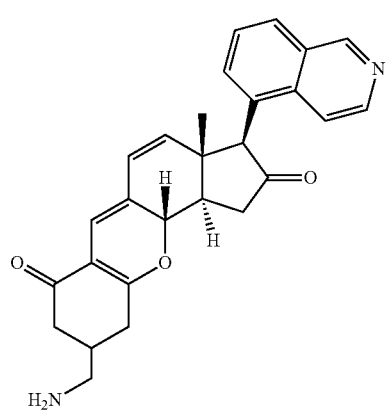
(LXXXIV)
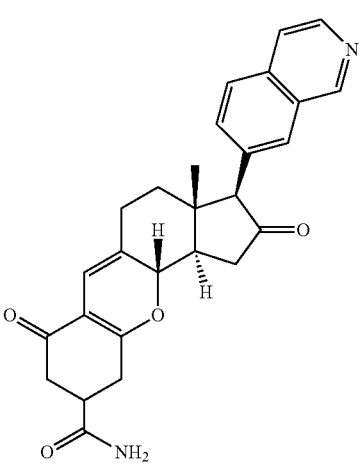
(LXXXVII)
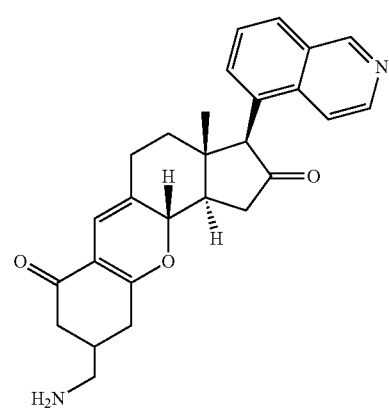
(LXXXV)
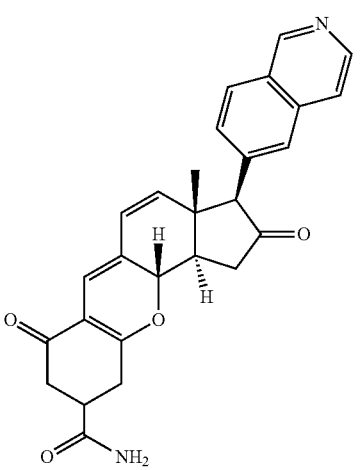
(LXXXVIII)

(LXXXIX)
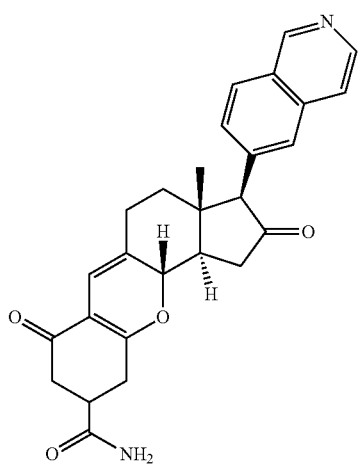
[Formula 19]
(XC)
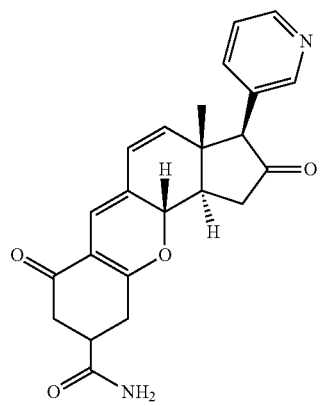
(XCI)
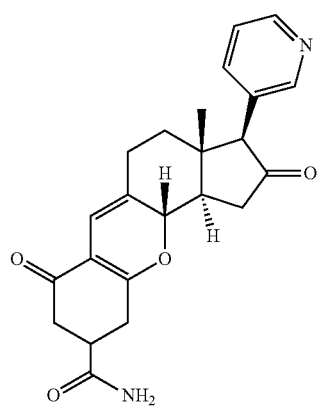
(XCII)
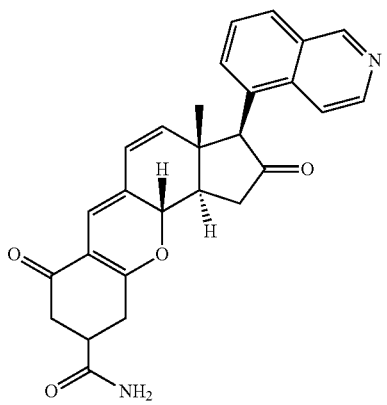
(XCIII)
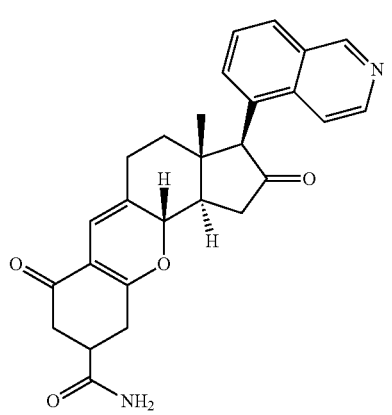
(XCIV)
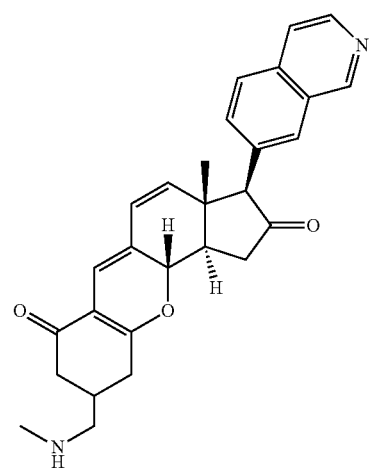

(XCV)
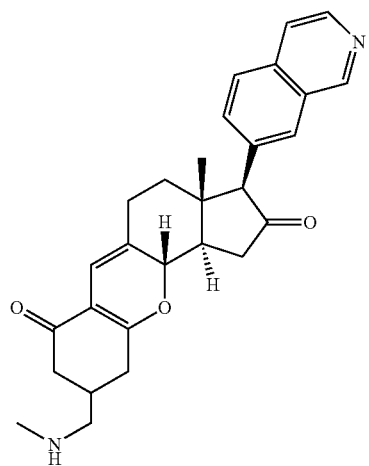
(XCVI)
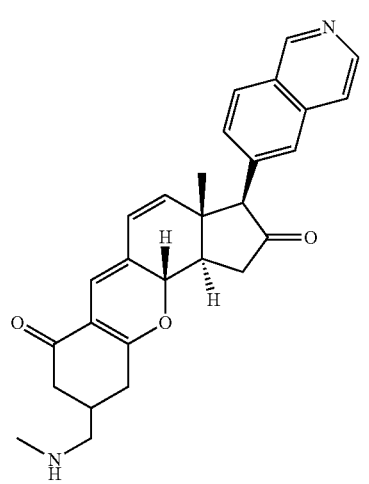
(XCVII)
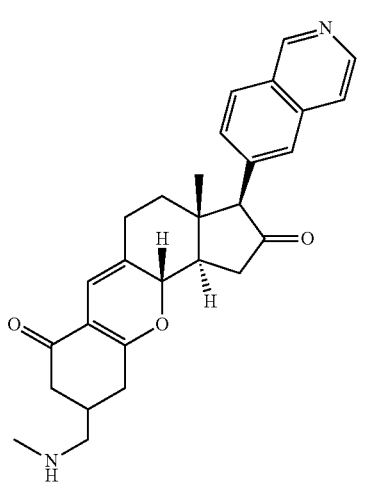
(XCVIII)
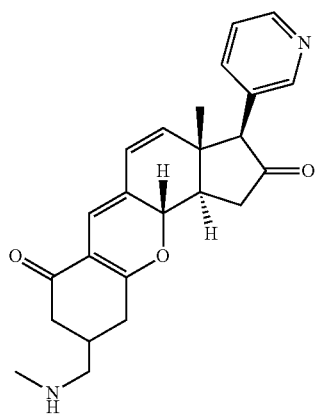
(XCIX)
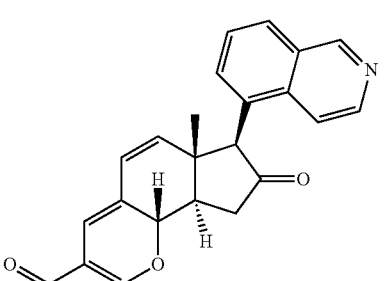
(C)
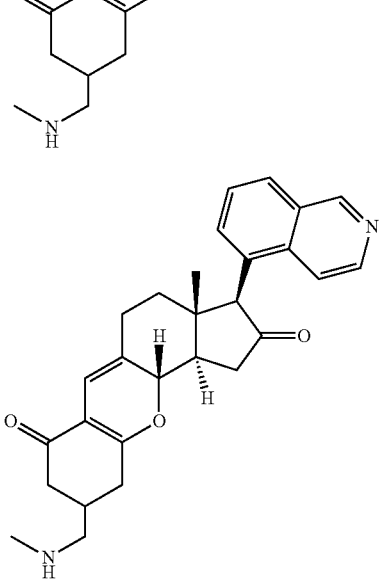
(CI)

[Formula 20]
(CII)
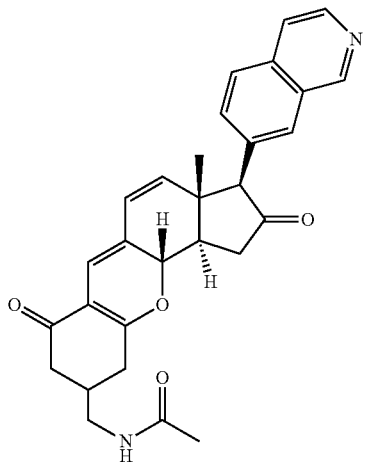
(CIII)
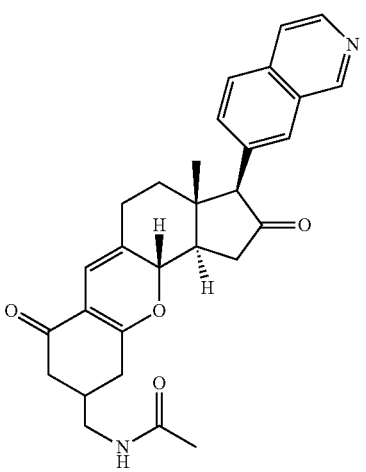
(CIV)
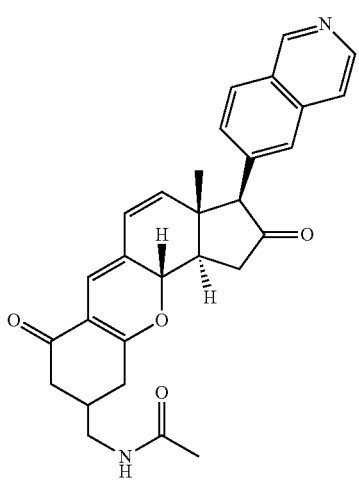
(CV)
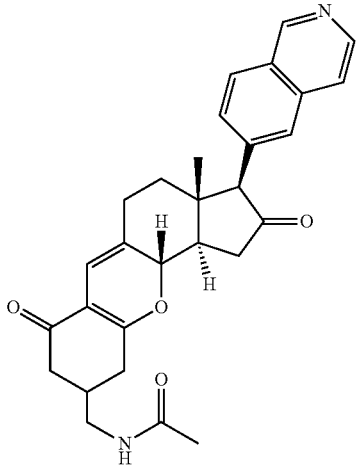
(CVI)
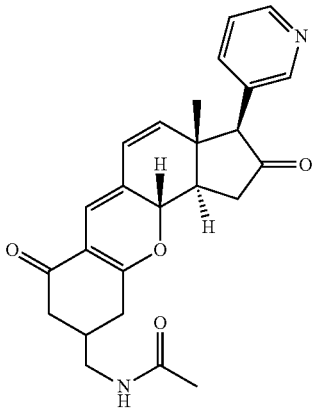
(CVII)
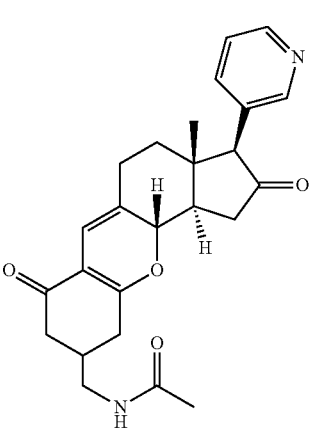

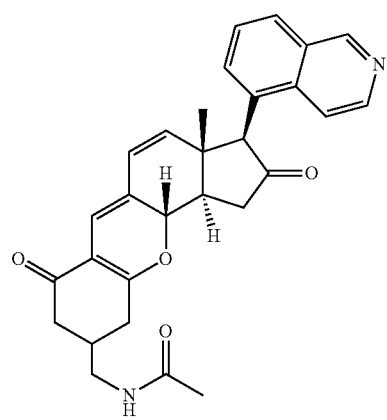
(CVIII)
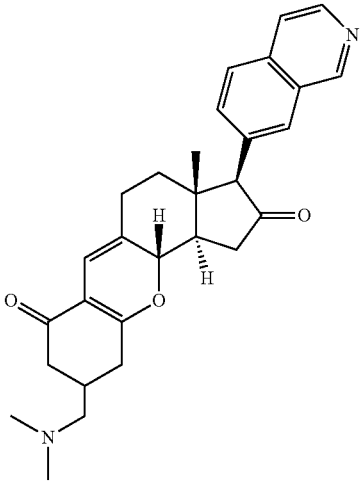
(CXI)
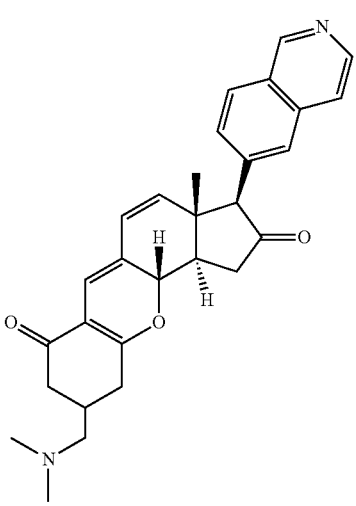
(CXII)
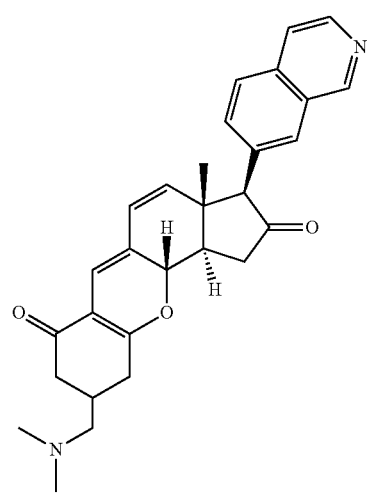
(CX)
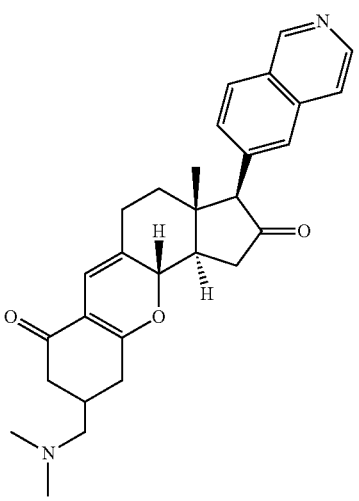
(CXIII)

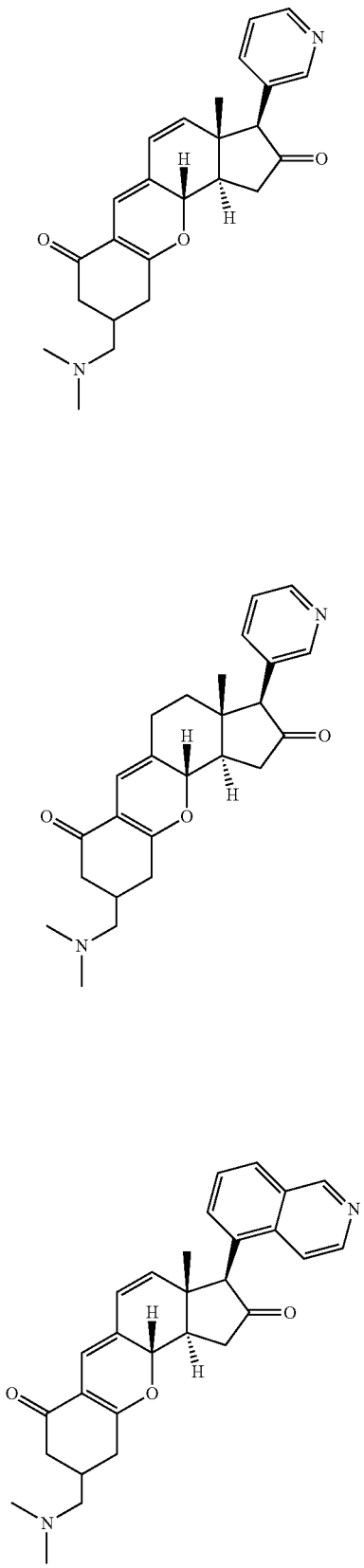
(CXIV)
(CXV)
(CXVI)
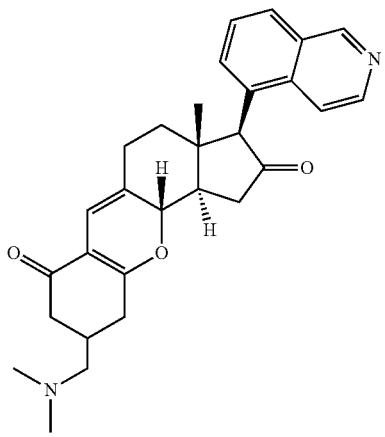
(CXVII)
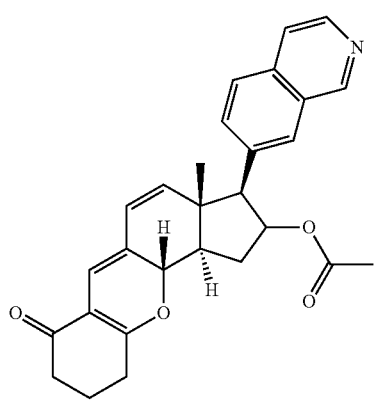
(CXVIII)
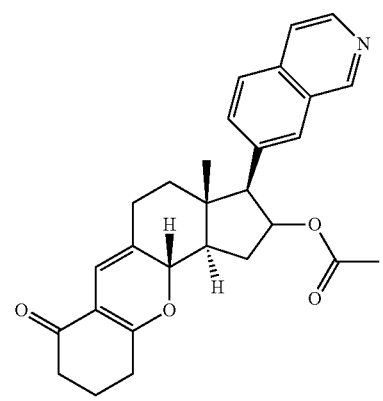
(CXIX)
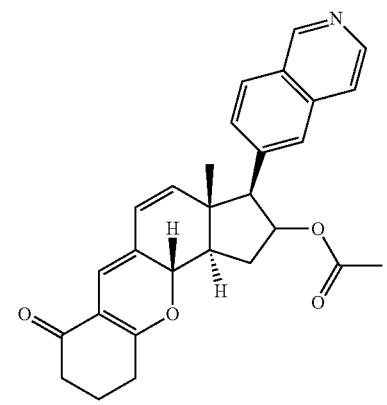
(CXX)

-continued
(CXXI)
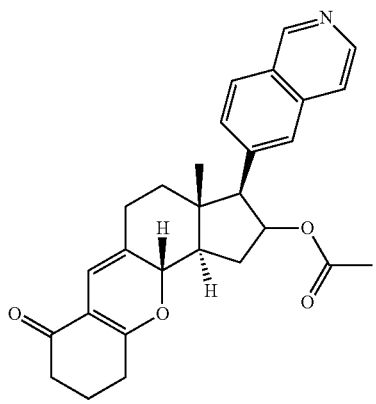
(CXXII)
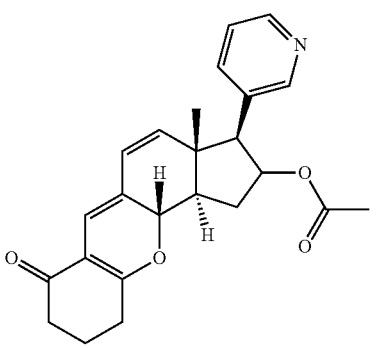
(CXXIII)
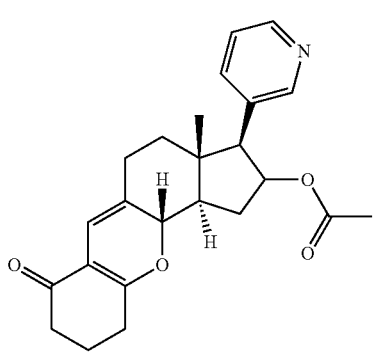
(CXXIV)
(CXXV)
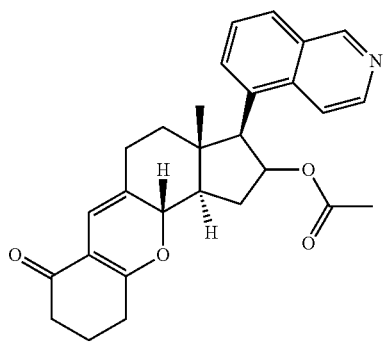
[Formula 22]
(CXXVI)
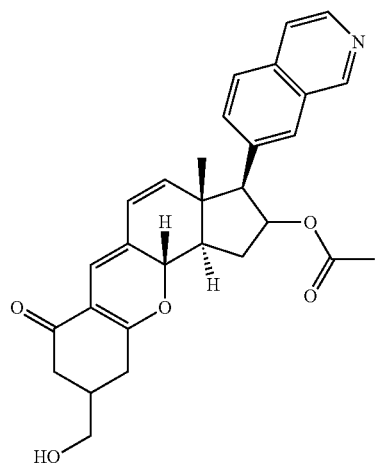
(CXXVII)
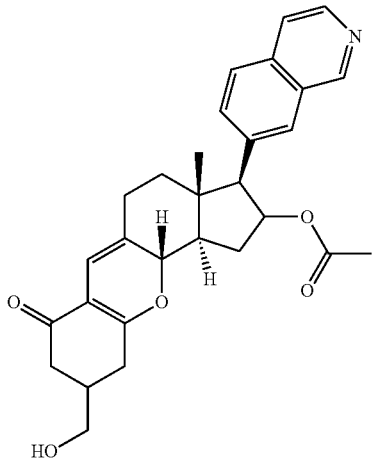

(CXXVIII)
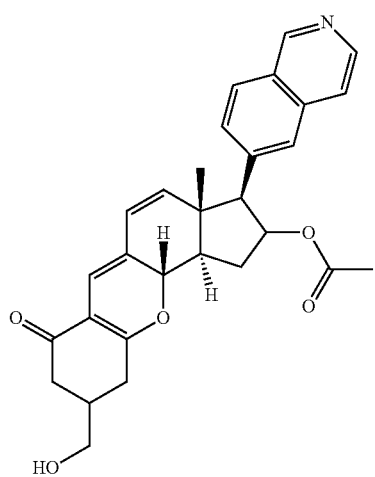
(CXXXI)
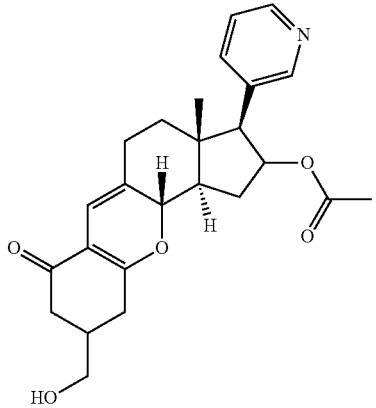
(CXXIX)
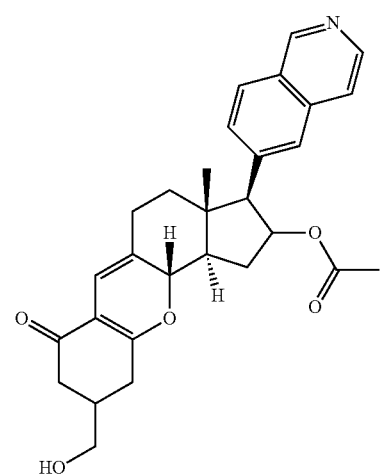
(CXXXII)
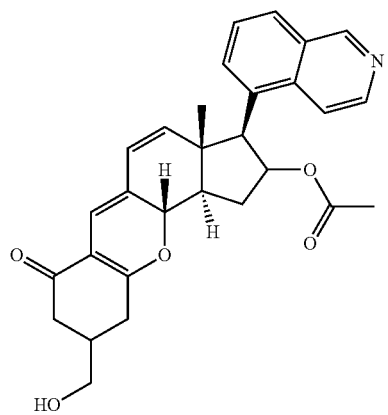
(CXXX)
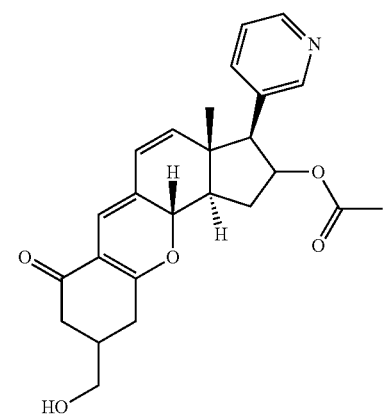
(CXXXIII)
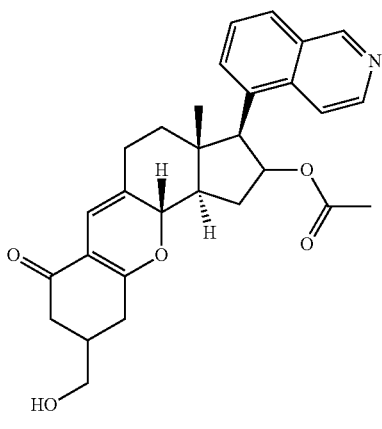

-continued
(CXXXIV)
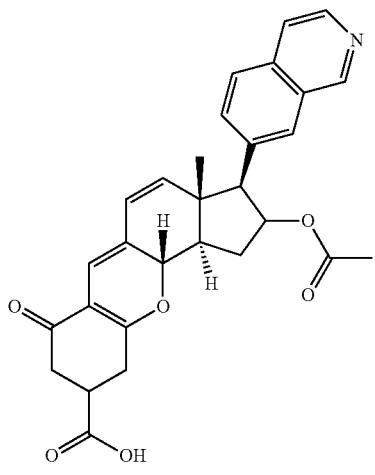
(CXXXV)
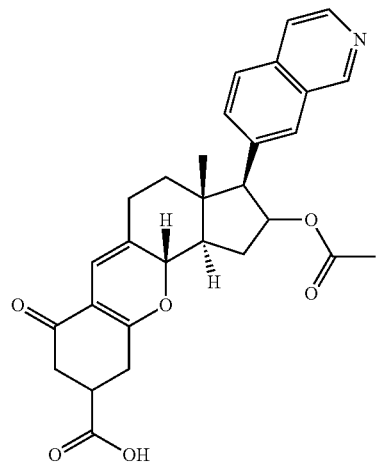
(CXXXVI)
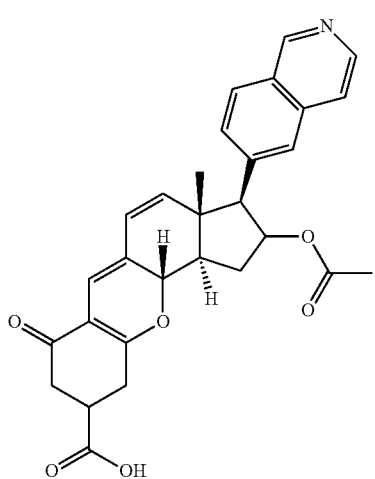
-continued
(CXXXVII)
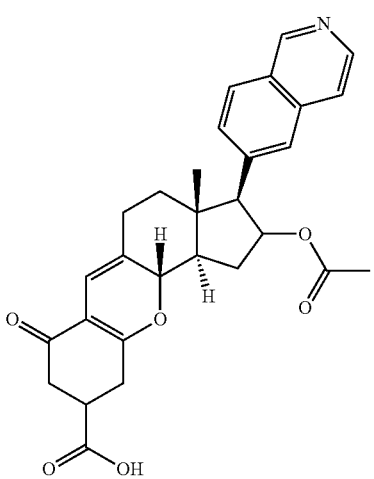
[Formula 23]
(CXXXVIII)
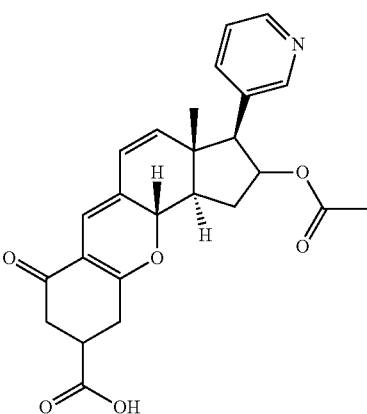
(CXXXIX)
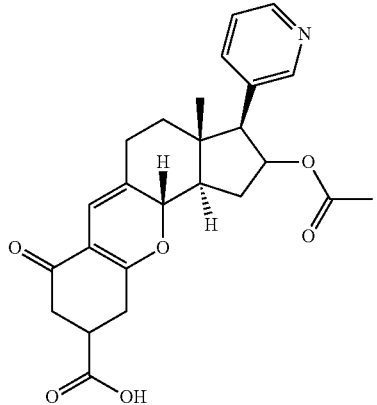

51
-continued
(CXL)
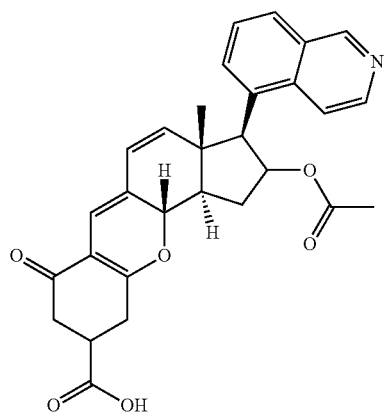
(CXLI)
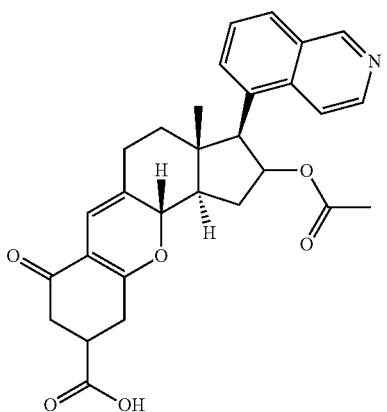
(CXLII)
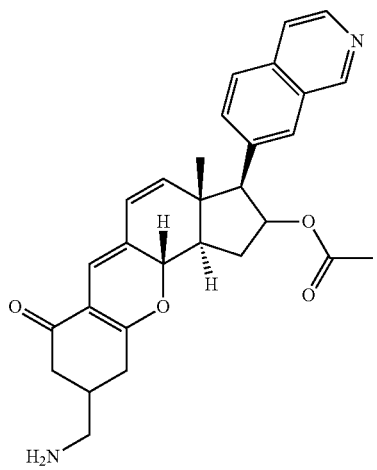
52
-continued
(CXLIII)
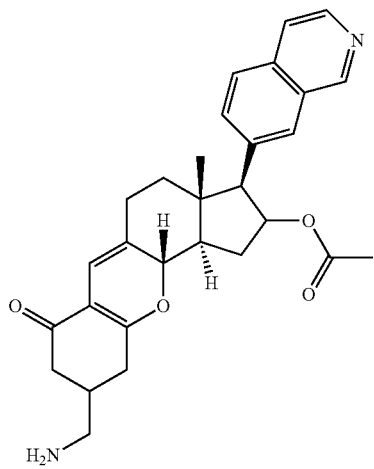
(CXLIV)
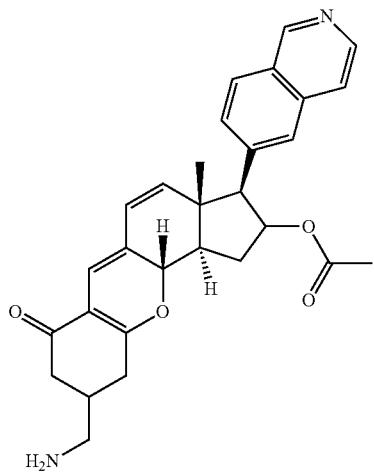
(CXLV)
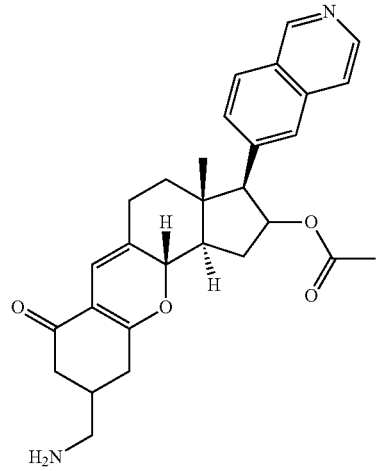

-continued
(CXLVI)
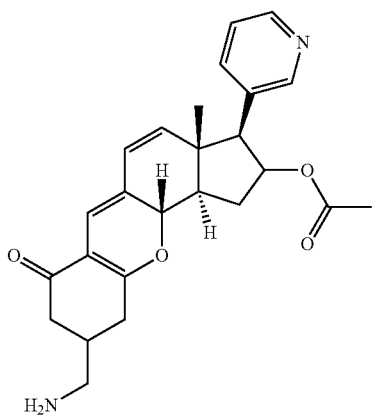
(CXLIX)
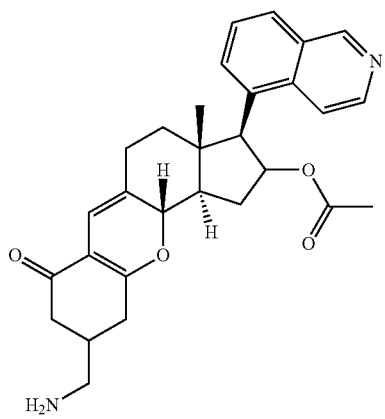
[Formula 24]
(CXLVII)
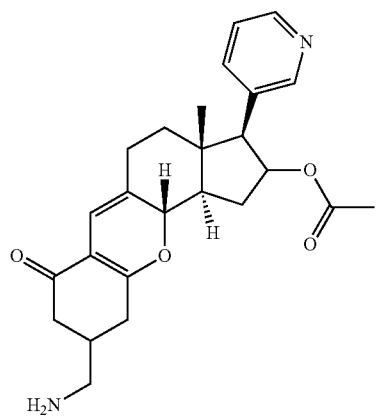
(CL)
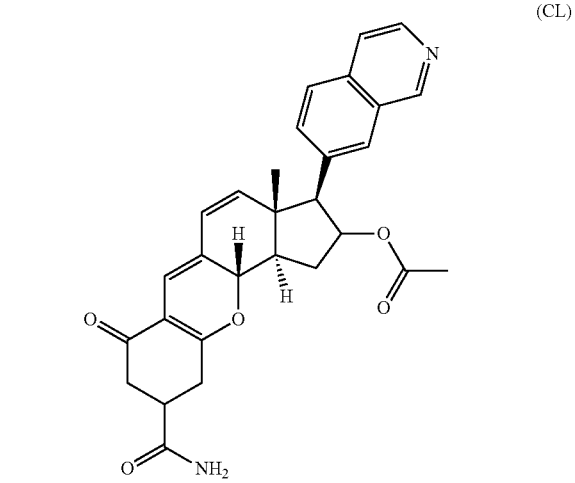
(CXLVIII)
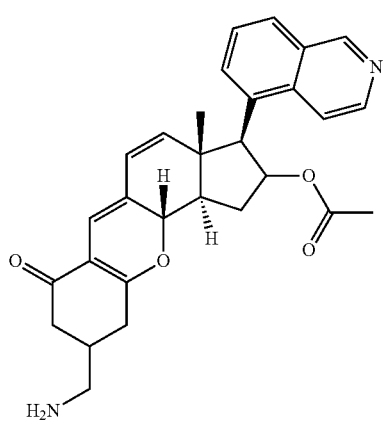
(CLI)
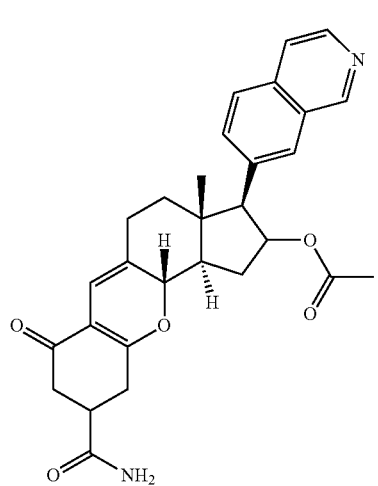

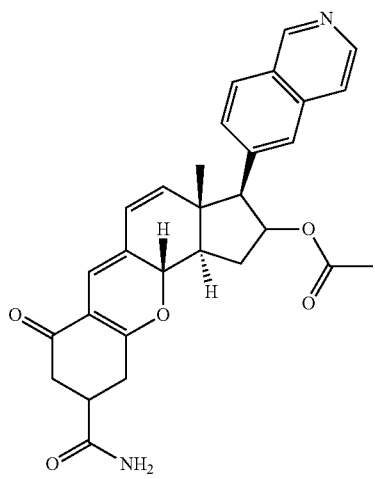
(CLII)
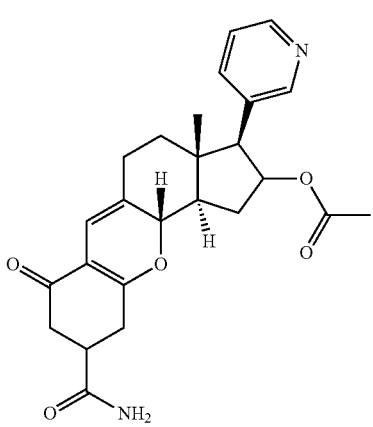
(CLV)
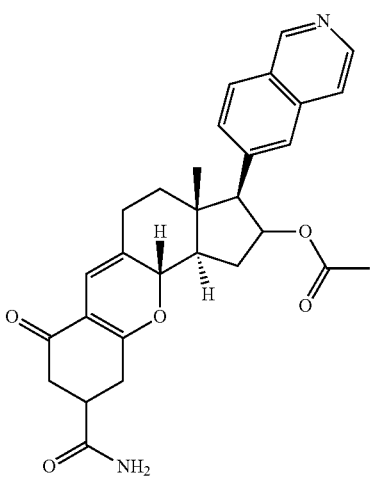
(CLIII)
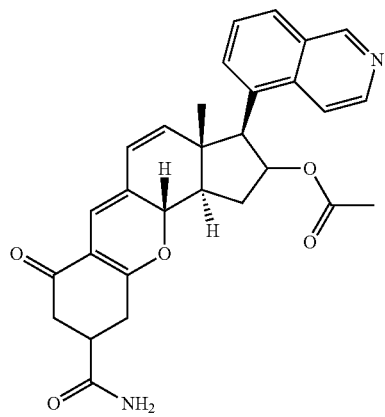
(CLVI)
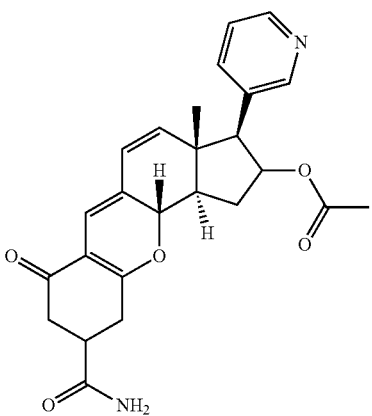
(CLIV)
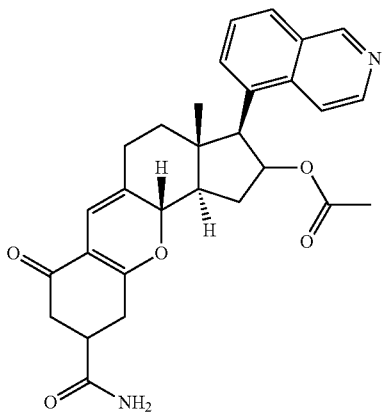
(CLVII)

-continued
(CLVIII)
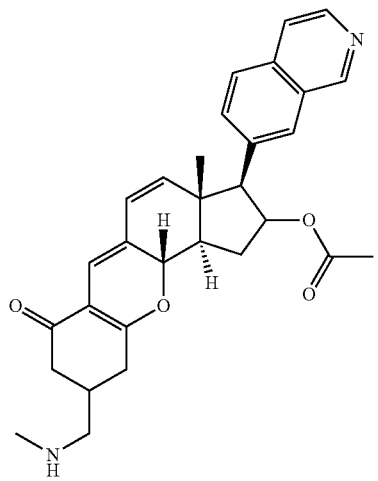
(CLIX)
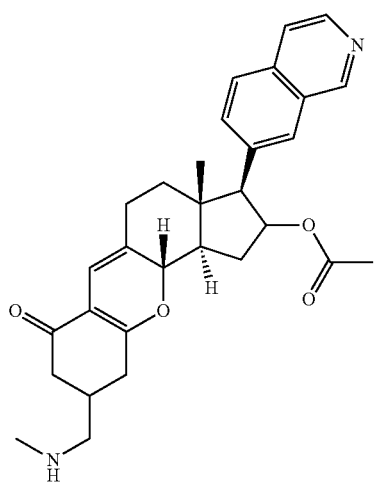
(CLX)
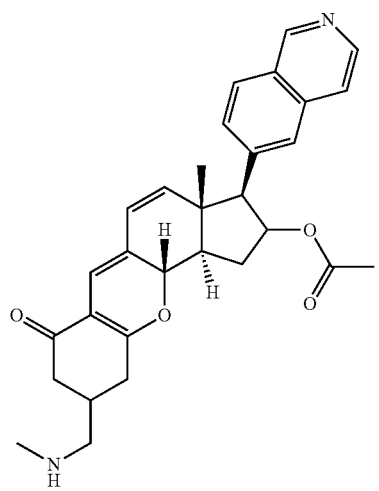
-continued
(CLXI)
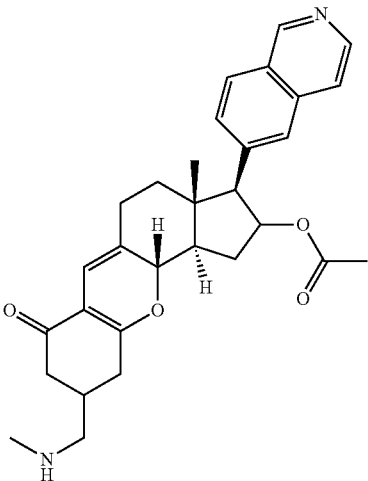
[Formula 25]
(CLXII)
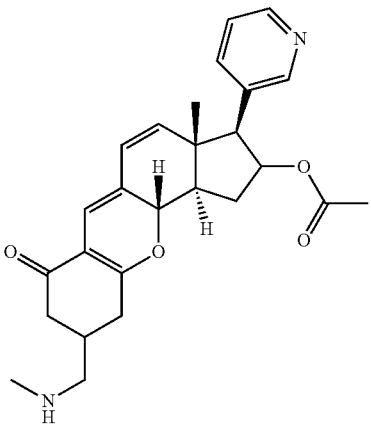
(CLXIII)
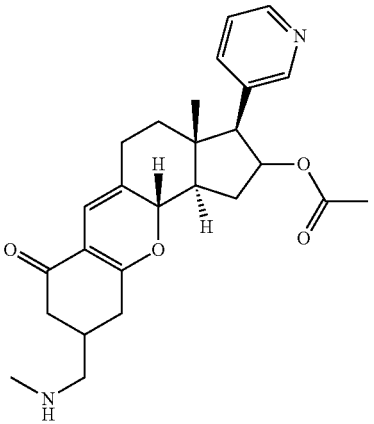

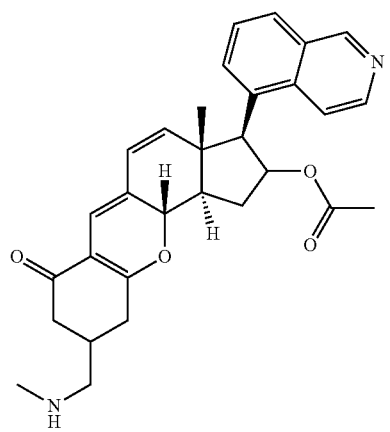
(CLXIV)
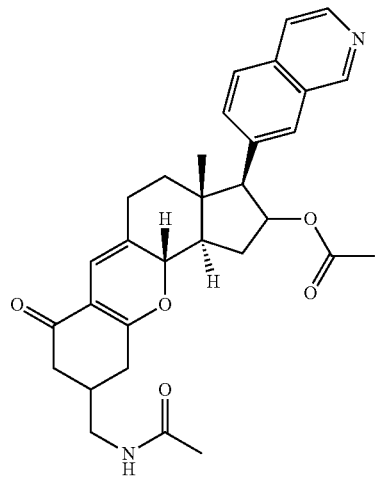
(CLXVII)
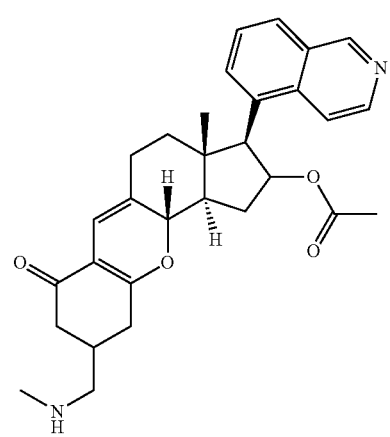
(CLXV)
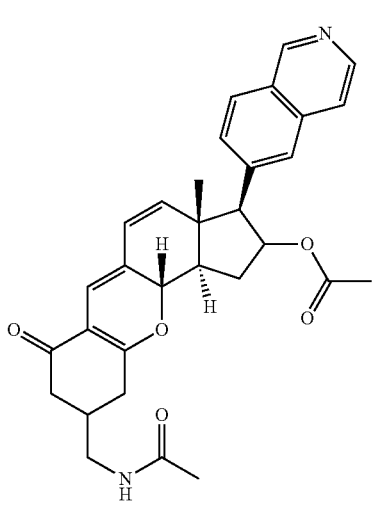
(CLXVIII)
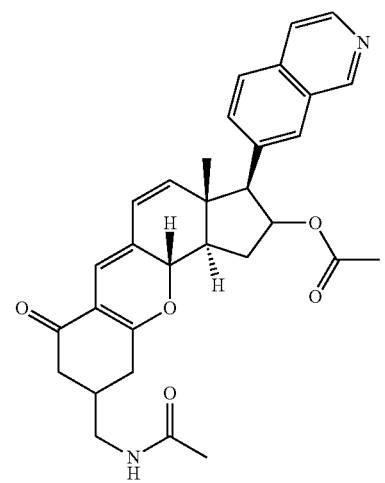
(CLXVI)
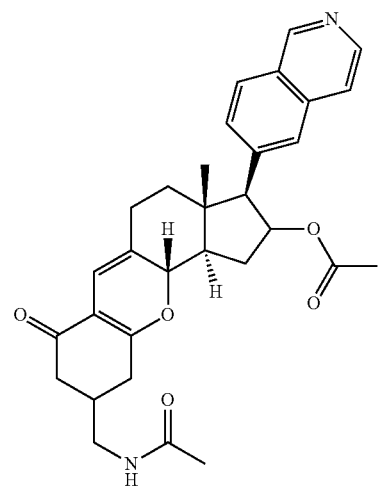
(CLXIX)

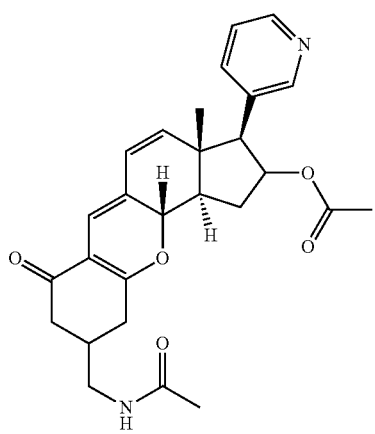
(CLXX)
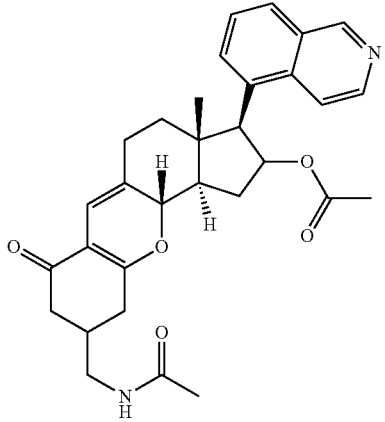
(CLXXIII)
[Formula 26]
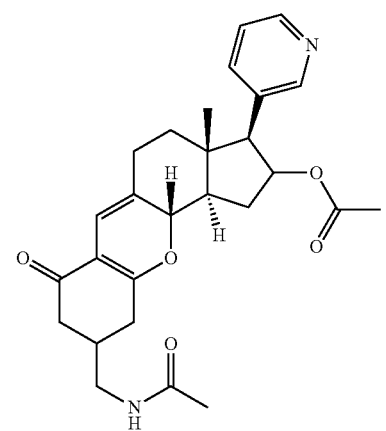
(CLXXI)
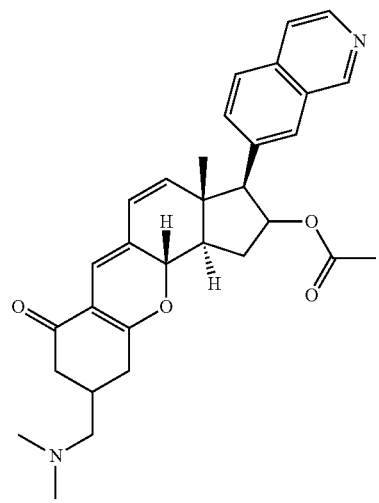
(CLXXIV)
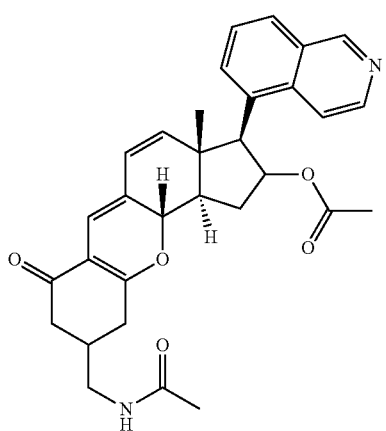
(CLXXII)
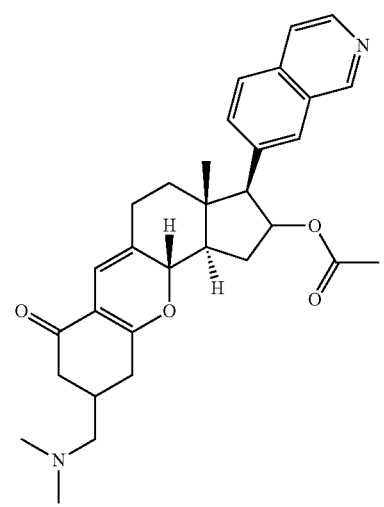
(CLXXV)

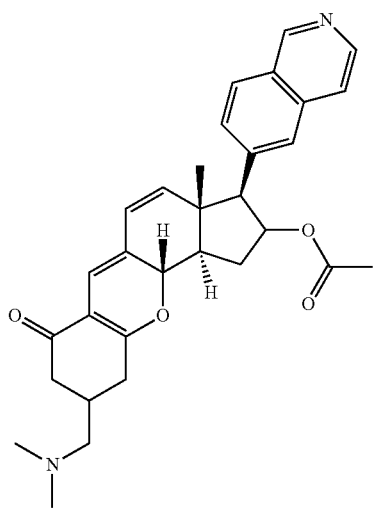
(CLXXVI)
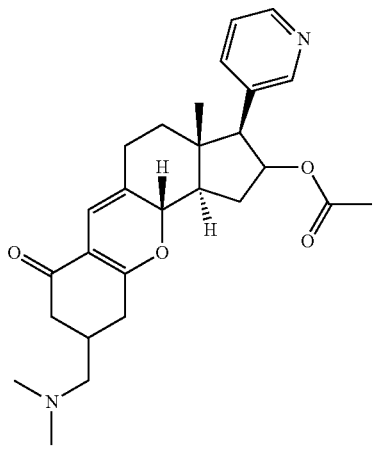
(CLXXIX)
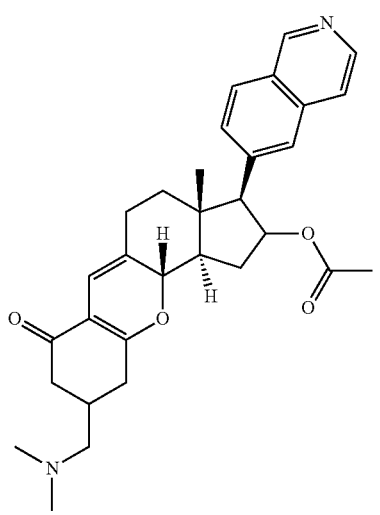
(CLXXVII)
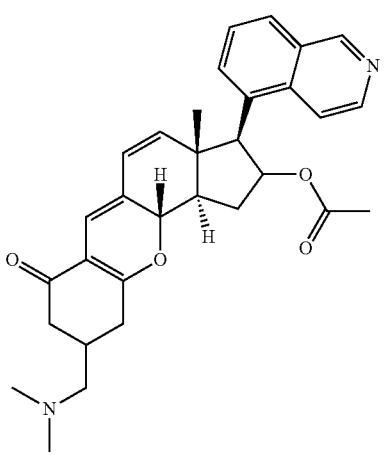
(CLXXX)
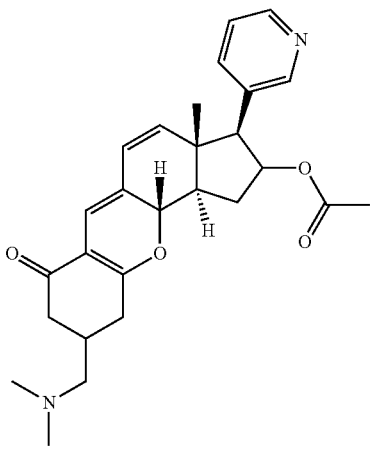
(CLXXVIII)
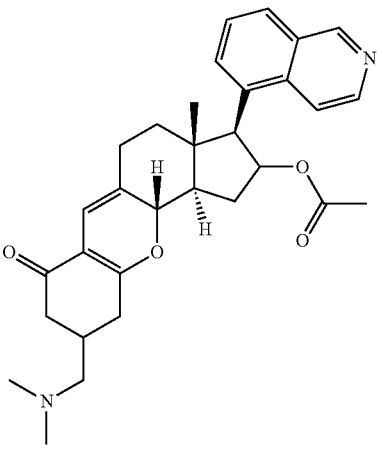
(CLXXXI)

-continued
(CLXXXII)
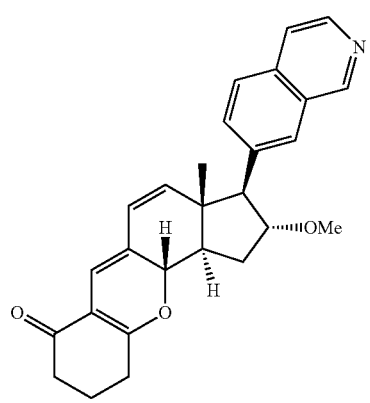
(CLXXXIII)
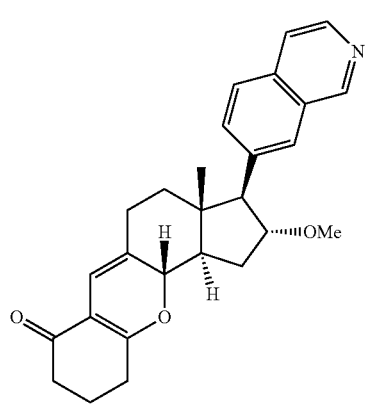
(CLXXXIV)
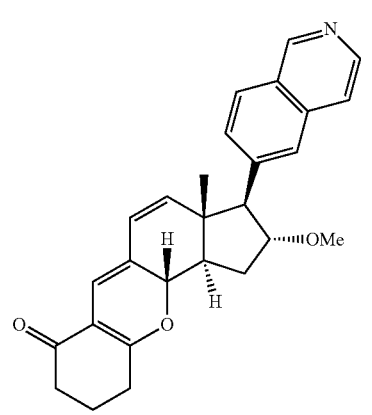
(CLXXXV)
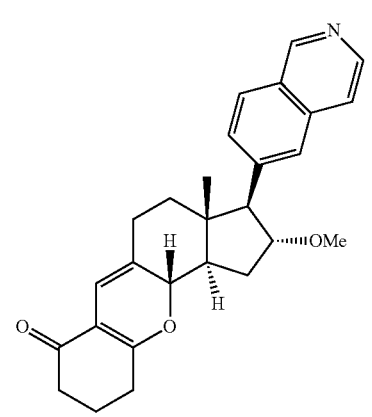
-continued
[Formula 27]
(CLXXXVI)
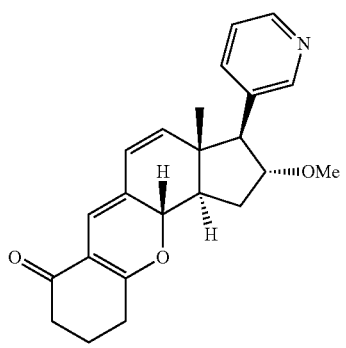
(CLXXXVII)
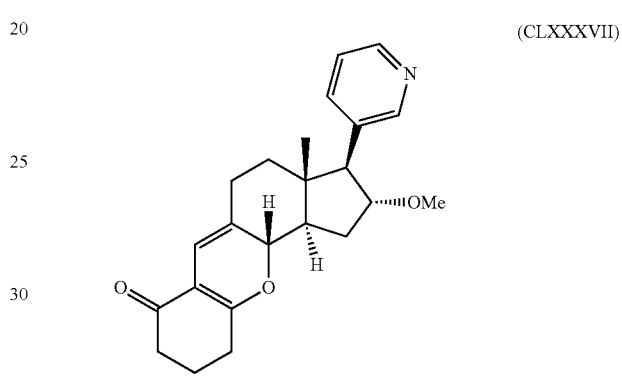
(CLXXXVIII)
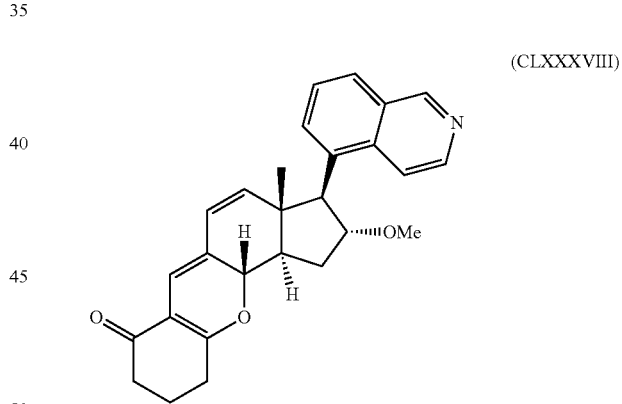
(CLXXXIX)
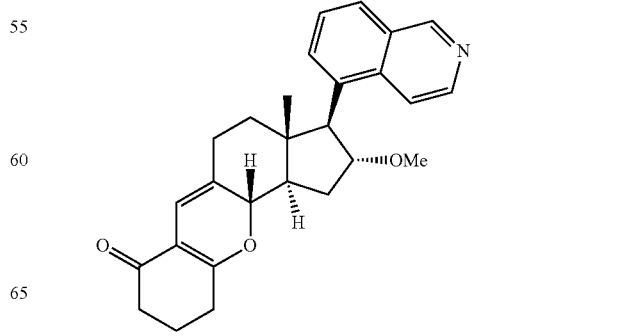

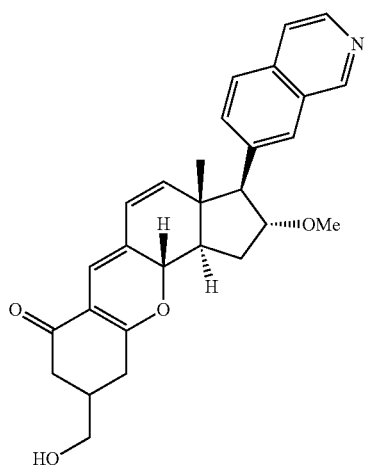
(CXC)
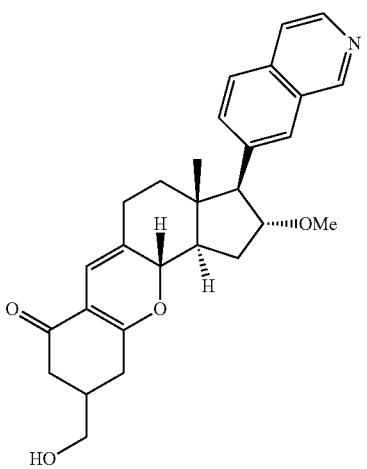
(CXCI)
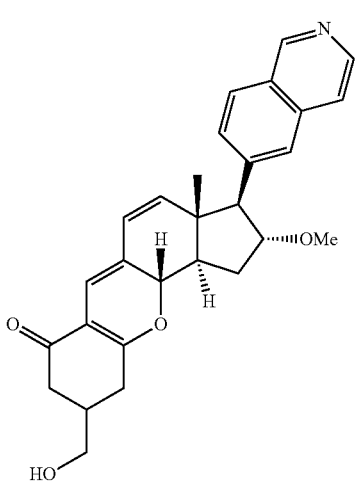
(CXCII)
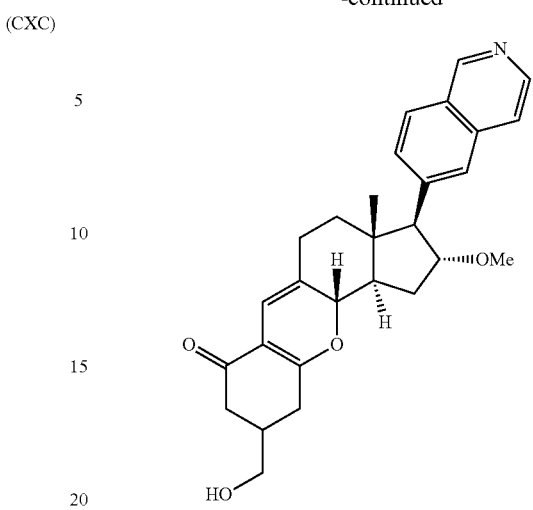
(CXCIII)
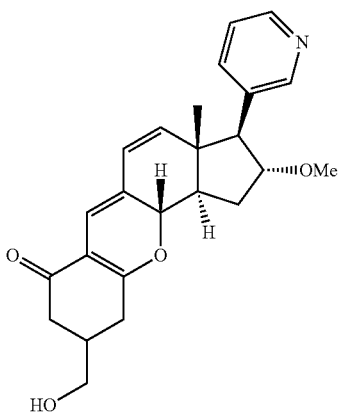
(CXCIV)
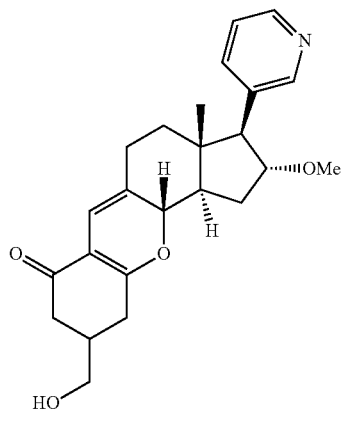
(CXCV)

(CXCVI)
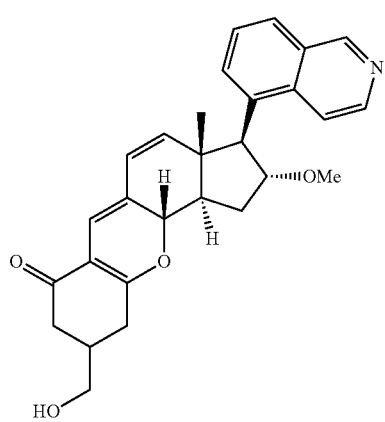
(CXCIX)
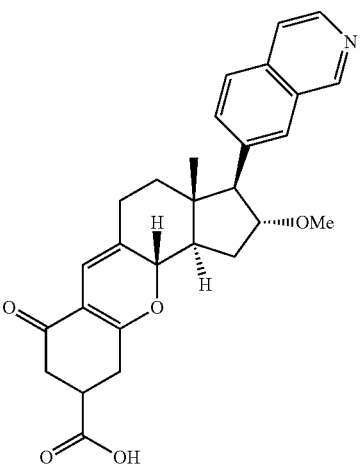
(CXCVII)
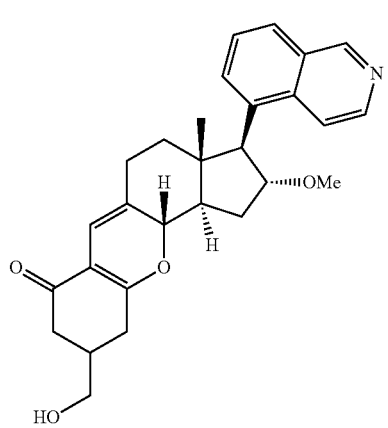
(CC)
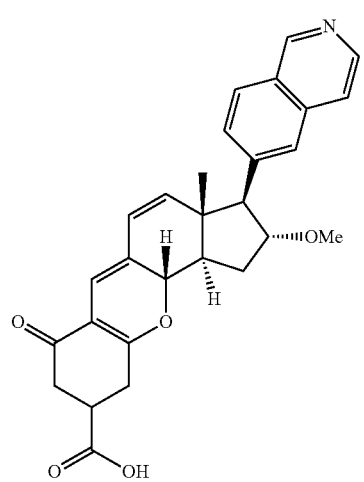
[Formula 28]
(CXCVIII)
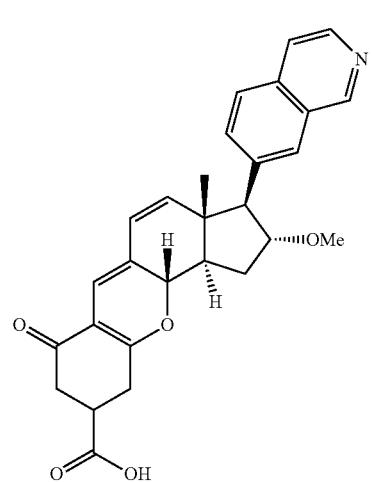
(CCI)

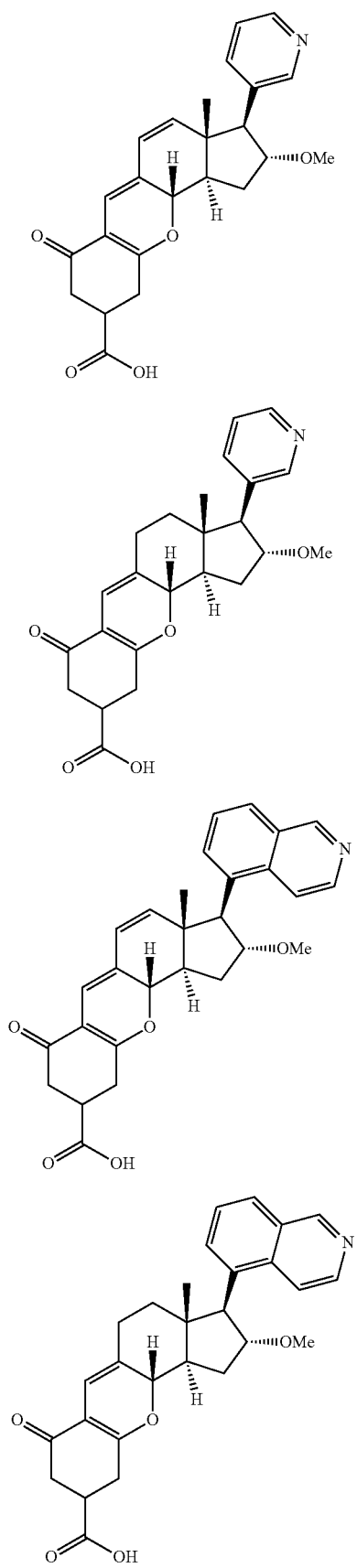
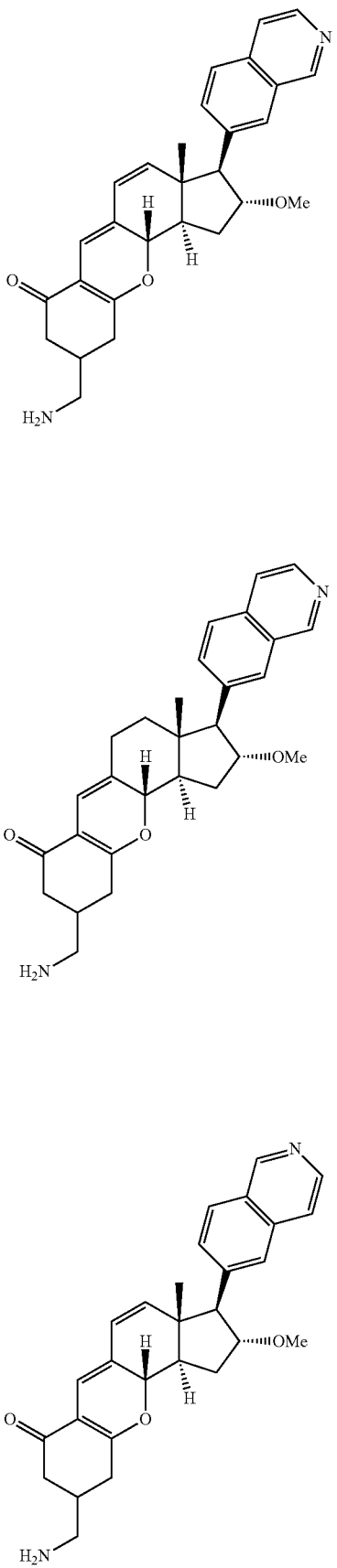

(CCIX)
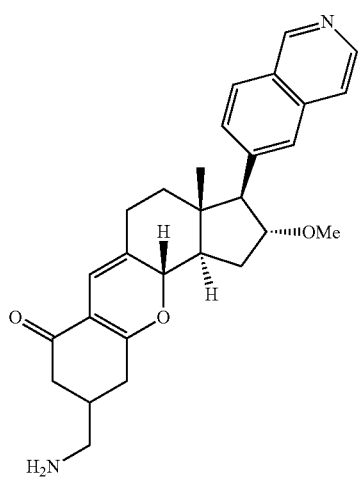
[Formula 29]
(CCX)
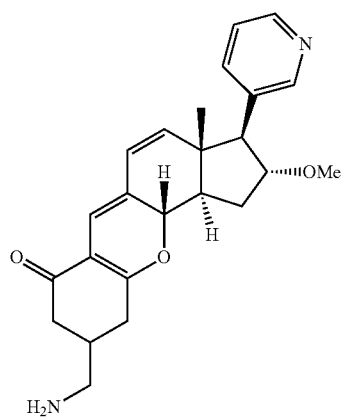
(CCXI)
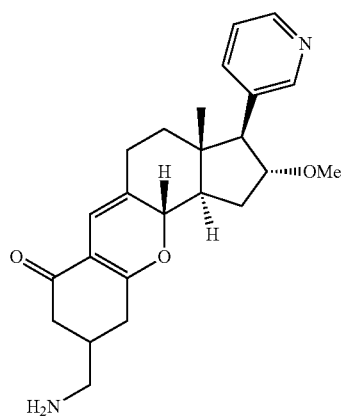
(CCXII)
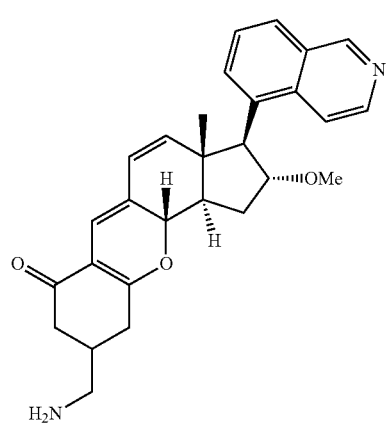
(CCXIII)
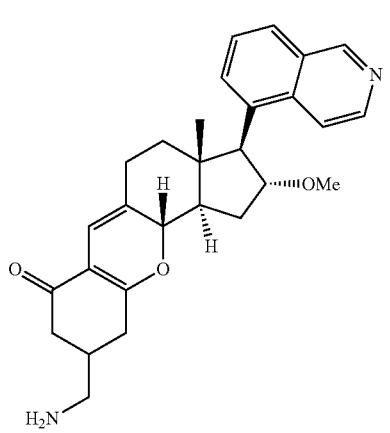
(CCXIV)
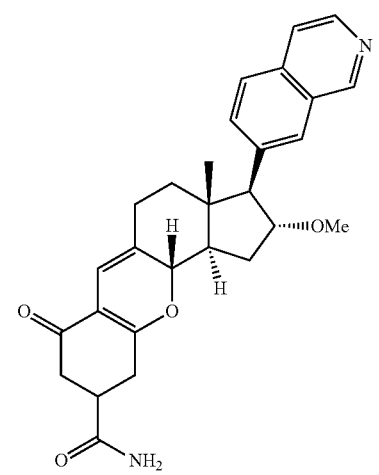

(CCXV)
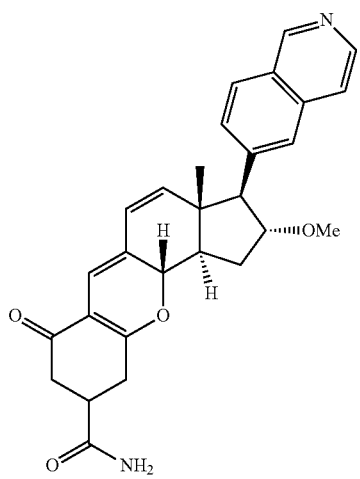
(CCXVIII)
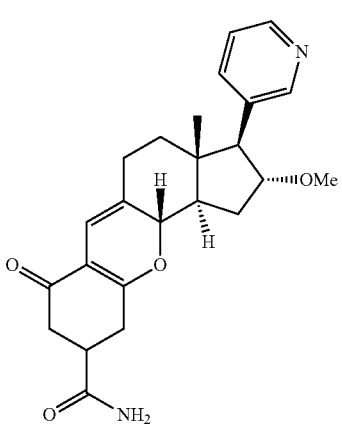
(CCXVI)
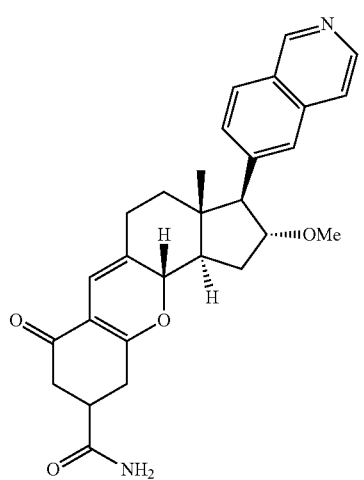
(CCXIX)
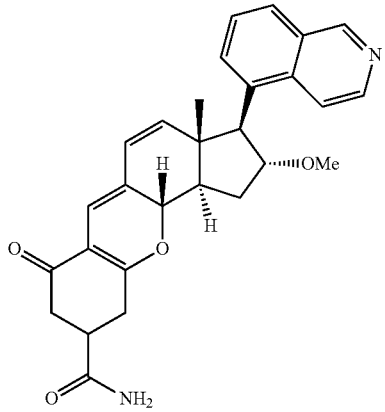
(CCXVII)
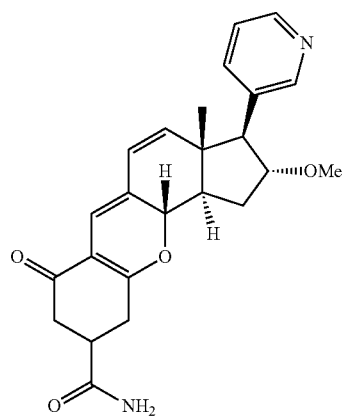
(CCXX)
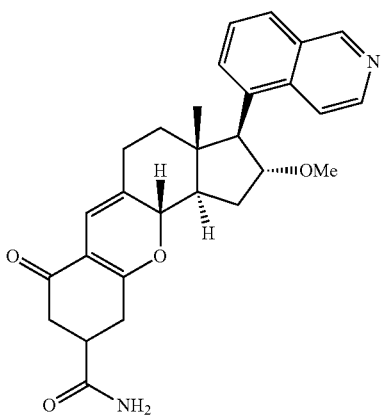

-continued
(CCXXI)
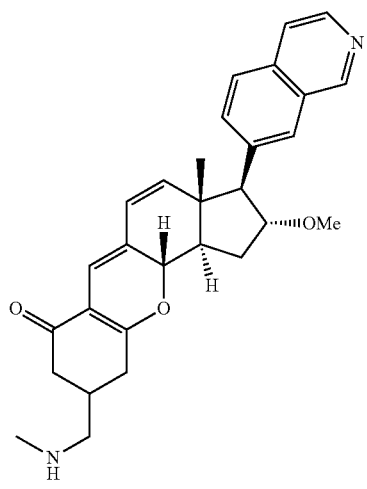
[Formula 30]
(CCXXII)
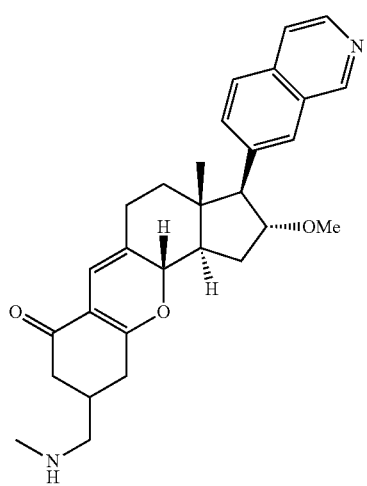
(CCXXIII)
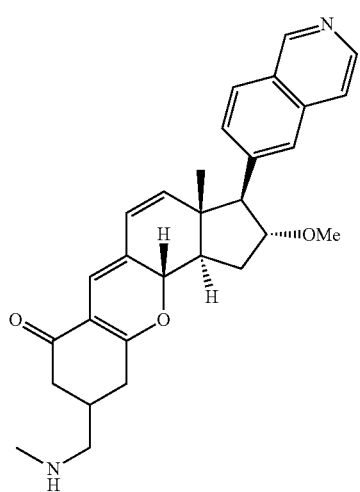
-continued
(CCXXIV)
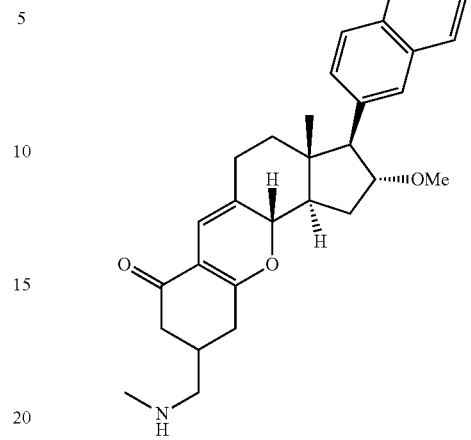
(CCXXV)
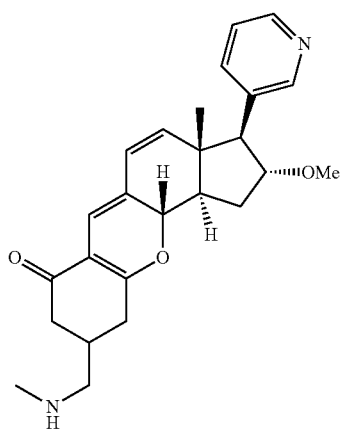
(CCXXVI)
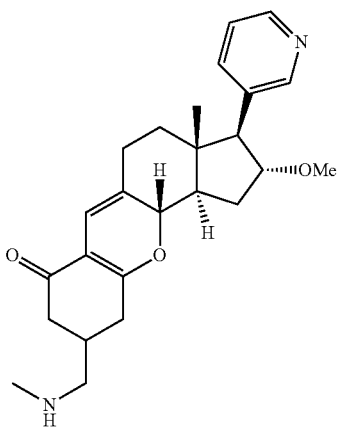

(CCXXVII)
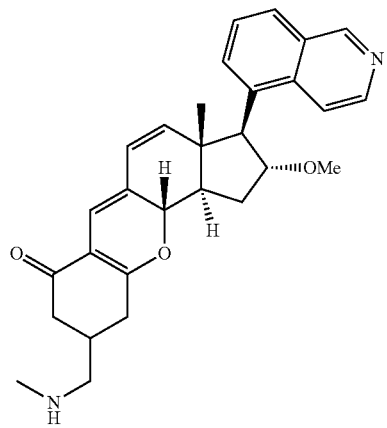
(CCXXVIII)
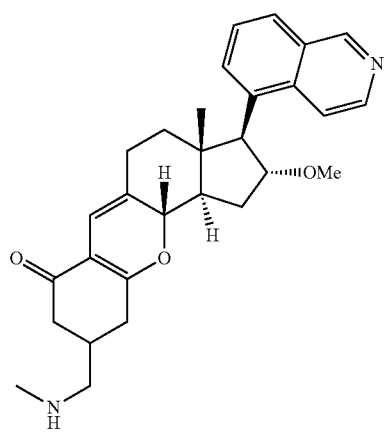
(CCXXIX)
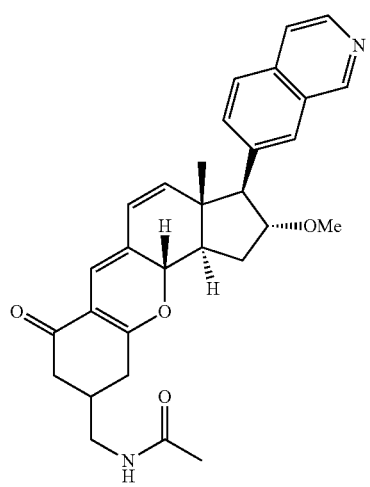
(CCXXX)
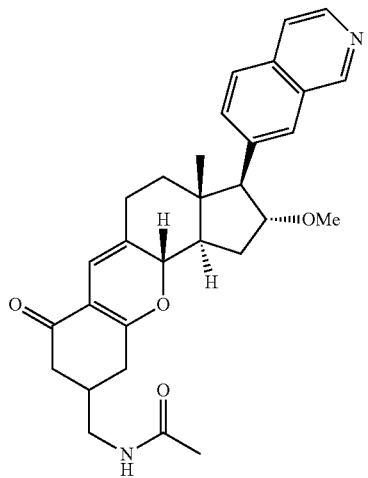
(CCXXXI)
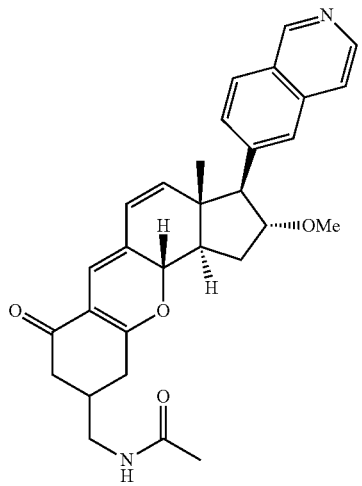
(CCXXXII)
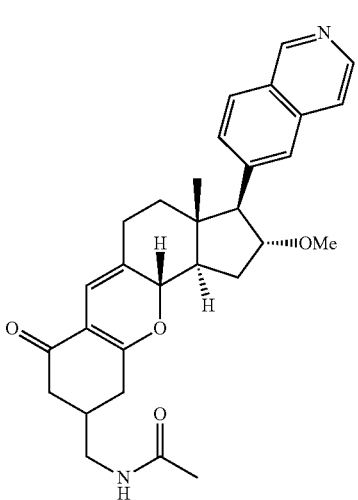

(CCXXXIII)
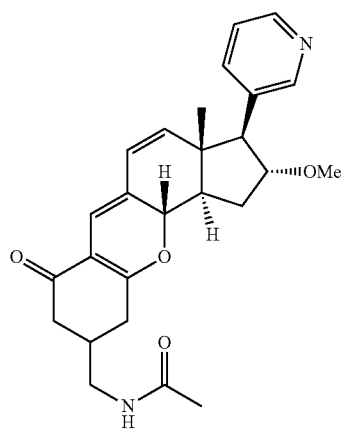
[Formula 31]
(CCXXXIV)
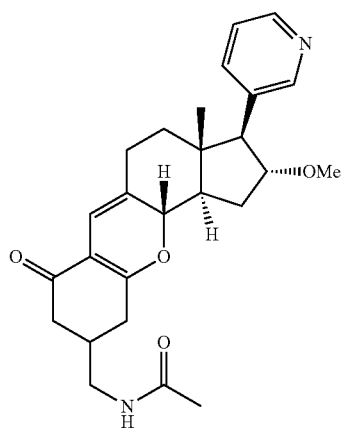
(CCXXXV)
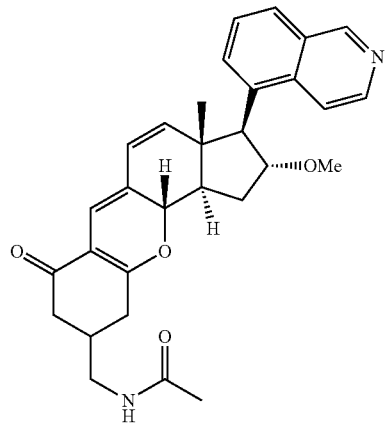
(CCXXXVI)
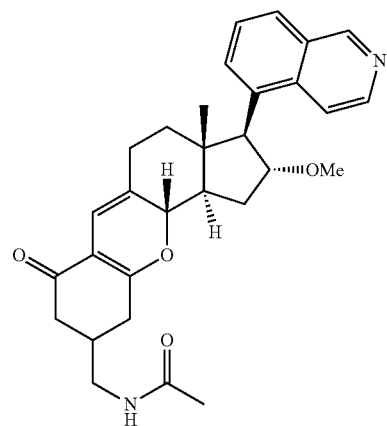
(CCXXXVII)
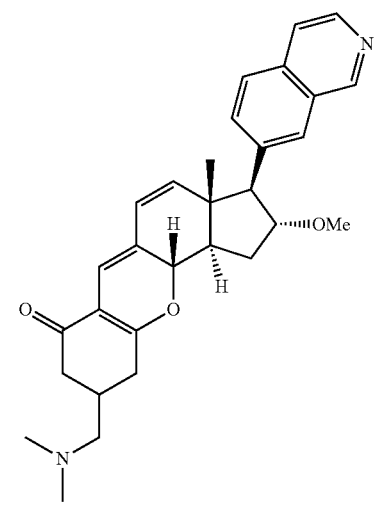
(CCXXXVIII)
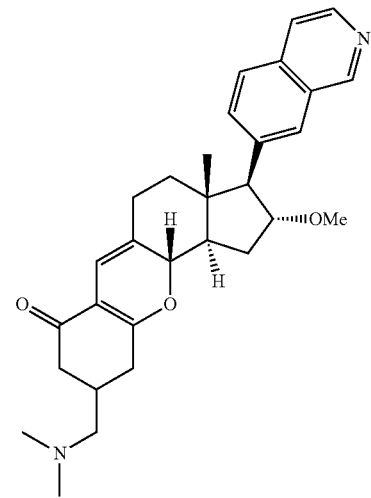

-continued
(CCXXXIX)
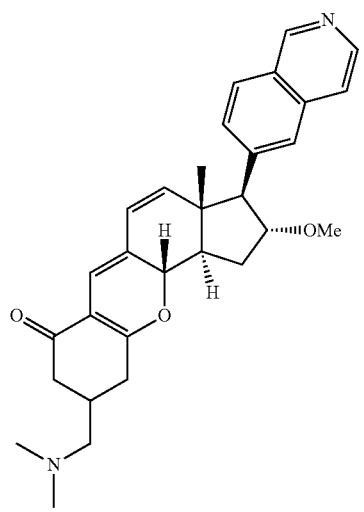
(CCXL)
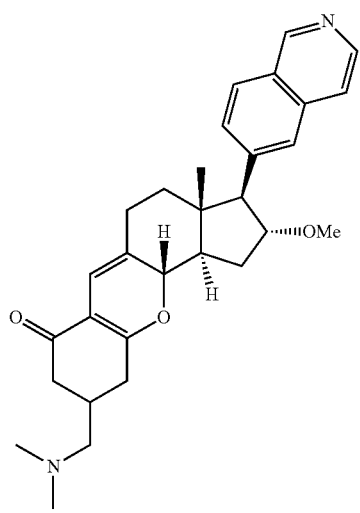
(CCXLI)
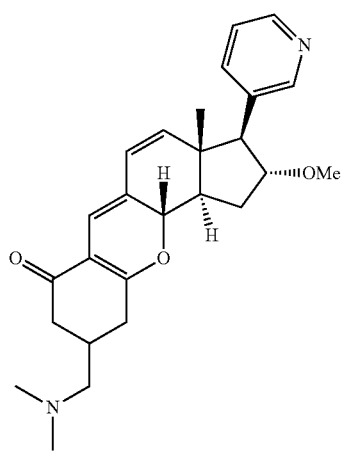
-continued
(CCXLII)
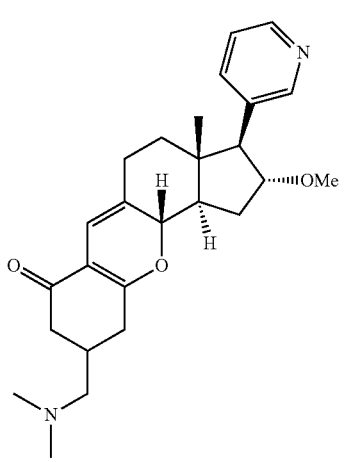
(CCXLIII)
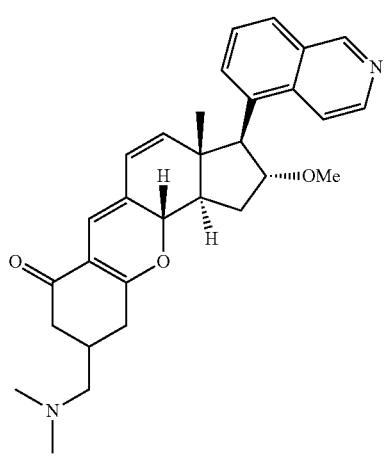
(CCXLIV)
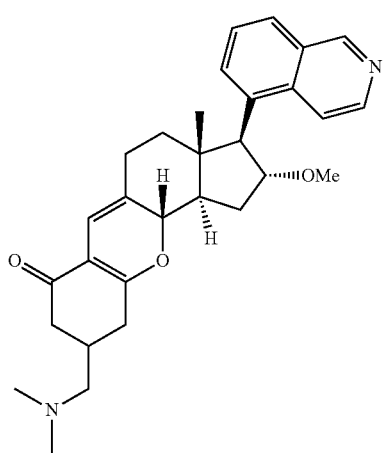

(CCXLV)

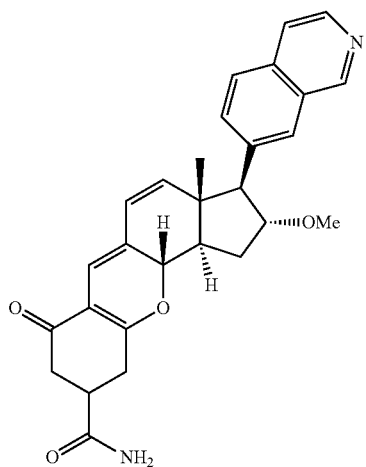

Particularly preferred as the compound of the present invention is a compound represented by the following formula (II), (XVIII), (XIX), (XXIII) or (LIV).

[Formula 32]

(II)

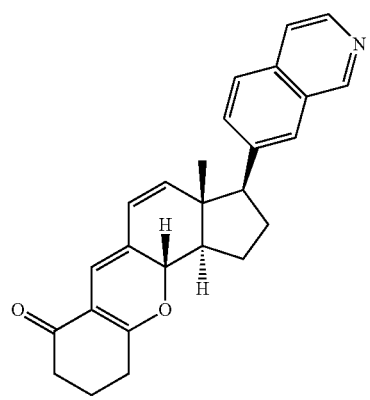

[Formula 33]

(XVIII)

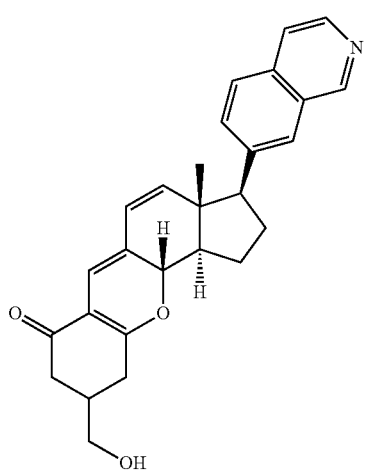

[Formula 34]

(XIX)

(XXIII)

(LIV)

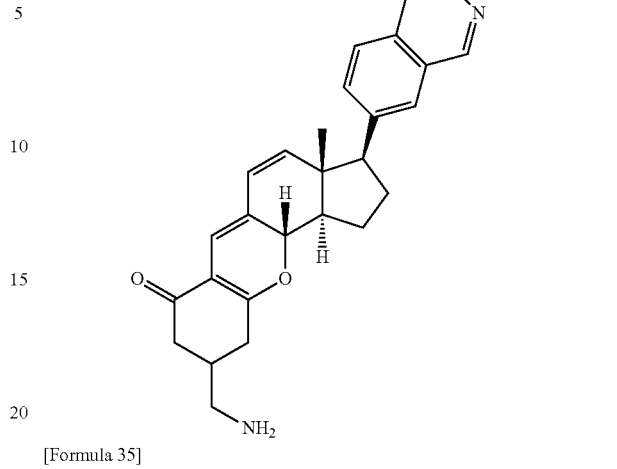

[Formula 35]

[Formula 36]

The compound represented by formula (II) can be chemically synthesized via 12 steps, and the yield is about 14%. The present inventors have confirmed that the compound represented by formula (II) has more than 100 times stronger anti-proliferative activity against vascular endothelial activity cells than against other cancer cells; inhibits the migration and tubulogenesis of human umbilical vein endothelial cells (HUVEC); has in vivo anti-angiogenic activity; and shows antitumor activity in a mouse cancer cell transplant model. According to the same method as for the synthesis of the compound of formula (II), the compounds represented by formulae (XVIII), (XIX), (XXIII) and (LIV) can also be chemically synthesized in an easy manner, and each of the compounds has selective anti-proliferative activity against vascular endothelial cells in a broad range of concentration like cortistatin A.

Examples of the "pharmaceutically acceptable salt" include salts of alkali metals (for example, potassium, sodium, lithium, etc.), salts of alkaline earth metals (for example, calcium, magnesium, etc.), ammonium salts (for example, a tetramethylammonium salt, a tetrabutylammonium salt, etc.), salts of organic amines (for example, triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), and acid addition salts (for example, inorganic acid salts, such as hydrochlorides, hydrobromides, hydriodides, sulfates, phosphates and nitrates; and organic acid salts, such as acetates, trifluoroacetates, lactates, tartrates, oxalates, fumarates, maleates, benzoates, citrates, methanesulfonates, ethanesulfonates, benzenesulfonates, toluenesulfonates, isethionates, glucuronates and gluconates).

Hereinafter, the compound represented by the general formula (M) or (I) of the present invention, or a pharmaceutically acceptable salt thereof is referred to as "the compound of the present invention."

The compound of the present invention can be produced according to any method without particular limitation, for example, the synthesis method described in Example 1, 4 or 5.

Isolation and purification of the compound of the present invention can be performed by a known technique, for example, phase transfer reaction, concentration, solvent, extraction, fractional distillation, pH shifting, crystallization, recrystallization, chromatography or the like. In the case where the compound of the present invention is obtained in a free form, it can be converted into an objective salt by a known technique. Conversely, in the case where the compound of the present invention is obtained in the form of a salt, it can be converted into a free form or an objective salt by a known technique.

In the case where the compound of the present invention has isomeric forms such as optical isomers, stereoisomers, regioisomers, rotamers and the like, each of the isomeric forms and mixtures thereof are included in the compound of the present invention. For example, in the case where the compound of the present invention can exist as optical isomers, each optical isomer resolved from the racemate is also included in the compound of the present invention. Each of these isomers can be individually obtained by a known synthesis method or separation method (concentration, solvent extraction, column chromatography, recrystallization, etc.).

The compound of the present invention may be a hydrate or a solvate. The compound of the present invention may be labeled with an isotope or the like.

The compound of the present invention has selective anti-proliferative activity against vascular endothelial cells, and therefore is useful as an active ingredient of vascular endothelial cell growth inhibitors. The compound of the present invention has anti-angiogenic activity, and therefore is useful as an active ingredient of angiogenesis inhibitors. Therefore, the compound of the present invention can be preferably used for prevention or treatment of diseases associated with vascular endothelial cell growth and/or angiogenesis. Examples of the diseases associated with vascular endothelial cell growth and/or angiogenesis include cancer (growth and metastasis of solid cancer), macular degeneration, diabetic retinopathy, neovascular glaucoma, inflammatory dermatosis, rheumatoid arthritis and osteoarthritis.

The compound of the present invention shows antitumor activity in a mouse cancer cell transplant model, and therefore is useful as an active ingredient of medicaments for cancer prevention or treatment. The cancer that the compound of the present invention can prevent or treat is not particularly limited, and examples thereof include lung cancer, colon cancer, prostate cancer, breast cancer, pancreatic cancer, esophageal cancer, gastric cancer, liver cancer, biliary tract cancer, spleen cancer, renal cancer, bladder cancer, uterine cancer, ovarian cancer, testicular cancer, thyroid cancer, brain tumor and hematological tumor. Preferred is a solid cancer characterized by tumor growth accompanied by angiogenesis.

The present invention provides a pharmaceutical composition comprising the compound of the present invention and a pharmaceutically acceptable carrier. The pharmaceutical composition of the present invention can be prepared by blending the compound of the present invention as an active ingredient, a pharmaceutically acceptable carrier and if needed an additive, and formulated into a dosage form. Specific examples of the dosage form include oral preparations such as tablets, coated tablets, pills, powders, granules, capsules, solutions, suspensions and emulsions; and parenteral preparations such as injections, infusions, suppositories, ointments and patches. The blending ratio of the carrier or the additive is appropriately determined based on the range of the blending ratio conventionally adopted in the pharmaceutical field. The carrier or the additive that can be blended is not particularly limited, and examples thereof include various carriers such as water, physiological saline, other aqueous solvents, and aqueous or oily bases; and various additives such as excipients, binders, pH adjusters, disintegrants, absorption enhancers, lubricants, colorants, corrigents and fragrances.

Examples of the additive that can be blended into tablets, capsules and the like include binders such as gelatin, cornstarch, tragacanth and gum arabic; excipients such as crystalline cellulose; bulking agents such as cornstarch, gelatin and alginic acid; lubricants as magnesium stearate; sweeteners such as sucrose, lactose and saccharin; and flavors such as peppermint, Gaultheria adenothrix oil and cherry. In the case where the unit dosage form is a capsule, a liquid carrier such as fats and oils can be further blended in addition to the above-mentioned materials. A sterile composition for injection can be prepared according to an ordinary pharmaceutical formulation practice, for example, by dissolving or suspending an active substance in a vehicle such as water for injection and a natural vegetable oil (such as sesame oil and coconut oil). As an aqueous liquid for injection, for example, physiological saline, an isotonic solution containing glucose and an auxiliary substance (for example, D-sorbitol, D-mannitol, sodium chloride, etc.), or the like can be used, optionally together with a suitable solubilizer such as alcohols (for example, ethanol), polyalcohols (for example, propylene glycol, polyethylene glycol) and nonionic surfactants (for example, polysorbate 80™, HCO-50). As an oily liquid, for example, sesame oil, soybean oil or the like can be used, optionally together with a solubilizer such as benzyl benzoate and benzyl alcohol. Further, a buffering agent (for example, a phosphate buffer, a sodium acetate buffer), a soothing agent (for example, benzalkonium chloride, procaine hydrochloride, etc.), a stabilizer (for example, human serum albumin, polyethylene glycol, etc.), a preservative (for example, benzyl alcohol, phenol, etc.), an antioxidant, etc. may also be blended.

The pharmaceutical preparation that can be obtained in the above manner can be administered to, for example, humans and other mammals (rats, mice, rabbits, sheep, pigs, cows, cats, dogs, monkeys, etc.). The dose may vary depending on the state of the animal, the cancer type, the condition, the administration method and the like, but in general, the daily oral dose for a human weighing about 60 kg is, for example, about 0.1 to 1000 mg, preferably about 1.0 to 500 mg, and more preferably about 3.0 to 200 mg in terms of the active ingredient. As for the parenteral dose, the amount for one dose may vary depending on the state of the animal, the cancer type, the condition, the administration method and the like, but for example in the case of injections, it is usually advantageous that the active ingredient is intravenously administered in an amount of, for example, about 0.01 to 100 mg, preferably about 0.01 to 50 mg, and more preferably about 0.01 to 20 mg per kg body weight. The daily total dose may be a single dose or divided into several portions.

The medicament of the present invention for cancer prevention or treatment can be used in combination with another cancer therapeutic drug. Such another cancer therapeutic drug is not particularly limited, but preferred is a chemotherapeutic drug, an immunotherapeutic drug or a hormone therapy drug, for example. According to the present invention, the medicament for cancer prevention or treatment an also be used in combination with radiotherapy.

The chemotherapeutic drug is not particularly limited and examples thereof include:
alkylating agents such as nitrogen mustard, nitrogen mustard N-oxide hydrochloride chlorambucil, cyclophosphamide, ifosfamide, thiotepa, carboquone, improsulfan tosilate, busulfan, nimustine hydrochloride, mitobronitol, melphalan, dacarbazine, ranimustine, estramustine phosphate sodium, triethylenemelamine, carmustine, lomustine, streptozocin, pipobroman, ethoglucid, carboplatin, cisplatin, nedaplatin, oxaliplatin, altretamine, ambamustine, dibrospidium chloride, fotemustine, prednimustine, pumitepa, Ribomustin, temozolomide, treosulfan, trofosfamide, zinostatin stimalamer, adozelesin, cystemustine and bizelesin;
antimetabolites such as mercaptopurine, 6-mercaptopurine riboside, thioinosine, methotrexate, pemetrexed, enocitabine, cytarabine, cytarabine ocfosfate, ancitabine hydrochloride, 5-FU and its derivatives (for example, fluorouracil, tegafur, UFT, doxifluridine, carmofur, galocitabine, emitefur, capecitabine, etc.), aminopterin, nelzarabine, leucovorin calcium, Tabloid, butocin, calcium folinate, calcium levofolinate cladribine emitefur, fludarabine, gemcitabine, hydroxycarbamide, pentostatin, piritrexim, idoxuridine, mitoquazone, tiazofurin, ambamustine and bendamustine; anticancer antibiotics such as actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride and idarubicin hydrochloride; and plant-derived anticancer drugs such as etoposide, etoposide phosphate, vinblastine sulfate, vincristine sulfate, vindesine sulfate, teniposide, paclitaxel, docetaxel and vinorelbine.

The immunotherapeutic drug is not particularly limited and examples thereof include picibanil, Krestin, sizofiran, lentinan, ubenimex, interferons, interleukins, macrophage colony-stimulating factor, granulocyte colony-stimulating factor, erythropoietin, lymphotoxins, BCG vaccine, *Corynebacterium parvum*, levamisole, polysaccharide K, procodazole and anti-CTLA4 antibody.

The hormone therapy drug is not particularly limited and examples thereof include fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, antiestrogens (for example, tamoxifen citrate, toremifene citrate, etc.), birth-control pills, mepitiostane, testololactone, aminoglutethimide, LH-RH agonists (for example, goserelin acetate, buserelin, leuprorelin, etc.), droloxifene, epitiostanol, ethinylestradiol sulfonate, aromatase inhibitors (for example, fadrozole hydrochloride, anastrozole, letrozole, exemestane, vorozole, formestane, etc.), antiandrogens (for example, flutamide, bicalutamide, nilutamide, etc.), 5α-reductase inhibitors (for example, finasteride, epristeride, etc.), corticosteroids (for example, dexamethasone, prednisolone, betamethasone, triamcinolone, etc.) and androgen synthesis inhibitors (for example, abiraterone, etc.).

The combined use of the medicament for cancer prevention or treatment, with another cancer therapeutic drug or radiotherapy, can provide the following effects without limitation:
(1) synergistic effect is obtainable;
(2) the dose is reducible;
(3) prolonged treatment period is selectable; and
(4) persistent therapeutic effect can be expected.

In the case where the medicament for cancer prevention or treatment and another cancer therapeutic drug are used in combination, they may be simultaneously administered to a subject, or separately administered thereto at some interval. The dose of the drug in combined use can be determined based on its clinical dose and is appropriately selected depending on the subject, the age and body weight of the subject, the condition, the administration time, the dosage form, the administration method, the combination of drugs, etc.

EXAMPLES

Hereinafter, the present invention will be illustrated in detail by Examples, but is not limited thereto.

Example 1

Synthesis of Compound Represented by Formula (II)

According to the scheme shown in FIG. 1, the compound represented by formula (II) (hereinafter referred to as "CA-1") was synthesized.

(1) Synthesis of compound 3 ((3aS,7aS)-7a-methyl-hexahydro-1H-indene-1,5(6H)-dione)

Under argon atmosphere, t-BuMgCl (1.0 M in THF, 6.02 mL, 6.02 mmol) was added to a THF solution (28 mL) of CuI (882 mg, 4.63 mmol) at −50° C., and the mixture was stirred for 20 minutes. To this, HMPA (8.10 ml, 46.3 mmol) was added and the reaction mixture was stirred at −50° C. for 20 minutes. After a THF solution of compound 2 (760 mg, 4.63 mmol) was added via a cannula at −78° C., DIBAL-H (1.0 M in n-hexane, 7.41 mL, 7.41 mmol) and a THF solution (9.0 mL) of HMPA (4.05 mL, 23.2 mmol) were slowly added dropwise via a cannula, and the mixture was stirred at −78° C. for 30 minutes. The temperature of the reaction mixture was made to slowly rise to −40° C., and the reaction mixture was stirred for additional 3 hours. After the temperature of the reaction mixture was made to rise to 0° C., a 5% HCl aqueous solution was added and then extraction with AcOEt was performed. The organic layer was dried over Na$_2$SO$_4$ and filtered, and the filtrate was concentrated in vacuo. The residue was purified by silica gel column chromatography (n-hexane/AcOEt=2:1) and compound 3 (592 mg, 77%) was obtained.

IR (KBr): 2959, 1738, 1711 cm$^{-1}$. $[\alpha]_D^{21}$ +150.0 (c 1.70, CHCl$_3$). $^1$H-NMR (500 MHz, CDCl$_3$) δ: 2.55-2.50 (2H, m), 2.48-2.40 (3H, m), 2.22-2.14 (1H, m), 2.08-2.00 (1H, m), 1.96-1.90 (2H, m), 1.68 (1H, tt, J=11.6, 8.5 Hz), 1.60 (1H, dd, J=13.4, 9.2 Hz), 1.05 (3H, s).

(2) Synthesis of compound 4 ((3a'S,7a'S)-7a'-methyl-hexahydrospiro[[1,3]dioxolane-2,5'-inden]-1'(6'H)-one)

To a CH$_3$CN solution (32 mL) of compound 3 (535 mg, 3.22 mmol) ethylene glycol (5.4 ml, 96.6 mmol) and oxalic acid dihydrate (203 mg, 1.61 mmol) were added at 0° C., and the mixture was stirred at room temperature for 8 hours. After the temperature of the reaction mixture was made to drop to 0° C., a saturated NaHCO$_3$, solution was added and then extraction with AcOEt was performed. The organic layer was dried over Na$_2$SO$_4$ and filtered, and the filtrate was concentrated in vacuo. The residue was purified by silica gel column chromatography (n-hexane/AcOEt=2:1) and compound 4 (624 mg, 92%) was obtained.

IR (KBr): 2953, 2887, 1732, 1068 cm$^{-1}$. $[\alpha]_D^{21}$ +91.3 (c 1.28, CHCl$_3$). $^1$H-NMR (500 MHz, CDCl$_3$) δ: 3.92-3.86 (4H, m), 2.40 (1H, dd, J=19.0, 9.2 Hz), 2.09 (1H, dt, J=19.0, 11.0 Hz), 1.97-1.93 (1H, m), 1.83-1.80 (1H, m), 1.73-1.64 (5H, m), 1.57 (1H, tt, J=12.5, 9.0 Hz), 1.44 (1H, td, J=13.9, 5.7 Hz), 0.88 (3H, s) ESI MS: m/z 233 (M+Na)$^+$. HR-ESI MS: m/z 233.1154, calcd for C$_{12}$H$_{18}$O$_3$Na. Found: 233.1160.

(3) Synthesis of compound 5 ((3a'S,7a'S)-7a'-methyl-3',3a',4',6',7',7a'-hexahydrospiro-[[1,3]dioxolane-2,5'-inden]-1'-yltrifluoromethanesulfonate)

To a THF solution (14 ml) of compound 4 (300 mg, 1.43 mmol), phenyl-N-triflimide (1.02 g, 2.86 mmol) and KHMDS (0.5 M in toluene, 4.3 mL, 2.15 mmol) were added at −78° C., and the mixture was stirred for 30 minutes. After the temperature of the reaction mixture was made to rise to 0° C., water was added and then extraction with Et$_2$O was performed. The organic layer was dried over Na$_2$SO$_4$ and filtered, and the filtrate was concentrated in vacuo. The residue was purified by silica gel column chromatography (n-hexane/AcOEt=4:1) and compound 5 (420 mg, 85%) was obtained.

IR (KBr): 2955, 2885, 1421, 1213, 1141, 1055 cm$^{-1}$. $[\alpha]_D^{20}$ +69.2 (c 1.41, CHCl$_3$). $^1$H-NMR (500 MHz, CDCl$_3$) δ: 5.57 (1H, dd, J=3.3, 1.6 Hz), 3.92 (4H, m), 2.23-2.15 (2H, m), 2.05-2.02 (1H, m), 1.77-1.60 (7H, m), 1.02 (3H, s). ESI MS: m/z 365 (M+Na)$^+$. HR-ESI MS: m/z 365.0647, calcd for C$_{13}$H$_{17}$O$_5$F$_3$NaS. Found: 365.0646.

(4) Synthesis of compound 6 (7-((3a'S,7a'S)-7a'-methyl-3',3a',4',6',7',7a'-hexahydrospiro[[1,3]dioxolane-2,5'-inden]-1'-yl)isoquinoline)

To a DMF solution (5.0 mL) of compound 5 (200 mg, 0.584 mmol), a solution (5.0 mL) of 7-(4,4,5,5-tetramethyl-1,3,2-dioxaborolan-2-yl)isoquinoline (162 mg, 0.642 mmol) in DMF, Pd(PPh$_3$)$_4$ (100 mg, 0.0876 mmol) and K$_2$CO$_3$ (239 mg, 1.75 mmol) were added at room temperature, and the mixture was stirred at 50° C. for 30 minutes. After the temperature of the reaction mixture was made to drop to 0° C., water was added and then extraction with AcOEt was performed. The organic layer was dried over Na$_2$SO$_4$ and filtered, and the filtrate was concentrated in vacuo. In this way, a crude product containing compound 6 was obtained.

(5) Synthesis of compound 7 ((3aS,7aS)-3-(isoquinolin-7-yl)-3a-methyl-4,5,7,7a-tetrahydro-1H-inden-6(3aH)-one)

To an acetone/water solution (6.2 mL+0.62 mL) of the crude product containing compound 6, p-toluenesulfonic acid monohydrate (237 mg, 1.23 mmol) was added at 0° C., and the mixture was stirred at room temperature for 2 hours. After the temperature of the reaction mixture was made to drop to 0° C., a saturated NaHCO$_3$ solution was added and then extraction with AcOEt was performed. The organic layer was dried over Na$_2$SO$_4$ and filtered, and the filtrate was concentrated in vacuo. The residue was purified by silica gel column, chromatography (n-hexane/AcOEt=1:2) and compound 7 (80 mg, 50% in 2 steps) was obtained.

IR (KBr): 2935, 1707, 850 cm$^{-1}$. $[\alpha]_D^{20}$ +94.0 (c 2.54, CHCl$_3$). $^1$H-NMR (500 MHz, CDCl$_3$) δ: 9.22 (1H, s), 8.49 (1H, d, J=6.1 Hz), 7.92 (1H, s), 7.77 (1H, d, J=9.8 Hz), 7.75 (1H, dd, J=8.9, 1.5 Hz), 6.17 (1H, s), 2.62-2.50 (4H, m), 2.39-2.36 (4H, m), 2.28-2.21 (1H, m), 1.97-1.95 (1H, m), 1.32 (3H, s). ESI MS: m/z 278 (M+H)$^+$. HR-ESI MS: m/z 278.1545, calcd for C$_{19}$H$_{20}$NO. Found: 278.1544.

(6) Synthesis of compound 8 (1S,3aS,7aS)-1-(isoquinolin-7-yl)-7a-methylhexahydro-1H-inden-5(6H)-one)

To an AcOEt solution (3.0 mL) of compound 7 (73 mg, 0.261 mmol), Pd/C (21.9 mg) was added at room temperature, and the mixture was stirred under hydrogen atmosphere for 12 hours. The reaction mixture was filtered through Celite and the filtrate was concentrated in vacuo. In this way, compound 8 (71 mg, 98%) was obtained.

IR (KBr): 2959, 1709, 852 cm$^{-1}$. $^1$H-NMR (500 MHz, CDCl$_3$) δ: 9.22 (1H, s), 8.48 (1H, d, J=6.1 Hz), 7.80 (1H, s), 7.75 (1H, d, J=7.9 Hz), 7.62 (1H, d, J=6.1 Hz), 7.57 (1H, d, J=8.5 Hz), 2.99 (1H, t, J=9.8 Hz), 2.46-2.44 (1H, m), 2.37-2.30 (3M, m), 2.19-2.18 (1H, m), 2.12-2.10 (1H, m), 1.91-1.90 (1H, m), 1.78-1.75 (2H, m), 1.59-1.57 (1H, m), 0.75 (3H, s). ESI MS: m/z 280 (M+M)$^+$. HR-ESI MS: m/z 280.1701, calcd for C$_{19}$H$_{22}$NO. Found: 280.1714.

(7) Synthesis of compound 9 ((1R,3aS,7aR)-1-(isoquinolin-7-yl)-7a-methyl-2,3,3a,4-tetrahydro-1H-inden-5(7aH)-one)

To a CH$_3$CN solution (2.0 mL) of compound 8 (28 mg, 0.100 mmol), HMDS (0.21 mL, 1.00 mmol), NaI (75.2 mg, 0.500 mmol) and TMSCl (0.062 mL, 0.500 mmol) were added at 0° C., and the mixture was stirred at room temperature for 3 hours. After the temperature of the reaction mixture was made to drop to 0° C., a saturated NH$_4$Cl solution was added and then extraction with CH$_2$Cl$_2$ was performed. The organic layer was dried over Na$_2$SO$_4$ and filtered, and the filtrate was concentrated in vacuo. To a DMSO solution (1.0 mL) of the resulting product, 2-iodoxybenzoic acid (19.1 mg, 0.635 mmol) was added at 0° C., and the mixture was stirred at room temperature for 8 hours. After the temperature of the reaction mixture was made to drop to 0° C., a saturated NaHCO$_3$ solution was added and then extraction with CH$_2$Cl$_2$ was performed. The organic layer was dried over Na$_2$SO$_4$ and filtered, and the filtrate was concentrated in vacuo. The residue was purified by silica gel column chromatography (n-hexane/AcOEt=1:2) and compound 9 (19 mg, 71% in 2 steps) was obtained.

IR (KBr): 2962, 1672, 852 cm$^{-1}$. [α]$_D$$^{21}$ −3.95 (c 1.07, CHCl$_3$). $^1$H-NMR (500 MHz, CDCl$_3$) δ: 9.26 (1H, s), 8.52 (1H, d, J=5.5 Hz), 7.85 (1H, s), 7.82 (1H, d, J=8.5 Hz), 7.65-7.63 (2H, m), 7.07 (1H, d, J=9.8 Hz), 5.90 (1H, d, J=10.4 Hz), 3.24 (1H, t, J=9.8 Hz), 2.62-2.58 (1H, m), 2.45-2.43 (2H, m), 2.33-2.28 (2H, m), 2.01-1.99 (1H, m), 1.74-1.72 (1H, m), 0.81 (3H, s). ESI MS m/z 278 (M+H)$^+$. HR-ESI MS: m/z 278.1545, calcd for C$_{19}$H$_{20}$NO. Found: 278.1544.

(8) Synthesis of compound 10 (1R,3aS,7aS)-1-(isoquinolin-7-yl)-7a-methyl-2,3,3a,7a-tetrahydro-1H-inden-5-yltrifluoromethanesulfonate)

To a THF solution (3.6 mL) of compound 9 (100 mg, 0.361 mmol), phenyl-N-triflimide (258 mg, 1.12 mmol) and KHMDS (0.5 M in toluene, 2.25 mL, 1.12 mmol) were added at −78° C., and the mixture was stirred for 30 minutes. After the temperature of the reaction mixture was made to rise to 0° C., water was added and then extraction with AcOEt was performed. The organic layer was dried over Na$_2$SO$_4$ and filtered, and the filtrate was concentrated in vacuo. The residue was purified by silica gel column chromatography (n-hexane/AcOEt=1:1) and compound 10 (138 mg, 94%) was obtained.

IR (KBr): 2964, 1419, 1211, 1141 cm$^{-1}$. $^1$H-NMR (500 MHz, CDCl$_3$) δ: 9.22 (1H, s), 8.51 (1H, d, J=6.1 Hz), 7.83 (1H, s), 7.80 (1H, d, J=8.5 Hz), 7.64-7.62 (2H, m), 6.26 (1H, d, J=9.8 Hz), 5.92 (1H, t, J=2.5 Hz), 5.79 (1H, dd, J=9.8, 2.2 Hz), 3.31 (1H, t, J=10.1 Hz), 3.04-2.99 (1H, m), 2.37-2.34 (2H, m), 2.03-2.01 (1H, m), 1.88-1.86 (1H, m), 0.67 (3H, s). ESI MS: m/z 410 (M+H)$^+$. HR-ESI MS: m/z 410.1038, calcd for C$_{20}$H$_{19}$NO$_3$F$_3$S. Found: 410.1024.

(9) Synthesis of compound 11 ((1R,3aS,7aS)-methyl 1-(isoquinolin-7-yl)-7a-methyl-2,3,3a,7a-tetrahydro-1H-indene-5-carboxylate)

To a DMF solution (20 mL) of compound 10 (265 mg, 0.648 mmol), Pd(PPh$_3$)$_4$ (75 mg 0.0648 mmol), MeOH (8.3 mL) and Et$_3$N (1.45 mL, 9.72 mmol) were added at room temperature, and the mixture was stirred under carbon monoxide atmosphere at 40° C. for 3 hours. After the temperature of the reaction mixture was made to drop to 0° C., water was added and then extraction with AcOEt was performed. The organic layer was dried over Na$_2$SO$_4$ and filtered, and the filtrate was concentrated in vacuo. The residue was purified by silica gel column chromatography (n-hexane/AcOEt=1:1) and compound 11 (200 mg, 98%) was obtained.

IR (KBr): 2955, 1714, 1267 cm$^{-1}$. [α]$_D$$^{19}$ −88.6 (c 1.51, CHCl$_3$). $^1$H-NMR (500 MHz, CDCl$_3$) δ: 9.24 (1H, s), 8.50 (1H, d, J=6.1 Hz), 7.84 (1H, s), 7.79 (1H, d, J=8.5 Hz), 7.64 (2H, dd, J=12.2, 3.7 Hz), 7.13 (1H, s), 6.34 (1H, d, J=9.8 Hz), 6.17 (1H, d, J=9.8 Hz), 3.77 (3H, s), 3.31 (1H, t, J=9.8 Hz), 2.93-2.91 (1H, m), 2.39-2.33 (2H, m), 2.09-2.02 (1H, m), 1.89-1.88 (1H, m), 0.58 (3H, s) ESI MS: m/z 320 (M+H)$^+$. HR-ESI MS: m/z 320.1651, calcd for C$_{21}$H$_{22}$NO$_2$. Found: 320.1643.

(10) Synthesis of compound 12 ((1R,3aS,7aS)-1-(isoquinolin-7-yl) 7a-methyl-2,3,3a,7a-tetrahydro-1H-indene-5-carbaldehyde)

To a CH$_2$Cl$_2$ solution (13 mL) of compound 11 (54.2 mg, 0.188 mmol), DIBAL-H (1.0 M in n-hexane, 0.56 mL, 0.56 mmol) was added at −78° C., and the mixture was stirred for 15 minutes. After the temperature of the reaction mixture was made to rise to 0° C., a 15% NaOH aqueous solution was added. The reaction mixture was filtered through Celite and the filtrate was concentrated in vacuo. In this way, a crude product (49 mg) containing ((1R,3aS,7aS)-1-(isoquinolin-7-yl)-7a-methyl-2,3,3a,7a-tetrahydro-1H-inden-5-yl)methanol was obtained. To a CH$_2$Cl$_2$ solution (3.4 mL) of the obtained crude product, Dess-Martin periodinane (107 mg, 0.254 mmol) and NaHCO$_3$ (71 mg, 0.847 mmol) were added at 0° C., and the mixture was stirred at room temperature for 30 minutes. After the temperature of the reaction mixture was made to drop to 0° C., a saturated NaHCO$_3$ solution was added and then extraction with CH$_2$Cl$_2$ was performed. The organic layer was dried over Na$_2$SO$_4$ and filtered, and the filtrate was concentrated in vacuo. The residue was purified by silica gel column chromatography n-hexane/AcOEt=1:4) and compound 12 (38 mg, 67% in 2 steps) was obtained.

$^1$H-NMR (500 MHz, CDCl$_3$) δ: 9.44 (1H, s), 9.25 (1H, s), 8.50 (1H, d, J=5.5 Hz), 7.85 (1H, s), 7.80 (1H, d, J=8.5 Hz), 7.66-7.64 (2H, m), 6.95 (1H, s), 6.37 (1H, d, J=9.8 Hz), 6.23 (1H, d, J=9.8 Hz), 3.35 (1H, t, J=9.8 Hz), 3.05 (1H, t, J=10.0 Hz), 2.41-2.36 (2H, m), 2.08 (1H, s), 1.98-1.96 (1H, m), 0.58 (3H, s). ESI MS: m/z 290 (M+H)$^+$.

(11) Synthesis of objective compound 1 (CA-1, (3R, 3aR,11aS,11bR)-3-(isoquinolin-7-yl)-3a-methyl-1,2, 3,3a,9,10,11a,11b-octahydrocyclopenta[c]xanthen-7 (8H)-one)

To an AcOEt solution (4.0 mL) of compound 12 (12 mg, 0.0415 mmol), 3-cyclohexanedione (11 mL, 0.083 mmol) and ethylenediamine (3.6 ml 0.0498 mmol) were added at 0° C., and the mixture was stirred at room temperature for 3 hours. After the temperature of the reaction mixture was made to drop to 0° C., water was added and then extraction with CH$_2$Cl$_2$ was performed. The organic layer was dried over Na$_2$SO$_4$ and filtered, and the filtrate was concentrated in vacuo. The residue was purified by silica gel column chromatography (n-hexane/AcOEt=1:4) and compound 1 (15 mg, 97%) was obtained.

IR (KBr): 2959, 1653, 1582, 1375 cm$^{-1}$. [α]$_D$$^{19}$ −101.7 (c 1.24, CHCl$_3$). $^1$H-NMR (500 MHz, CDCl$_3$): 9.26 (1H, s), 8.51 (1H, d, J=5.5 Hz), 7.85 (1H, s), 7.80 (1H, d, J=8.5 Hz), 7.65 (2H, t, J=6.4 Hz), 6.37 (1H, s), 6.05 (1H, d, J=9.2 Hz), 5.90 (1H, d, J=9.2 Hz), 4.86 (1H, d, J=11.6 Hz), 3.23 (1H, t, J=9.8 Hz), 2.57-2.28 (4H, m), 2.03-2.02 (2H, m), 1.84-1.81 (1H, m), 1.61-1.59 (1H, m), 1.20 (1H, m), 0.93-0.90 (2H, m), 0.68 (3H, s). ESI MS: m/z 384 (M+H)$^+$.

Example 2

Evaluation of Selective Anti-Proliferative Activity Against Vascular Endothelial Cells (1)

CA-1, which is represented by formula (II), was used as test compound, and an existing anticancer drug doxorubicin was used as a control compound. The test compound and the control compound were separately dissolved at predetermined concentrations in EtOH. The cells used were normal human umbilical vein endothelial cells (HUVEC) and human pharyngeal carcinoma KB3-1 cells.

HUVEC and KB3-1 were seeded in separate 96-well multiwell plates at 2×10$^3$ cells/100 μL/well and cultured in an atmosphere of 5% CO$_2$ at 37° C. for 24 hours. Next, 1.0 μL each of the ethanol solutions containing the test compound or the control compound at various concentrations were added, and the cells were cultured under the same conditions for additional 72 hours. After 72 hours, 10 μL of WST-8 (2-(2-methoxy-4-nitrophenyl)-3-(4-nitrophenyl)-5-(2,4-disulfophenyl)-2H-tetrazolium, monosodium salt) reagent was added. After 3-hour incubation, the amount of water-soluble formazan formed in viable cells was calorimetrically determined by measurement at OD 450 nm, and the growth inhibition ratio was calculated by comparison of the amount of formazan between the compound treatment groups and the non-treatment group. The anti-proliferative activities of the test compound and the control compound on each type of cells were expressed as a 50% growth inhibitory concentration ($IC_{50}$ value). The cell type selectivity (Selective Index (S.I.) value) was expressed as a value resulting from division of the $IC_{50}$ value against KB3-1 by the $IC_{50}$ value against HUVEC.

The results are shown in Table 1. The $IC_{50}$ value of the test compound CA-1 was 0.1 μM against. HUVEC and 10.5 μM against KB3-1. The S.I. value was 105. On the other hand, the $IC_{50}$ value of the control compound doxorubicin was 0.13 μM against HUVEC and 0.36 μM against KB3-1, and the S.I. value was as low as 2.7. Therefore, doxorubicin has little selectivity in cell type. These results demonstrate that the test compound CA-1 selectively inhibits the growth of vascular endothelial cells, a key player in angiogenesis.

TABLE 1

|  | CA-1 | | doxorubicin | |
| --- | --- | --- | --- | --- |
|  | $IC_{50}$ | S.I. | $IC_{50}$ | S.I. |
| HUVEC | 0.1 |  | 0.13 |  |
| KB3-1 | 10.5 | 105 | 0.36 | 2.7 |

Example 3

Evaluation, of In Vivo Anti-Angiogenic Activity after Intraperitoneal Administration The test compound CA-1 was suspended at predetermined concentrations in 1% CMC. To control groups, the vehicle (1% CMC) was administered.

To 500 μL of Matrigel (trade name, manufactured by BD), 200 ng/mL of a proangiogenic factor bFGF (basic fibroblast growth factor) and 100 U/mL of heparin were added, and the mixture was subcutaneously injected into the flanks of female ddY mice (6-week old) with an injection needle of 23G. After the Matrigel injection, the test compound CA-1 or the vehicle (1% CMC) was intraperitoneally administered on a schedule of once every two days, 5 times in total. Aside from this, Matrigel without bFGF was injected into a group of mice and then the vehicle was administered thereto (negative control group). The anti-angiogenic effect was evaluated as follows: the day after the final administration of the test compound, the implanted Matrigel was harvested and weighed, and then the amount of hemoglobin accumulated in the Matrigel was compared between the test compound administration groups and the control groups. Significance analysis was performed using a Dunnett's test at a significance level of 5%.

Figure 2:
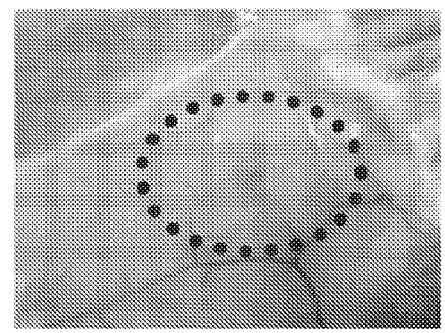
FIG. 2 shows images of the Matrigel injection sites in representative mice of all different groups in the test for in vivo anti-angiogenic activity after intraperitoneal administration of the compound represented by formula (II) (CA-1).
Figure 2:
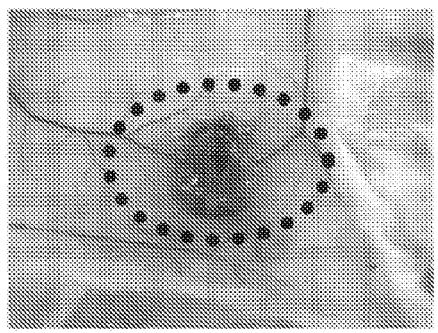
Figure 2:
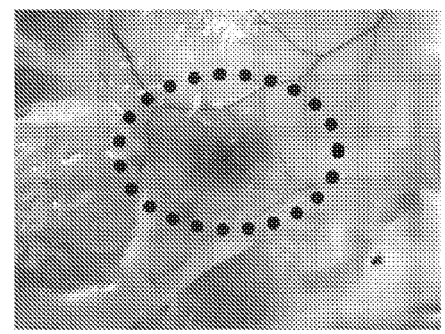
Figure 2:
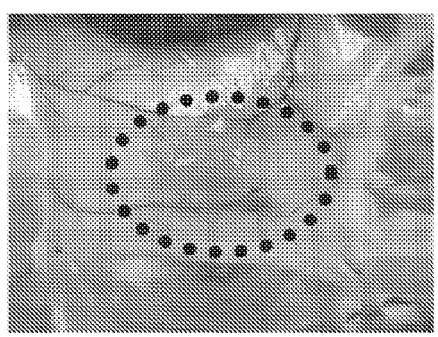
Figure 3:
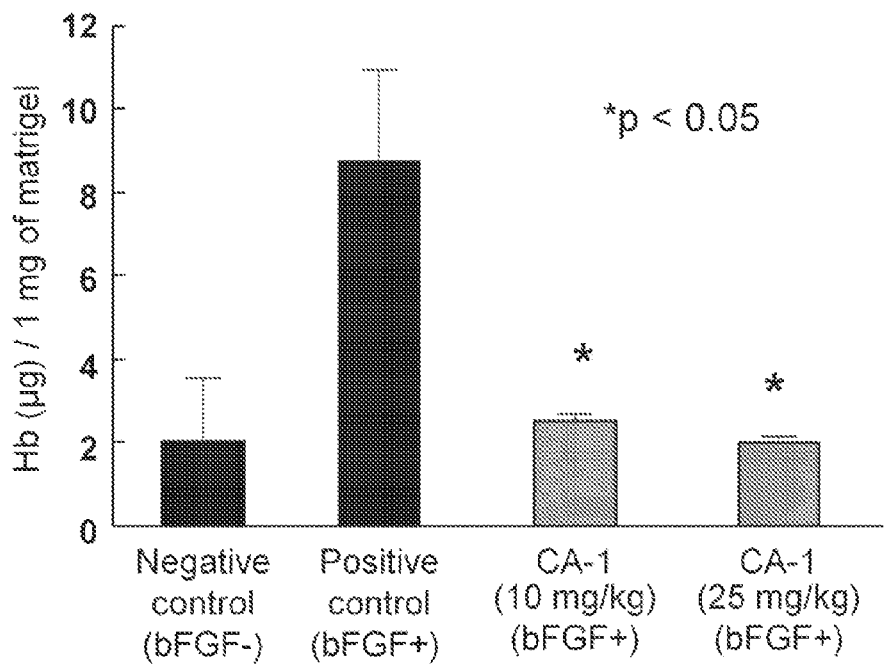
FIG. 3 shows a graph representing the measured amount of hemoglobin accumulated in the Matrigel subcutaneously injected into mice in the test for in vivo anti-angiogenic activity after intraperitoneal administration of the compound represented by formula (II) (CA-1).

The results are shown in FIGS. 2 and 3. FIG. 2 shows images of the Matrigel injection sites in representative mice of all different groups, and FIG. 3 shows a graph representing the measured amount of hemoglobin accumulated in the Matrigel. As is clear from FIGS. 2 and 3, CA-1 administered at not less than 10 mg/kg significantly reduced the amount of hemoglobin accumulated in the Matrigel to almost the same level as that of the group injected with Matrigel not supplemented with the proangiogenic factor bFGF. These results demonstrate that the test compound CA-1 has in vivo anti-angiogenic effect.

Example 3

Evaluation of Antitumor Activity in Mouse Cancer Cell Transplant Model after Intraperitoneal Administration The test compound CA-1 was suspended at predetermined concentrations in 1% CMC. The vehicle (1% CMC) was administered to the control group.

Mouse sarcoma S180 cells were suspended at $1 \times 10^7$ cells/mL in a serum-free RPMI culture medium and the suspension was kept on ice. Then, the S180 cell suspension was subcutaneously inoculated at $1 \times 10^6$ cells/100 μL/mouse into the flanks of female ddY mice (5-week old) with an injection needle of 23G. The mice were maintained for one week for engraftment of the S180 cells. Subsequently, the test compound (5 mg/kg, 10 mg/kg and 25 mg/kg) or the vehicle (1% CMC) was intraperitoneally administered on a schedule of on every two days, 7 times in total. The antitumor activity was evaluated as follows: one day after the final administration, tumors were isolated and weighed, and then the tumor weight was compared between the test compound administration groups and the control group.

Figure 4:
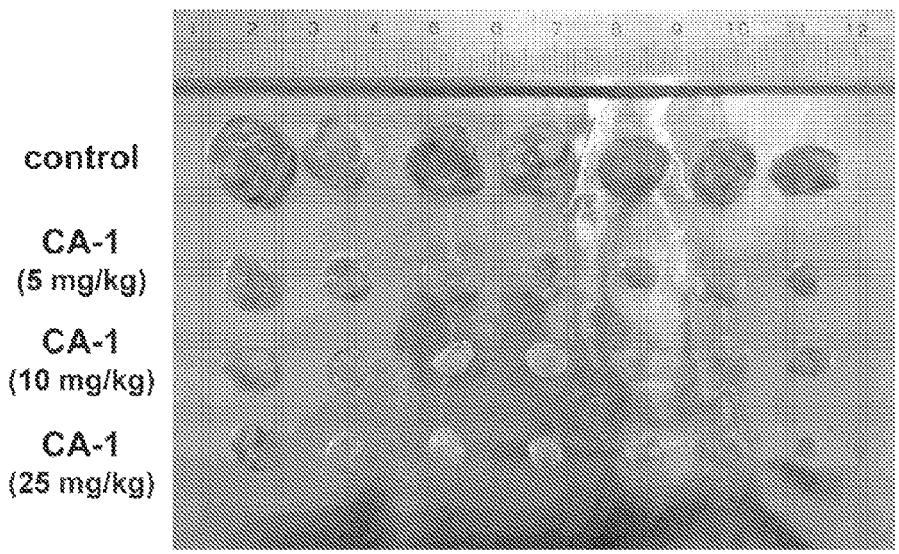
FIG. 4 shows an image for size comparison of tumors isolated from the mice of all groups in the test for antitumor activity in a mouse cancer cell transplant model after intraperitoneal administration of the compound represented by formula (II) (CA-1).
Figure 5:
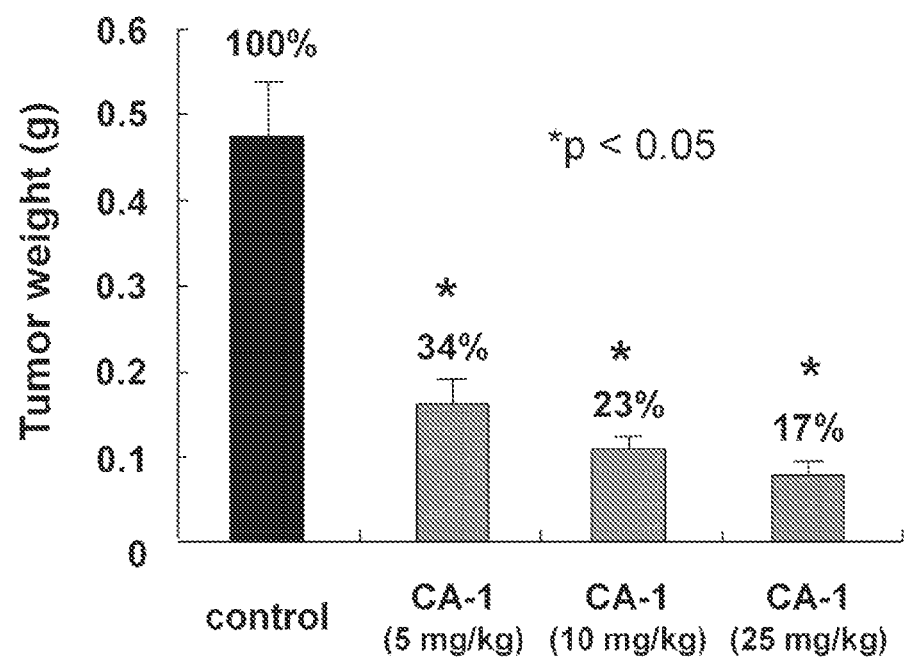
FIG. 5 shows a graph representing the measurement results of the tumor weight in the test for antitumor activity in a mouse cancer cell transplant model after intraperitoneal administration of the compound represented by formula (II) (CA-1).

The results are shown in FIGS. 4 and 5. FIG. 4 shows an image for size comparison of tumors isolated from the mice of all groups, and FIG. 5 shows a graph representing the measurement results of the tumor weight. As is clear from FIGS. 4 and 5, the tumor weights of the 5 mg/kg, 10 mg/kg and 25 mg/kg CA-1 administration on groups were reduced to 34%, 23% and 17% of that of the control group, respectively. Thus, CA-1 was shown to have marked antitumor activity. In no groups, weight loss or diarrhea, or visual abnormalities in organs of the mice were observed.

Example 4

Synthesis of Compounds Represented by Formulae (XVIII), (XIX) and (XXIII)

Figure 6:
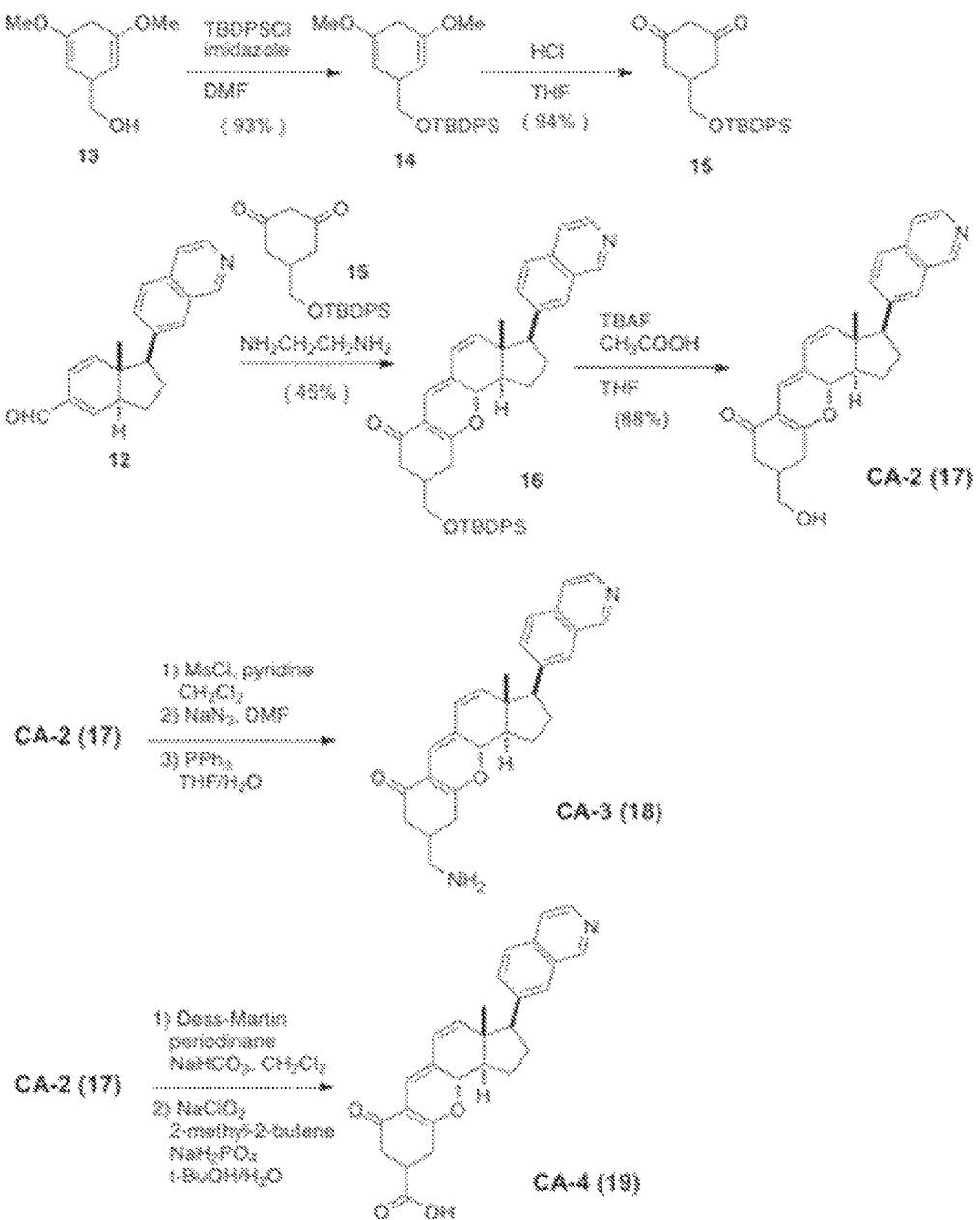
FIG. 6 shows the synthesis schemes of the compounds represented by formulae (XVIII), (XIX) and (XXIII) (CA-2, CA-3 and CA-4).

According to the schemes shown in FIG. 6, the compound represented by formula (XVIII) (hereinafter referred to as "CA-2"), the compound represented by formula (XIX) (hereinafter referred to as "CA-3"), and the compound represented by formula (XXIII) (hereinafter referred to as "CA-4") were synthesized.

(1) Synthesis of compound 14 (tert-butyl((3,5-dimethoxycyclohexa-2,5-dien-1-yl)methoxy)-diphenylsilane)

To a DMF solution (1.0 mL) of compound 13 (17 mg, 0.098 mmol) imidazole (33 mg, 0.48 mmol) and TBDPSCl (80 μL, 0.31 mmol) were added at 0° C., and the mixture was stirred at 0° C. for 30 minutes. To this, a saturated aqueous $NH_4Cl$ solution was added and then extraction with $CHCl_3$ was performed. The organic layer was dried over $Na_2SO_4$ and filtered, and the filtrate was concentrated in vacuo. The residue was purified by silica gel column chromatography (n-hexane/AcOEt=10:1) and compound 14 (37.5 mg, 93%) was obtained.

¹H-NMR (500 MHz, CDCl₃) δ: 7.71-7.69 (4H, m), 7.44-7.37 (6H, m), 4.73 (2H, d, J=3.0 Hz), 3.56 (6H, s), 3.55 (2H, d, J=7.5 Hz), 3.26-3.19 (1H, m), 2.84-2.74 (2H, m), 1.09 (9H, s).

(2) Synthesis of compound 15 (5-(((tert-butyldiphenylsilyl)oxy)methyl)cyclohexane-1,3-dione)

To a THF solution (2.8 mL) of compound 14 (227 mg, 0.56 mmol) 1 M HCl (0.55 mL) was added, and the mixture was stirred at room temperature for 1 hour. The reaction mixture was diluted with acetone and toluene, and then concentrated in vacuo. In this way, compound 15 (198 mg, 94%) was obtained.

¹H-NMR (500 MHz, CDCl₃) δ: 7.71-7.69 (4H, m) 7.44-7.37 (6H, m), 3.65-3.30 (3H, m), 2.75-2.30 (4H, m).

(3) Synthesis of compound 16 ((3R,3aR,11aS,11bR)-9-(((tert-butyldiphenylsilyl)oxy)methyl)-3-(isoquinolin-7-yl)-3a-methyl-1,3,3a,8,9,10,11a,11b-octahydrocyclopenta[c]xanthen-7(2H)-one)

To an AcOEt/CH₂Cl₂ solution (1:3, 8.0 mL) of compound 12 (see Example 1 and FIG. 1, 56 mg, 0.19 mmol), compound 15 (1.34 mg, 0.35 mmol) and ethylenediamine (16 µL, 0.23 mmol) were added at 0° C., and the mixture was stirred at room temperature for 10 hours. After the temperature of the reaction mixture was made to drop to 0° C., water was added and then extraction with CH₂Cl₂ was performed. The organic layer was dried over Na₂SO₄ and filtered, and the filtrate was concentrated in vacuo. The residue was purified by silica gel column chromatography (n-hexane/AcOEt=1:1) and compound 16 (57 mg, 45%) was obtained as a diastereomeric mixture (1:1).

¹H-NMR (500 MHz, CDCl₃) δ: 9.25 (1H, s), 8.51 (1H, d, J=5.5 Hz), 7.85 (1H, s), 7.80 (1H, d, J=8.5 Hz), 7.67-7.62 (5H, m), 7.47-7.35 (7H, m), 6.37 (½H, brs), 6.34 (½H, brs), 6.05 (1H, dd, J=10.0, 1.0 Hz), 5.90 (1H, d, J=10.0 Hz), 4.89 (½H, dd, 12.0, 2.0 Hz), 4.87 (½H, dd, 2.0 Hz), 3.67-3.57 (2H, m), 3.23 (1H, t, J=10.0 Hz), 2.60-2.20 (9H, m), 1.87-1.78 (1H, m), 1.08 (9/2H, s), 1.07 (9/2H, s), 0.69 (3H, s).

(4) Synthesis of compound 17 (CA-2, (3R,3aR,11aS,11bR)-9-(hydroxymethyl)-3-(isoquinolin-7-yl)-3a-methyl-1,3,3a,8,9,10,11a,11b-octahydrocyclopenta[c]xanthen-7(2H)-one)

To a THF solution (0.7 mL) of compound 16 (42 mg, 0.066 mmol) TBAF (1.0 M in THF, 0.13 mL, 0.13 mmol) and CH₃COOH (4 µL) were added at 0° C., and the mixture was stirred at room temperature overnight. To this, a saturated brine and a saturated aqueous NaHCO₃ solution were added and then extraction with CH₂Cl₂ was performed. The organic layer was dried over Na₂SO₄ and filtered, and the filtrate was concentrated in vacuo. The residue was purified by silica gel column chromatography (AcOEt and AcOEt/MeOH=10:1) and compound 17 (24.3 mg, 88%) was obtained as a diastereomeric mixture (1:1).

¹H-NMR (500 MHz, CDCl₃) δ: 9.25 (1H, s), 8.51 (1H, d, J=5.5 Hz), 7.85 (1H, s), 7.80 (1H, d, J=8.5 Hz), 7.66-7.63 (2H, m), 6.36 (½H, brs), 6.35 (½H, brs), 6.05 (½H, d, J=9.0 Hz), 6.04 (½H, d, J=9.0 Hz), 5.91 (½H, d, J=9.0 Hz), 5.90 (½H, d, J=9.0 Hz), 4.89 (½H, dd, J=12.0, 2.0 Hz), 4.85 (½H, dd, J=12.0, 2.0 Hz), 3.67-3.57 (3H, m), 3.23 (1H, t, J=10.0 Hz), 2.60-2.20 (9H, m), 1.87-1.78 (1H, m), 0.68 (3H, s).

(5) Synthesis of compound 18 (CA-3, (3R,3aR,11aS,11bR)-9-(aminomethyl)-3-(isoquinolin-7-yl)-3a-methyl-1,3,3a,8,9,10,11a,11b-octahydrocyclopenta[c]xanthen-7(2H)-one)

To a CH₂Cl₂ solution (0.2 mL) of compound 17 (4.2 mg, 0.01 mmol), MsCl (4 µL, 0.05 mmol) and Et₃N (8 µL, 0.10 mmol) were added at 0° C., and the mixture was stirred at room temperature for 5 hours. To this, water was added and then extraction with CH₂Cl₂ was performed. The organic layer was dried over Na₂SO₄ and filtered, and the filtrate was concentrated in vacuo. To a DMF solution (0.2 mL) of the residue, NaN₃ (6.4 mg, 0.10 mmol) was added, and the mixture was stirred at room temperature for 3 days. To this, water was added and then extraction with CH₂Cl₂ was performed. The organic layer was dried over Na₂SO₄ and filtered, and the filtrate was concentrated in vacuo. To a THF/water solution (0.4 mL+0.1 mL) of the residue, PPh₃ (8.0 mg, 0.07 mmol) was added, and the mixture was stirred at room temperature for 5 hours. To this, water was added and then extraction with CH₂Cl₂ was performed. The organic layer was dried over Na₂SO₄ and filtered, the filtrate was concentrated in vacuo. The residue was purified by silica gel column chromatography (AcOEt and CH₂Cl₂/MeOH=10:1) and compound 18 (2.3 mg, 42%) was obtained as a diastereomeric mixture (1:1).

¹H-NMR (500 MHz, CDCl₃) δ: 9.25 (1H, s), 8.51 (1H, d, J=5.5 Hz), 7.84 (1H, s), 7.80 (1H, d, J=8.5 Hz), 7.66-7.63 (2H, m), 6.33 (1H, brs), 6.03 (1H, d, J=9.5 Hz), 5.91 (1H, d, J=9.0 Hz), 4.85 (1H, d, J=13.0 Hz), 3.65 (2H, brs), 3.23-3.16 (3H, m), 2.60-2.20 (9H, m), 1.87-1.78 (1H, m), 0.67 (3H, s).

(6) Synthesis of compound 19 (CA-4, (3R,3aR,11aS,11bR)-3-(isoquinolin-7-yl)-3a-methyl-7-oxo-1,2,3a,7,8,9,10,11a,11b-decahydrocyclopenta[c]xanthene-9-carboxylic acid)

To a CH₂Cl₂ solution (0.3 mL) of compound 17 (4.5 mg, 0.011 mmol), Dess-Martin periodinane (6.9 mg, 0.016 mmol) and NaHCO₃, (3.7 mg, 0.044 mmol) were added at 0° C., and the mixture was stirred at room temperature for 1 hour. After the temperature of the reaction mixture was made to drop to 0° C., a saturated Na₂S₂O₃ solution was added and then extraction with CH₂Cl₂ was performed. The organic layer was dried over Na₂SO₄ and filtered, and the filtrate was concentrated in vacuo. To a t-BuOH solution (0.2 mL) of the residue, NaClO₂ (3.0 mg, 0.033 mmol), 2-methyl-2-butene (70 µL) and an aqueous NaH₂PO₄ solution (20%, 0.2 mL) were added, and the mixture was stirred at room temperature for 2 hours. After the temperature of the reaction mixture was made to drop to 0° C., water was added and then extraction with CH₂Cl₂ was performed. The organic layer was dried over Na₂SO₄ and filtered, the filtrate was concentrated in vacuo. The residue was purified by silica gel column chromatography (AcOEt and CH₂Cl₂/MeOH=5:1) and compound 19 (1.1 mg, 25% in 2 steps) was obtained as a diastereomeric mixture (1:1).

¹H-NMR (500 MHz, CDCl₃) δ: 9.28 (1H, brs), 8.50 (1H, d, J=6.0 Hz), 7.87 (1H, s), 7.81 (1H, d, J=8.5 Hz), 7.67-7.63 (2H, m), 6.35 (1H, brs), 6.03 (1H, d, J=9.5 Hz), 5.91 (1H, d, J=9.0 Hz), 4.88 (1H, d, J=11.0 Hz), 3.23-3.16 (2H, m), 2.60-2.20 (8H, m), 1.87-1.78 (1H, m), 0.67 (3H, s).

Example 5

Synthesis of Compound Represented by Formula (LIV)

Figure 7:
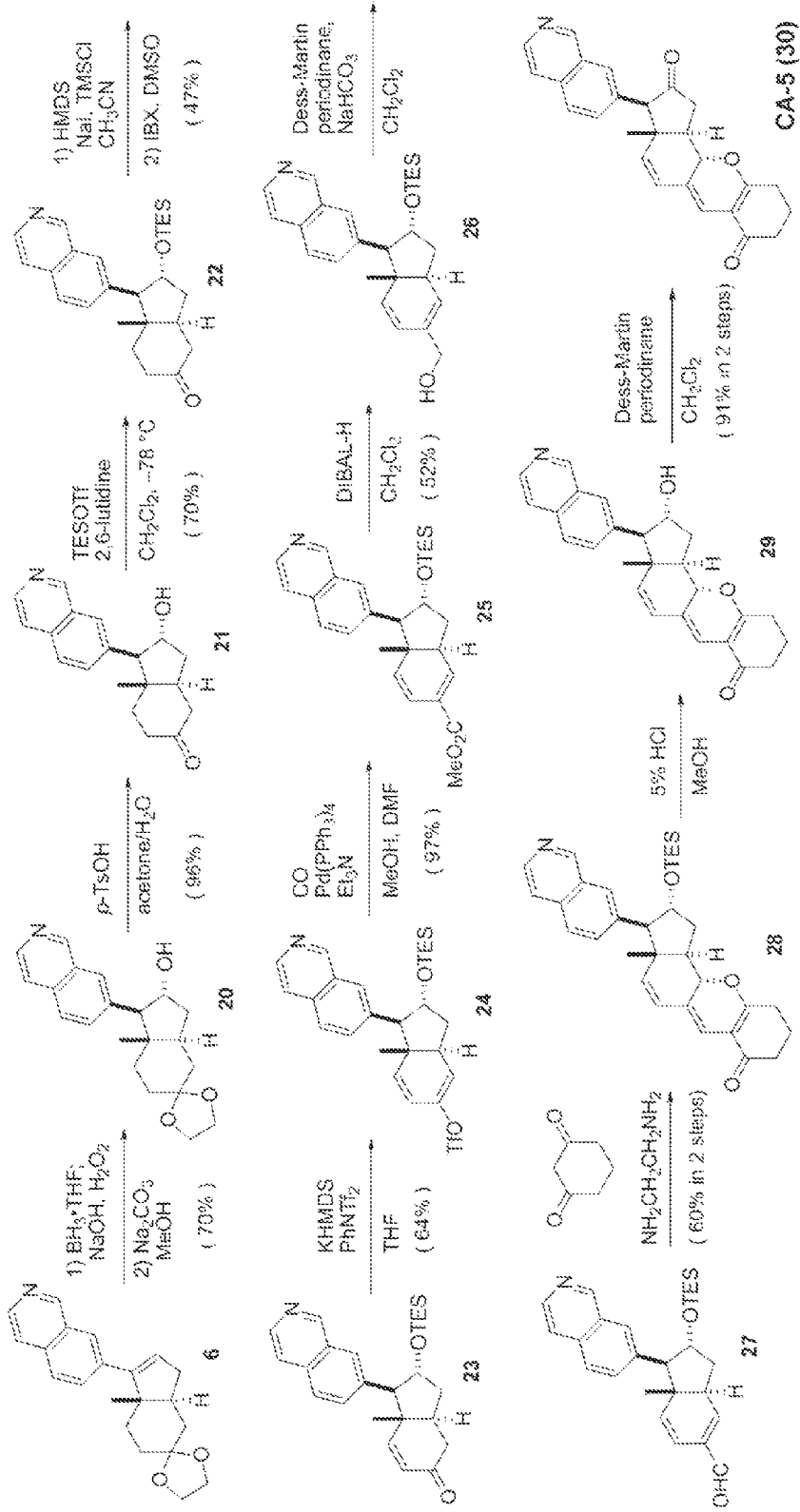
FIG. 7 shows the synthesis scheme of the compound represented by formula (LIV) (CA-5).

According to the scheme shown in FIG. 7, the compound represented by formula (LIV) (hereinafter referred to as "CA-5") was synthesized.

(1) Synthesis of compound 20 (((1'S,2'R,3a'S,7a'S)-(isoquinolin-7-yl)-7a'-methyloctahydrospiro[[1,3] dioxolane-2,5'-inden]-2'-ol)

$BH_3$·THF (1.0 M in THF, 3.3 mL, 3.3 mmol) was added to a THF solution (13.6 mL) of compound 6 (see Example 1 and FIG. 1, 350 mg, 1.09 mmol), and the mixture was stirred at room temperature for 4 hours. After the temperature of the reaction mixture was made to drop to 0° C., a 2 N NaOH aqueous solution (17 mL) and a 30% $H_2O_2$ aqueous solution (17 mL) were added. The mixture was stirred at room temperature for 3 days and then extraction with $CH_2Cl_2$ was performed. The organic layer was dried over $Na_2SO_4$ and filtered, and the filtrate was concentrated in vacuo. The residue was dissolved in MeOH (10 mL) and $Na_2CO_3$ (800 mg) was added thereto. After the mixture was heated under reflux for 7 hours, the insoluble matter was filtered off and the filtrate was concentrated in vacuo. The residue was purified by silica gel column chromatography ($CHCl_3$/MeOH/$H_2O$=30:3:1 (lower phase)) and compound 20 (258 mg, 70%) was obtained.

$^1$H-NMR (500 MHz, $CDCl_3$) δ: 9.17 (1H, s), 8.46 (1H, d, J=6.5 Hz), 7.79 (1H, s), 7.76 (1H, d, J=8.5 Hz), 7.61 (1H, d, J=6.5 Hz), 7.56 (1H, dd, J=8.5, 1.5 Hz), 5.01 (1H, td, J=9.0, 1.5 Hz), 4.00-3.95 (4H, m), 2.90 (1H, d, J=7.5 Hz), 2.46-2.38 (1H, m), 2.02 (1H, td, J=13.0, 8.5 Hz), 1.80-1.43 (7H, m), 0.63 (3H, s).

(2) Synthesis of compound 21 (((1S,2R,3aS,7aS)-2-hydroxy-1-(isoquinolin-7-yl)-7a-methyl-hexahydro-1H-inden-5(6H)-one)

To an acetone/water solution (10 mL 2 mL) of compound 20 (209 mg, 0.62 mmol), p-toluenesulfonic acid monohydrate (293 mg, 1.54 mmol) was added, and the mixture was stirred at 70° C. for 5 hours. After the temperature of the reaction mixture was made to drop to 0° C., a saturated $NaHCO_3$ solution was added and then extraction with $CHCl_3$ was performed. The organic layer was dried over $Na_2SO_4$ and filtered, and the filtrate was concentrated in vacuo. The residue was purified by silica gel column chromatography ($CHCl_3$/MeOH/$H_2O$=30:3:1 (lower phase)) and compound 21 (174 mg, 96%) was obtained.

$^1$H-NMR (500 MHz, $CDCl_3$) δ: 9.24 (1H, s), 8.51 (1H, d, J=5.5 Hz), 7.85 (1H, s), 7.82 (1H, d, J=8.5 Hz), 7.65 (1H, d, J=5.5 Hz), 7.59 (1H, dd, J=8.5, 1.5 Hz), 5.10 (1H, td, J=9.0, 1.5 Hz), 3.64 (1H, s), 2.97 (1H, d, J=8.0 Hz), 2.53-2.26 (5H, m), 2.15-2.08 (1H, m), 1.91 (1H, ddd, J=14.5, 8.0, 2.0 Hz), 1.85 (1H, td, J=12.0, 5.5 Hz), 1.75 (1H, ddd, J=12.0, 6.5, 1.5 Hz), 0.83 (3H, s).

(3) Synthesis of compound 22 (((1S,2R,3aS,7aS)-1-(isoquinolin-7-yl)-7a-methyl-2-((triethylsilyl)oxy) hexahydro-1H-inden-5(6H)-one)

To a $CH_2Cl_2$ solution (7.3 mL) of compound 21 (214 mg, 0.73 mmol) TESOTf (180 μL, 0.80 mmol) and 2,6-lutidine (110 μL, 0.95 mmol) were added at −78° C., and the mixture was stirred at −78° C. for 20 minutes. To this, a saturated $NH_4Cl$ solution was added and then extraction with $CHCl_3$ was performed. The organic layer was dried over $Na_2SO_4$ and filtered, and the filtrate was concentrated in vacuo. The residue was purified by silica gel column chromatography ($CHCl_3$/MeOH/$H_2O$=100:3:1 (lower phase)) and compound 22 (207 mg, 70%) was obtained.

$^1$H-NMR (500 MHz, $CDCl_2$) δ: 9.25 (1H, s), 8.52 (1H, d, J=5.5 Hz), 7.81-7.78 (2H, m), 7.65 (1H, d, J=6.0 Hz), 7.58 (1H, dd, J=8.5, 1.5 Hz), 4.95 (1H, td, J=9.0, 2.0 Hz), 2.98 (1H, d, J=7.5 Hz), 2.51-2.24 (5H, m), 2.04 (1H, td, J=12.5, 8.5 Hz), 1.87-1.78 (2H, m), 1.69 (1H, ddd, J=13.0, 7.5, 2.0 Hz), 0.83 (3H, s), 0.74 (9H, t, J=8.0 Hz), 0.46-0.31 (6H, m).

(4) Synthesis of compound 23 (((1R,2R,3aS,7aR)-1-(isoquinolin-7-yl)-7a-methyl-2-((triethylsilyl)oxy)-2,3,3a,4-tetrahydro-1H-inden-5(7aH)-one)

To a $CH_2CN$ solution (7.5 mL) of compound 22 (154 mg, 0.38 mmol), HMDS (0.8 mL, 3.82 mmol), NaI (280 mg, 1.87 mmol) and TMSCl (0.24 ml, 1.89 mmol) were added at 0° C., and the mixture was stirred at room temperature for 1 hour. After the temperature of the reaction mixture was made to drop to 0° C., a saturated $NH_4Cl$ solution was added and then extraction with $CH_2Cl_2$ was performed. The organic layer was dried over $Na_2SO_4$ and filtered, and the filtrate was concentrated in vacuo. To a DMSO solution (7.5 mL) of the resulting product, 2-iodoxybenzoic acid (210 mg, 0.75 mmol) was added at 0° C., and the mixture was stirred at room temperature for 9 hours. After the temperature of the reaction mixture was made to drop to 0° C., a saturated $NaHCO_3$ solution and a saturated $Na_2S_2O_3$ solution were added and then extraction with $CH_2Cl_2$ was performed. The organic layer was dried over $Na_2SO_4$ and filtered, and the filtrate was concentrated in vacuo. The residue was purified by silica gel column chromatography (n-hexane/AcOEt=1:1) and compound 23 (72 mg, 47%) was obtained.

$^1$H-NMR (500 MHz, $CDCl_3$) δ: 9.25 (1H, s), 8.52 (1H, d, J=5.5 Hz), 7.84-7.80 (2H, m), 7.66 (1H, d, J=5.5 Hz), 7.61 (1H, dd, J=8.5, 1.5 Hz), 6.96 (1H, d, j=14.5 Hz), 5.86 (1H, d, J=14.5 Hz), 4.88 (1H, t, J=7.0 Hz), 3.16 (1H, d, J=7.0 Hz), 2.87-2.78 (1H, m), 2.63 (1H, dd, J=17.5, 4.0 Hz), 2.41 (1H, dd, J=17.5, 15.0 Hz), 2.16 (1H, td, J=13.5, 8.5 Hz), 1.90 (1H, dd, J=13.5, 7.5 Hz), 0.86 (3H, s), 0.73 (9H, t, J=8.0 Hz), 0.46-0.31 (6H, m).

(5) Synthesis of compound 24 (((1R,2R,3aS,7aS)-1-(isoquinolin-7-yl)-7a-methyl-2-((triethylsilyl)oxy)-2,3,3a,7a-tetrahydro-1H-inden-5-yltrifluoromethane-sulfonate)

To a THF solution (4.2 ml) of compound 23 (85.5 mg, 0.21 mmol), phenyl-N-triflimide (300 mg, 0.84 mmol) and KHMDS (0.5 M in toluene, 1.7 mL, 0.85 mmol) were added at −78° C., and the mixture was stirred for 150 minutes. After the temperature of the reaction mixture was made to rise to 0° C., water was added and then extraction with AcOEt was performed. The organic layer was dried over $Na_2SO_4$ and filtered, and the filtrate was concentrated in vacuo. The residue was purified by silica gel column chromatography (n-hexane/AcOEt=3:1) and compound 24 (72 mg, 64%) was obtained.

$^1$H-NMR (500 MHz, $CDCl_3$) δ: 9.25 (1H, s), 8.51 (1H, d, J=6.0 Hz), 7.84 (1H, s), 7.83 (1H, d, J=8.5 Hz), 7.69 (1H, d, J=6.5 Hz), 7.62 (1H, d, J=8.5 Hz), 6.16 (1H, d, J=10.0 Hz), 5.90 (1H, s), 5.77 (1H, dd, J=10.0, 2.0 Hz), 4.92 (1H, t, J=7.0 Hz), 3.41-3.36 (1H, m), 3.24 (1H, d, J=6.5 Hz), 2.30 (1H, td,

J=13.0, 8.5 Hz), 1.94 (1H, dd, J=13.0, 8.0 Hz), 0.73 (3H, s), 0.73 (9H, t, J=8.0 Hz), 0.46-0.31 (6H, m).

(6) Synthesis of compound 25 ((1R,2R,3aS,7aS)-methyl 1-(isoquinolin-7-yl)-7a-methyl-2-(triethylsilyl)oxy)-2,3,3a,7a-tetrahydro-1H-indene-5-carboxylate)

To a DMF solution (0.5 mL) of compound 24 (8.3 mg, 0.015 mmol) Pd (PPh$_3$)$_4$ (2 mg, 0.002 mmol) MeOH (0.2 mL) and Et$_3$N (0.015 mL, 0.11 mmol) were added at room temperature, and the mixture was stirred under carbon monoxide atmosphere at 40° C. for 1 hour. After the temperature of the reaction mixture was made to drop to 0° C., water was added and then extraction with AcOEt was performed. The organic layer was dried over Na$_2$SO$_4$ and filtered, and the filtrate was concentrated in vacuo. The residue was purified by silica gel column chromatography (n-hexane/AcOEt=2:1) and compound 25 (6.7 mg, 97%) was obtained.

$^1$H-NMR (500 MHz, CDCl$_3$) δ: 9.25 (1H, s), 8.51 (1H, d, J=6.0 Hz), 7.85 (1H, s), 7.81 (1H, d, J=8.5 Hz), 7.67 (1H, d, J=6.5 Hz), 7.63 (1H, d, J=8.5 Hz), 7.10 (1H, d, J=2.5 Hz), 6.32 (1H, d, J=10.0 Hz), 6.05 (1H, d, J=10.0 Hz), 4.93 (1H, t, J=7.0 Hz), 3.77 (3H, s), 3.29 (1H, ddd, J=12.0, 8.5, 2.5 Hz), 3.25 (1H, d, j=6.5 Hz), 2.32 (1H, td, J=13.0, 8.5 Hz), 1.95 (1H, dd, J=13.0, 8.5 Hz), 0.73 (9H, t, J=8.0 Hz), 0.62 (3H, s), 0.46-0.31 (6H, m).

(7) Synthesis of compound 26 (((1R,2R,3aS,7aS)-1-(isoquinolin-7-yl)-7a-methyl-2-((triethylsilyl)oxy)-2, 3,3a,7a-tetrahydro-1H-inden-5-yl)methanol)

To a CH$_2$Cl$_2$ solution (2.5 mL) of compound 25 (46 mg, 0.10 mmol) DIBAL-H (1.0 M in n-hexane, 0.3 mL, 0.3 mmol) was added at −78° C., and the mixture was stirred for 30 minutes. After the temperature of the reaction mixture was made to rise to 0° C., this was diluted with CH$_2$Cl$_2$ (5 mL), and an aqueous potassium sodium tartrate solution (7 mL) was added. The mixture was stirred for 6 hours and then extraction with CH$_2$Cl$_2$ was performed. The organic layer was dried over Na$_2$SO$_4$ and filtered, and the filtrate was concentrated in vacuo. The residue was purified by silica gel column chromatography (n-hexane/AcOEt=1:1) and compound 26 (22.5 mg, 52%) was obtained.

$^1$H-NMR (500 MHz, CDCl$_3$) δ: 9.24 (1H, s) 8.51 (1H, d, J=6.0 Hz), 7.85 (1H, s), 7.81 (1H, d, J=8.5 Hz), 7.65 (1H, d, J=5.5 Hz), 7.63 (1H, dd, J=8.5, 2.0 Hz), 6.03 (1H, d, J=9.0 Hz), 5.90 (1H, brs), 5.89 (1H, dd, J=9.0, 1.5 Hz), 4.93 (1H, t, J=7.0 Hz), 4.16 (1H, d, J=12.5 Hz), 4.11 (1M, d, J=12.5 Hz), 3.24 (1H, d, J=7.5 Hz), 3.24-3.19 (1H, m), 2.23 (1H, td, J=13.5, 8.5 Hz), 1.88 (1H, dd, J=12.0, 8.5 Hz), 0.73 (9H, t, J=8.0 Hz), 0.63 (3H, s), 0.46-0.31 (6H, m).

(8) Synthesis of compound 28 ((2R,3R,3aS,11aS, 11bR)-3-(isoquinolin-7-yl)-3a-methyl-2-((triethylsilyl)oxy)-1,3,3a,8,9,10,11a,11b-octahydrocyclopenta [c]xanthen-7(2H)-one)

To a CH$_2$Cl$_2$ solution (1.3 ml) of compound 26 (22.5 mg, 0.054 mmol), Dess-Martin periodinane (34.1 mg, 0.08 mmol) and NaHCO$_3$ (22.6 mg, 0.27 mmol) were added at 0° C., and the mixture was stirred at room temperature for 30 minutes. After the temperature of the reaction mixture was made to drop to 0° C., a saturated NH$_4$Cl solution was added and then extraction with CH$_2$Cl$_2$ was performed. The organic layer was dried over Na$_2$SO$_4$ and filtered, and the filtrate was con-centrated in vacuo. In this way, a mixture (27.5 mg) containing compound 27 was obtained.

To an AcOEt solution (2.7 mL) of the obtained product, 1,3-cyclohexanedione (12 mg, 0.11 mmol) and ethylenediamine (4.3 μL, 0.064 mmol) were added at 0° C., and the mixture was stirred at room temperature for 2 hours. After the temperature of the reaction mixture was made to drop to 0° C., water was added and then extraction with CH$_2$Cl$_2$ was performed. The organic layer was dried over Na$_2$SO$_4$ and filtered, and the filtrate was concentrated in vacuo. The residue was purified by silica gel column chromatography (n-hexane/AcOEt=1:1) and compound 28 (16.5 mg, 60% in 2 steps) was obtained.

$^1$H-NMR (500 MHz, CDCl$_3$) δ: 9.26 (1H, s), 8.51 (1H, d, J=6.0 Hz), 7.83 (1H, s), 7.81 (1H, d, J=8.5 Hz), 7.66 (1H, d, J=5.5 Hz), 7.61 (1H, dd, J=8.5, 1.5 Hz), 6.36 (1H, brs), 6.01 (1H, d, J=9.0 Hz), 5.78 (1H, d, J=9.0 Hz), 4.95 (1H, t, J=7.0 Hz), 4.81 (1H, dd, J=11.5, 2.5 Hz), 3.17 (1H, d, J=6.5 Hz), 2.84 (1H, td, J=13.5, 7.5 Hz), 2.57 (1H, ddd, J=18.0, 9.0, 5.0 Hz), 2.50 (1H, dt, J=18.0, 5.0 Hz), 2.44-2.40 (2H, m), 2.25 (1H, td, J=13.5, 8.5 Hz), 2.12-1.95 (3H, m), 0.75 (3H, s), 0.73 (9H, t, J=8.0 Hz), 0.46-0.31 (6H, m).

(9) Synthesis of compound 30 (CA-5, (3R,3aS,11aS, 11bR)-3-(isoquinolin-7-yl)-3a-methyl-1,3,3a,9,10, 11b-hexahydrocyclopenta[c]xanthene-2,7(8H,11aH)-dione)

To a MeOH solution (0.7 mL) of compound 26 (4.7 mg, 0.009 mmol), a 5% HCl solution (0.18 mL, 0.25 mmol) was added at 0° C., and the mixture was stirred for 10 minutes. After addition of NaHCO$_3$ (64 mg), the reaction mixture was dried over Na$_2$SO$_4$ and filtered, and the filtrated was concentrated in vacuo. The residue was dissolved in CHCl$_3$ and the insoluble matter was filtered off through a cotton plug. The filtrate was concentrated in vacuo and a mixture (5.4 mg) containing compound 29 was obtained.

To a CH$_2$Cl$_2$ solution (0.3 mL) of the obtained product, Dess-Martin periodinane (11.6 mg, 0.03 mmol) was added at 0° C., and the mixture was stirred at room temperature for 30 minutes. After the temperature of the reaction mixture was made to drop to 0° C., a saturated NH$_4$Cl solution and a saturated Na$_2$S$_2$O$_3$ solution were added and then extraction with CH$_2$Cl$_2$ was performed. The organic layer was dried over Na$_2$SO$_4$ and filtered, and the filtrate was concentrated in vacuo. The residue was purified by silica gel column chromatography (CHCl$_3$/MeOH/H$_2$O=100:3:1 (lower phase)) and compound 30 (3.3 mg, 91% in 2 steps) was obtained.

$^1$H-NMR (500 MHz, CDCl$_3$) δ: 9.26 (1H, s), 8.55 (1H, d, J=5.5 Hz), 7.84 (1H, d, J=8.5 Hz), 7.77 (1H, s), 7.67 (1H, d, J=5.5 Hz), 7.46 (1H, d, J=8.5 Hz), 6.47 (1H, brs), 6.16 (1H, d, J=9.0 Hz), 5.97 (1H, d, J=9.0 Hz) 4.99 (1H, J=9.0 Hz), 3.71 (1H, s), 2.90-2.81 (2H, m), 2.61 (1H, ddd, J=18.0, 9.5, 5.5 Hz), 2.56-2.44 (4H, m), 2.12-1.95 (2H, m), 0.80 (3H, s).

Example 6

Evaluation of Selective Anti Proliferative Activity Against Vascular Endothelial Cells (2)

CA-1, CA-2, CA-3, CA-4 and CA-5 were evaluated for anti-proliferative activity against normal human umbilical vein endothelial cells (HUVEC) and human pharyngeal carcinoma KB3-1 cells. The five test compounds were separately dissolved at predetermined concentrations in EtOH. HUVEC and KB3-1 were seeded in separate 96-well multiwell plates at 2×10$^3$ cells/100 μL/well and cultured in an atmosphere of 5% CO$_2$ at 37° C. for 24 hrs. Next, 1.0 µL each of the ethanol solutions containing the test compound or the control compound at various concentrations were added, and the cells were cultured under the same conditions for additional 72 hours. After 72 hours, 10 µL of WST-8 (2-(2-methoxy-4-nitrophenyl)-3-(4-nitrophenyl)-5-(2,4-disulfophenyl)-2H-tetrazolium, monosodium salt) reagent was added. After 3-hour incubation, the amount of water-soluble formazan formed in viable cells was colorimetrically determined measurement at OD 450 nm, and the growth inhibition ratio was calculated by comparison of the amount of formazan between the compound treatment groups and the non-treatment group.

Figure 8:
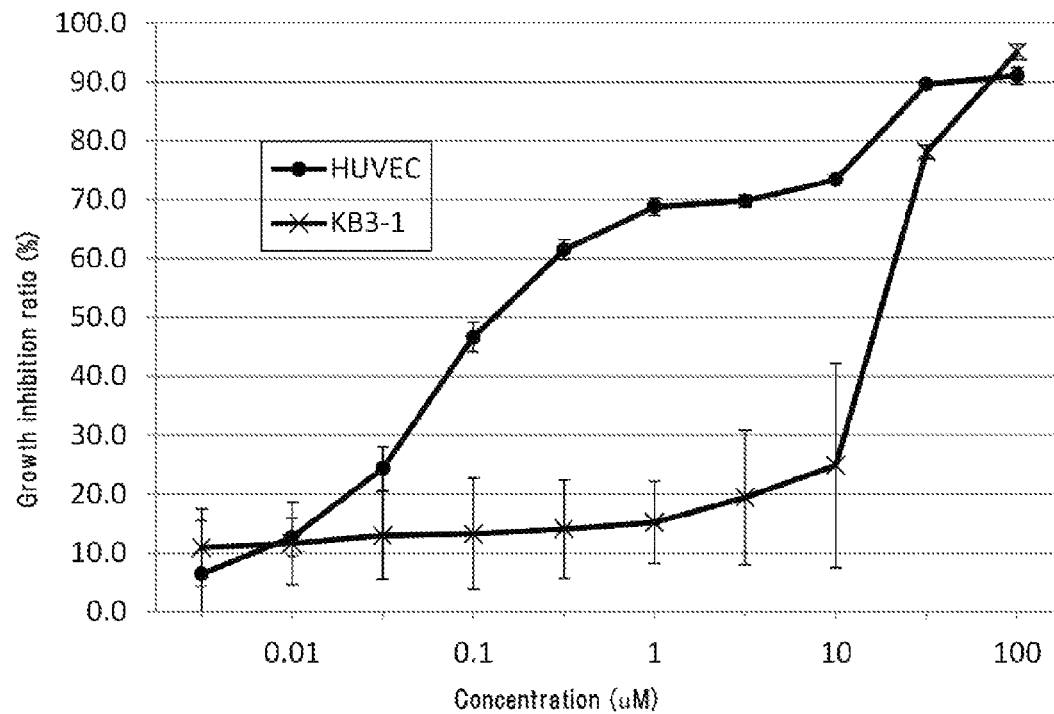
FIG. 8 shows the evaluation results of the compound represented by formula (II) (CA-1) in the test for selective anti-proliferative activity against vascular endothelial cells.
Figure 9:
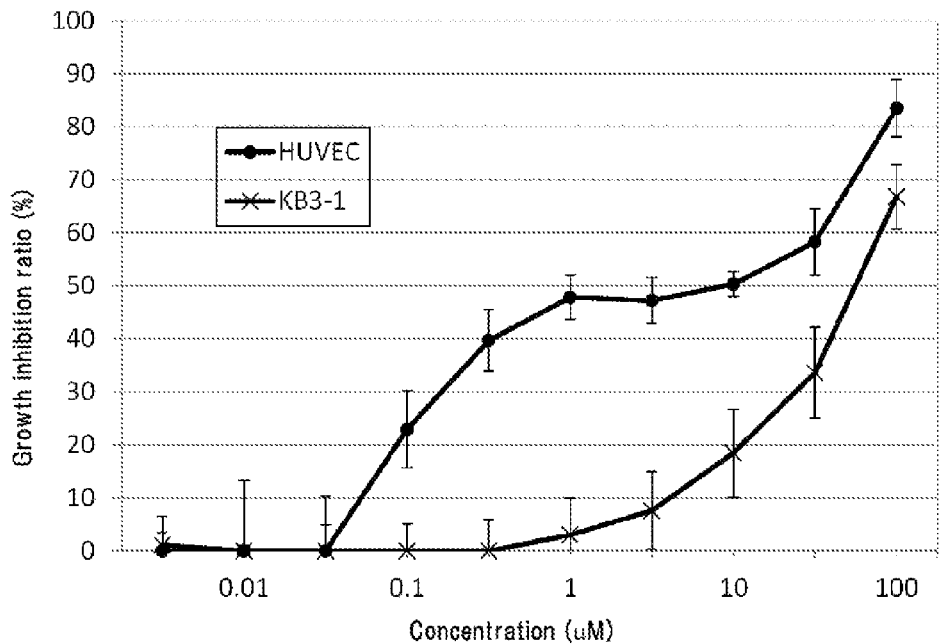
FIG. 9 shows the evaluation results of the compound represented by formula (XVIII) (CA-2) in the test for selective anti-proliferative activity against vascular endothelial cells.
Figure 10:
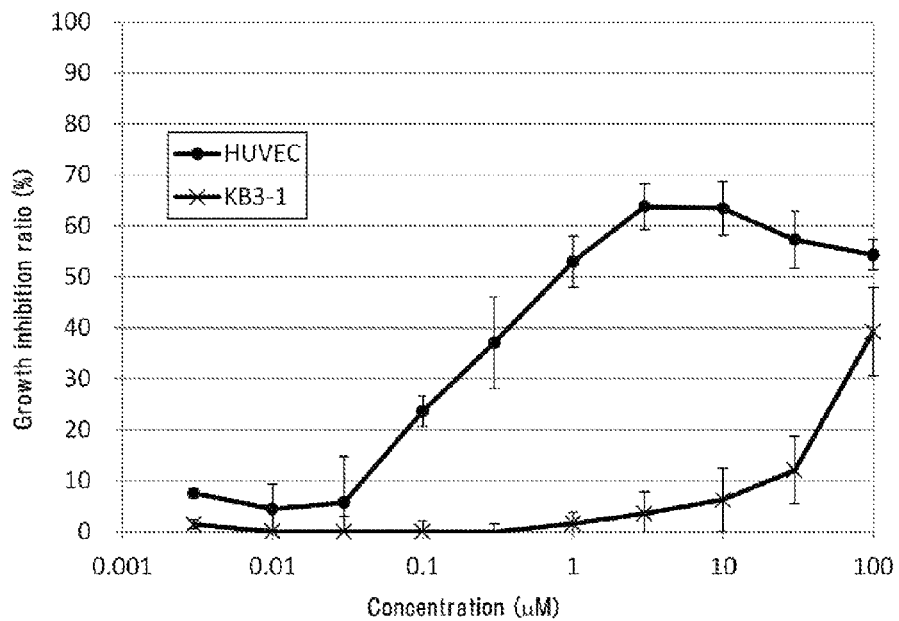
FIG. 10 shows the evaluation, results of the compound represented by formula (XIX) (CA-3) in the test for selective anti-proliferative activity against vascular endothelial cells.
Figure 11:
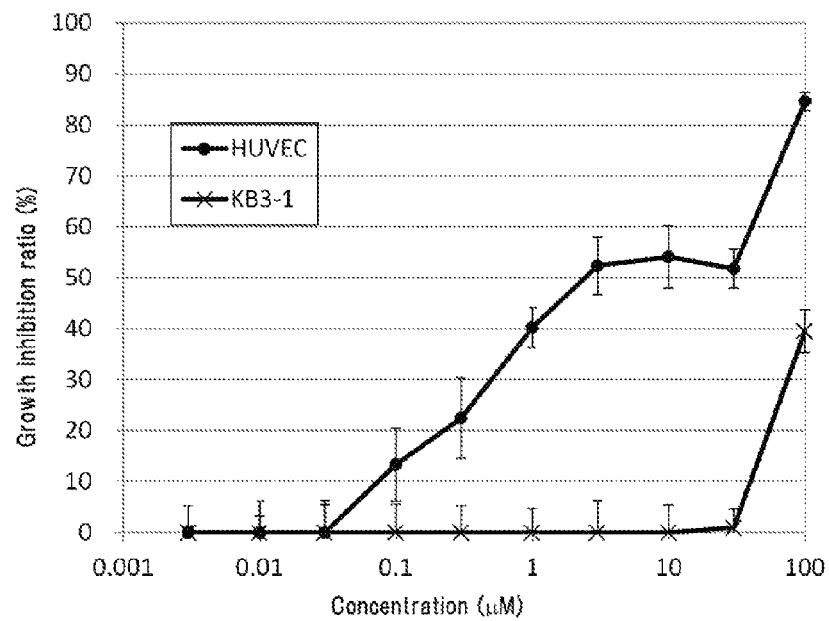
FIG. 11 shows the evaluation results of the compound represented by formula (XXIII) (CA-4) in the test for selective anti-proliferative activity against vascular endothelial cells.
Figure 12:
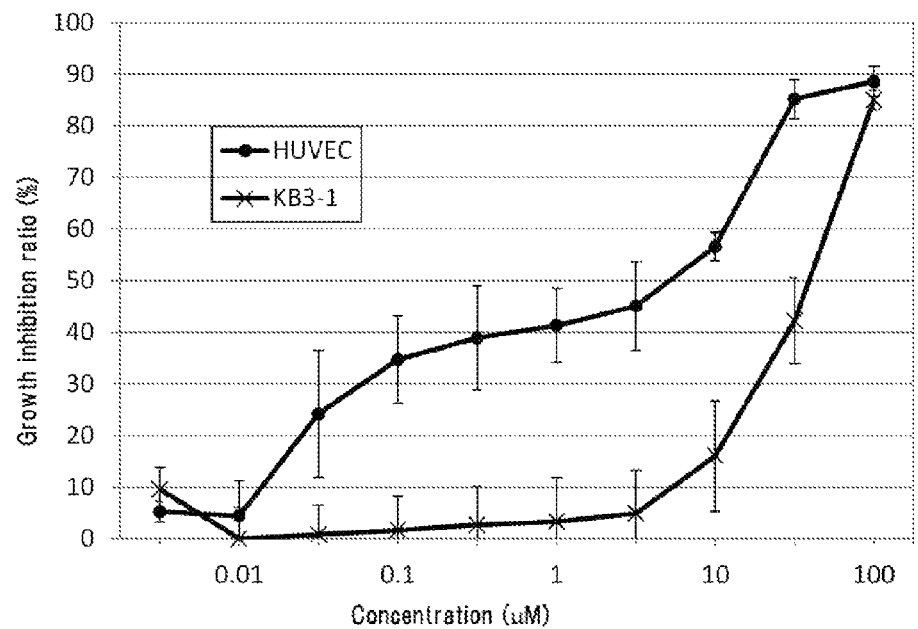
FIG. 12 shows the evaluation results of the compound represented by formula (LIV) (CA-5) in the test for selective anti-proliferative activity against vascular endothelial cells.

The results of CA-1 are shown in FIG. 8, the results of CA-2 are shown in FIG. 9, the results of CA-3 are shown in FIG. 10, the results of CA-4 are shown in FIG. 11, and the results of CA-5 were shown in FIG. 12. As is clear from FIGS. 8 to 12, each of these compounds selectively inhibits the growth of vascular endothelial cells.

Example 7

Evaluation of In Vivo Anti-Angiogenic Activity After Oral Administration

The test was performed in the same manner as in Example 3, except that oral administration was performed instead of intraperitoneal administration and that a 5.0 mg/kg administration group was additionally included.

Figure 13:
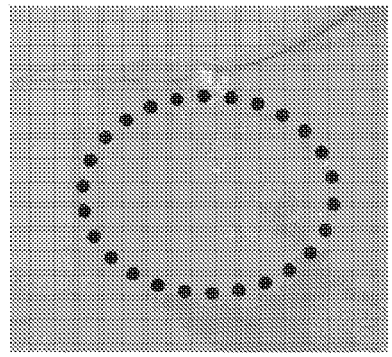
FIG. 13 shows images of the Matrigel injection sites in representative mice of all different groups in the test for in vivo anti-angiogenic activity after oral administration of the compound represented by formula (II) (CA-1).
Figure 13:
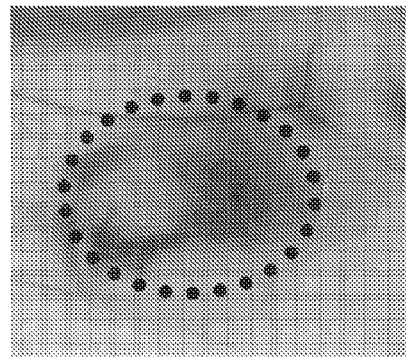
Figure 13:
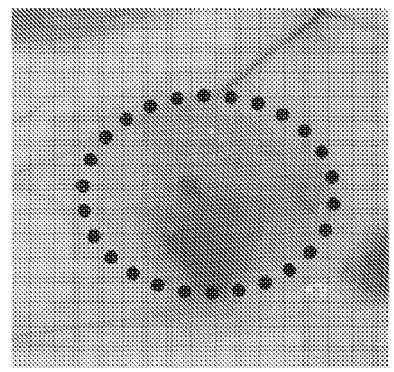
Figure 13:
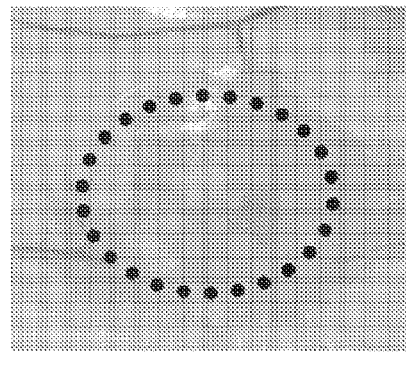
Figure 14:
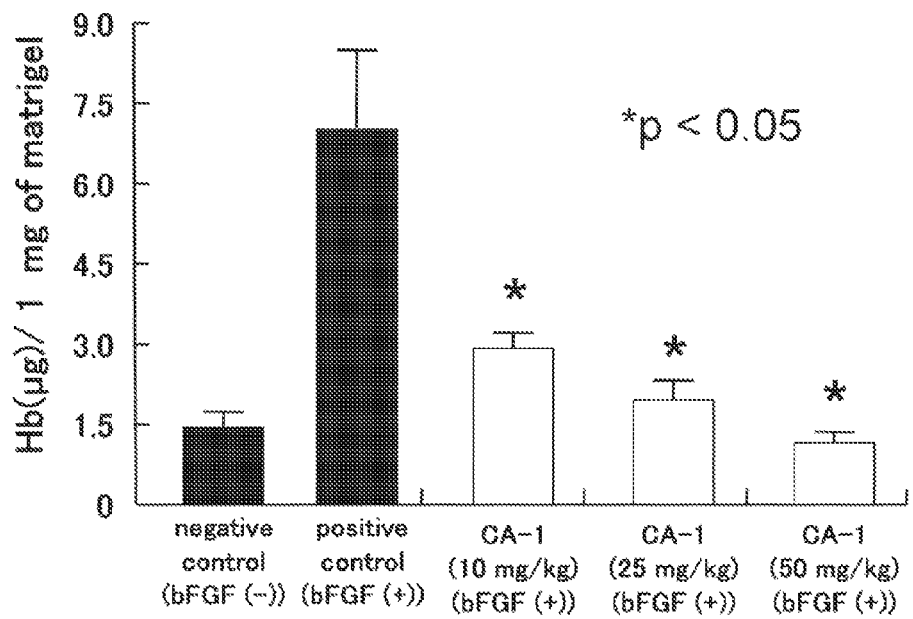
FIG. 14 shows a graph representing the measured amount of hemoglobin accumulated in the Matrigel subcutaneously injected into mice in the test for in vivo anti-angiogenic activity after oral administration of the compound represented by formula (II) (CA-1).

The results are shown in FIGS. 13 and 14. FIG. 13 shows images of the Matrigel injection sites in representative mice of all different groups except the 25 mg/kg administration group, and FIG. 14 shows a graph representing the measured amount of hemoglobin accumulated in the Matrigel. As is clear from FIGS. 13 and 14, CA-1 administered at not less than 10 mg/kg significantly reduced the amount of hemoglobin accumulated in the Matrigel, and in the 50 mg/kg administration group, the amount of hemoglobin was reduced to almost the same level as that of the group injected with Matrigel not supplemented with the proangiogenic factor bFGF. These results demonstrate that the test compound CA-1 orally administered also exhibits in vivo anti-angiogenic effect.

Example 8

Evaluation of Antitumor Activity in Mouse Cancer Cell Transplant Model after Oral Administration The test was performed in the same manner as in Example 3, except that oral administration was performed instead of intraperitoneal administration and that a 50 mg/kg administration group was included instead of the 5 mg/kg administration group.

Figure 15:
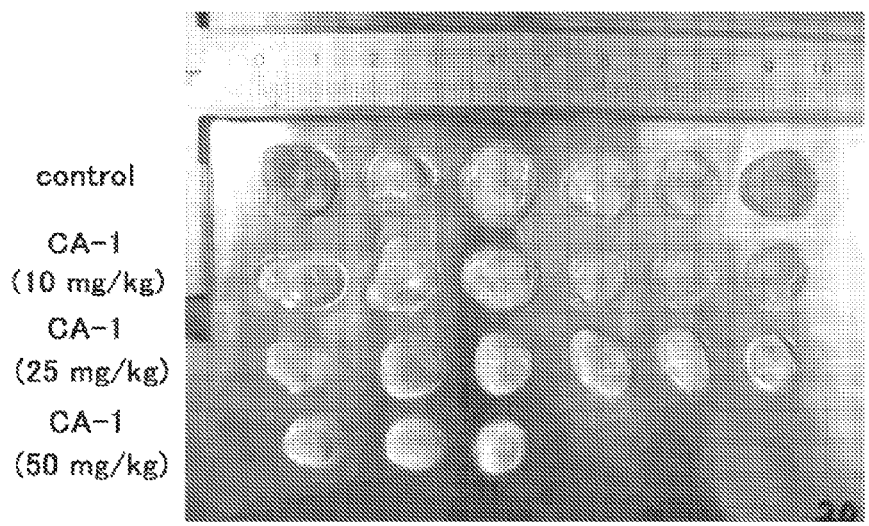
FIG. 15 shows an image for size comparison of tumors isolated from the mice of all groups in the test for antitumor activity in a mouse cancer cell transplant model after oral administration of the compound represented by formula (II) (CA-1).
Figure 16:
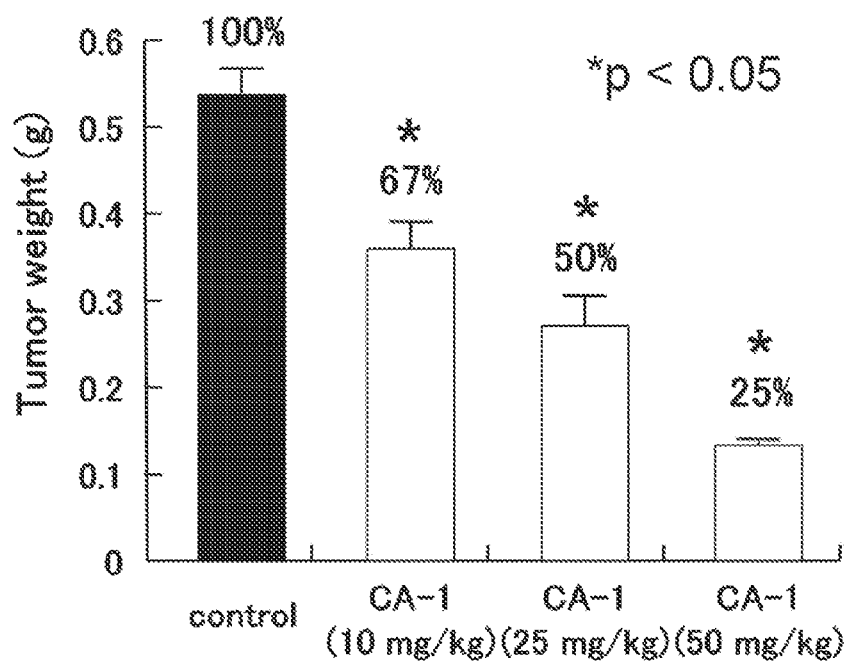
FIG. 16 shows a graph representing the measurement results of the tumor weight in the test for antitumor activity in a mouse cancer cell, transplant model after oral administration of the compound represented by formula (II) (CA-1).

The results are shown in FIGS. 15 and 16. FIG. 15 shows an image for size comparison of tumors isolated from the mice of all groups, and FIG. 16 shows a graph representing the measurement results of the tumor weight. As is clear from FIGS. 15 and 16, the tumor weights of the 10 mg/kg, 25 mg/kg and 50 mg/kg CA-1 administration groups were reduced to 67%, 50% and 25% of that of the control group, respectively. Thus, CA-1 was shown to have marked antitumor activity. In no groups, weight loss or diarrhea, or visual abnormalities in organs of the mice were observed.

The present invention is not limited to particular embodiments and examples described above, and various modifications can be made within the scope of the appended claims. Other embodiments provided by suitably combining technical means disclosed in separate embodiments of the present invention are also within the technical scope of the present invention. All the academic publications and patent literatures cited in the above description are incorporated herein by reference.

The invention claimed is:

1. A compound represented by the general formula (M):

[Formula 1]

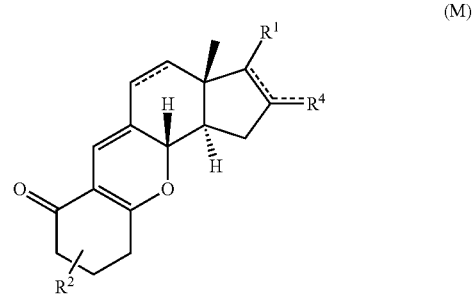

(M)

wherein R$^1$ represents a pyridyl group, a quinolyl group or an isoquinolyl group, R$^2$ represents a hydrogen atom, a substituted or unsubstituted alkyl group having 1 to 3 carbon atoms, OR$^3$, N(R$^3$)$_2$, C(=O)OR$^3$ or C(=O)N(R$^3$)$_2$, R$^3$ represents a hydrogen atom, an alkyl group having 1 to 4 carbon atoms, or an acyl group having 1 to 4 carbon atoms, R$^4$ represents a hydrogen atom, an oxygen atom or OR$^5$, and R$^5$ represents a hydrogen atom, an alkyl group having 1 to 3 carbon atoms, or an acyl group having 1 to 3 carbon atoms, and ----- is a single bond or double bond, with proviso that when a partial formula ----- R$^4$ is =R$^4$, a partial formula

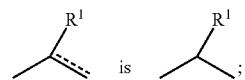

and when a partial formula

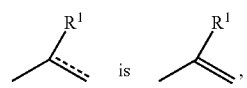

a partial formula ----- R$^4$ is —R$^4$; or a pharmaceutically acceptable salt thereof.

2. The compound according to claim 1, wherein R$^4$ is a hydrogen atom; or a pharmaceutically acceptable salt thereof.

3. The compound according to claim 1, which is represented by

Formula (II):

[Formula 3]

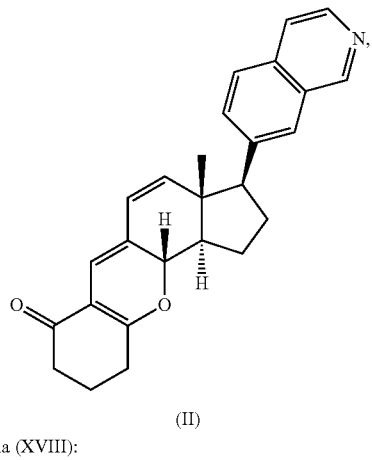

(II)

Formula (XVIII):

[Formula 4]

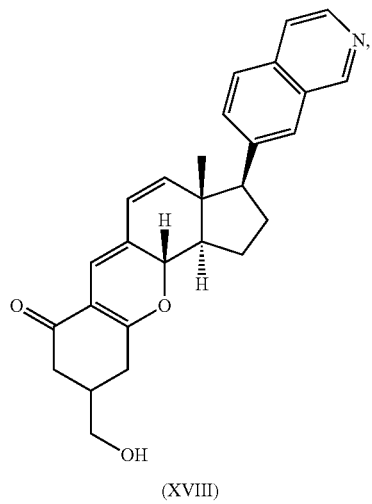

(XVIII)

Formula (XIX):

[Formula 5]

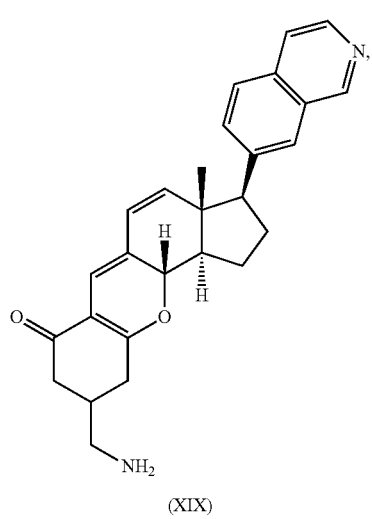

(XIX)

Formula (XXIII):

[Formula 6]

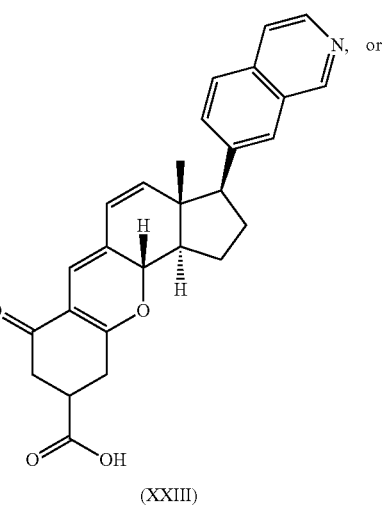

(XXIII)

Formula (LIV):

[Formula 7]

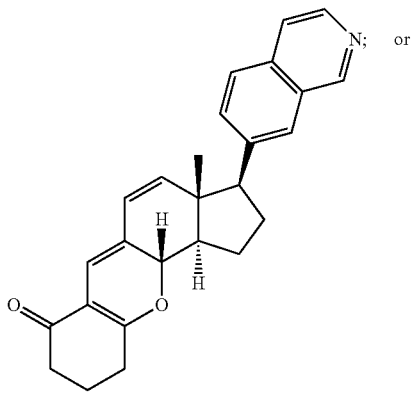

(LIV)

a pharmaceutically acceptable salt thereof.

4. A pharmaceutical composition, comprising the compound according to claim 1 or a pharmaceutically acceptable salt thereof, and a pharmaceutically acceptable carrier.

5. A vascular endothelial cell growth inhibitor, comprising the compound according to claim 1 or a pharmaceutically acceptable salt thereof as an active ingredient.

6. An angiogenesis inhibitor, comprising the compound according to claim 1 or a pharmaceutically acceptable salt thereof as an active ingredient.

7. A method for treatment of mouse sarcoma S180 cells, the method comprising administering, to a mouse, an effective amount of the compound according to claim 1 or a pharmaceutically acceptable salt thereof.

* * * * *